(12) United States Patent
Tran et al.

(10) Patent No.: US 12,213,676 B2
(45) Date of Patent: Feb. 4, 2025

(54) SYSTEMS AND METHODS FOR CUSTOMIZABLE FLOW DIVERTER IMPLANTS

(71) Applicant: eLum Technologies, Inc., Fremont, CA (US)

(72) Inventors: Quang Tran, Atherton, CA (US); Yen Tu, Fremont, CA (US); Noelle Bagnall, Irvine, CA (US); Victor Barajas, Pleasanton, CA (US); David Li, Irvine, CA (US)

(73) Assignee: eLum Technologies, Inc., Fremont, CA (US)

( * ) Notice: Subject to any disclaimer, the term of this patent is extended or adjusted under 35 U.S.C. 154(b) by 0 days.

(21) Appl. No.: 18/776,051

(22) Filed: Jul. 17, 2024

(65) Prior Publication Data
US 2024/0398413 A1    Dec. 5, 2024

Related U.S. Application Data

(63) Continuation-in-part of application No. 18/236,674, filed on Aug. 22, 2023, which is a
(Continued)

(51) Int. Cl.
*A61B 17/12* (2006.01)
*A61B 17/00* (2006.01)

(52) U.S. Cl.
CPC .. *A61B 17/12109* (2013.01); *A61B 17/12031* (2013.01); *A61B 17/12172* (2013.01);
(Continued)

(58) Field of Classification Search
CPC ............... A61F 2002/9534; A61F 2/95; A61B 2017/12054; A61B 17/12172;
(Continued)

(56) References Cited

U.S. PATENT DOCUMENTS 5,624,449 A    4/1997    Pham et al.
5,746,769 A    5/1998    Ton et al.
(Continued)

FOREIGN PATENT DOCUMENTS

CA    3051087 A1    2/2020
CN    106214205 A    12/2016
(Continued)

*Primary Examiner* — Robert A Lynch
*Assistant Examiner* — Christina C Lauer
(74) *Attorney, Agent, or Firm* — Kilpatrick Townsend & Stockton LLP

(57) ABSTRACT

Neurovascular flow diverter and delivery systems, and methods of using the same are described herein. The systems can include a customizing member including an introducer sheath, a catheter, a deployable flow diverter that can be contained in the introducer sheath or in the catheter, a core wire, and one or several deployment features coupled to the core wire and engaging the flow diverter. The customizing member includes a tubing extending along and around a distal portion of the introducer sheath. This tubing is cuttable and contains a distal end of the flow diverter. The length of the flow diverter can be customized by cutting through the tubing and the therein contained flow diverter.

30 Claims, 29 Drawing Sheets

Related U.S. Application Data continuation-in-part of application No. 18/112,904, filed on Feb. 22, 2023.

(52) U.S. Cl.
CPC ............... *A61B 2017/00477* (2013.01); *A61B 2017/1205* (2013.01)

(58) Field of Classification Search
CPC ........ A61B 17/12118; A61B 17/12113; A61B 2017/1205; A61B 17/12131; A61B 17/12109; A61M 25/0668; A61M 2039/1027; A61M 2039/25; A61M 39/10; A61M 39/25
USPC .......................................................... 600/36
See application file for complete search history.

(56) References Cited

U.S. PATENT DOCUMENTS

| | | | |
|---|---|---|---|
| 6,645,183 B2* | 11/2003 | Christensen | A61M 5/16804 604/246 |
| 7,309,351 B2 | 12/2007 | Escamilla et al. | |
| 7,867,267 B2 | 1/2011 | Sullivan et al. | |
| 7,942,894 B2 | 5/2011 | West | |
| 8,172,891 B2 | 5/2012 | Shelso | |
| 8,211,141 B2 | 7/2012 | Davis, III et al. | |
| 8,241,345 B2 | 8/2012 | Phung | |
| 8,317,859 B2 | 11/2012 | Snow et al. | |
| 8,523,887 B2 | 9/2013 | Grayzel et al. | |
| 8,636,760 B2 | 1/2014 | Garcia et al. | |
| 8,784,466 B2 | 7/2014 | Igaki | |
| 8,986,362 B2 | 3/2015 | Snow et al. | |
| 9,017,365 B2 | 4/2015 | Lagodzki et al. | |
| 9,119,738 B2 | 9/2015 | Fish | |
| 9,119,948 B2 | 9/2015 | Lee et al. | |
| 9,192,499 B2 | 11/2015 | Gibbons, Jr. | |
| 9,326,876 B2 | 5/2016 | Acosta et al. | |
| 9,675,488 B2 | 6/2017 | Newell et al. | |
| 9,877,856 B2 | 1/2018 | Liang et al. | |
| 9,943,313 B2 | 4/2018 | Jones et al. | |
| 9,980,837 B2 | 5/2018 | Clerc | |
| 10,034,670 B2 | 7/2018 | Elgård et al. | |
| 10,064,747 B2 | 9/2018 | Berez et al. | |
| 10,315,011 B2 | 6/2019 | Vongphakdy et al. | |
| 10,426,612 B2 | 10/2019 | Costello | |
| 10,888,331 B2 | 1/2021 | Pederson et al. | |
| 10,898,356 B2 | 1/2021 | Longo et al. | |
| 10,925,611 B2 | 2/2021 | Hebert et al. | |
| 10,932,933 B2 | 3/2021 | Bardsley et al. | |
| 10,945,867 B2 | 3/2021 | Nageswaran et al. | |
| 11,051,822 B2 | 7/2021 | Divino et al. | |
| 11,065,138 B2 | 7/2021 | Schreck et al. | |
| 11,071,637 B2 | 7/2021 | Dawson et al. | |
| 11,083,611 B2 | 8/2021 | Loganathan | |
| 11,129,738 B2 | 9/2021 | Gorochow | |
| 2001/0034509 A1* | 10/2001 | Cragg | A61M 37/0069 604/362 |
| 2002/0016597 A1 | 2/2002 | Dwyer et al. | |
| 2005/0209678 A1 | 9/2005 | Henkes et al. | |
| 2009/0292262 A1 | 11/2009 | Adams et al. | |
| 2010/0249758 A1* | 9/2010 | Sengun | A61F 2/30756 606/1 |
| 2012/0041470 A1 | 2/2012 | Shrivastava et al. | |
| 2012/0226343 A1 | 9/2012 | Vo et al. | |
| 2014/0180387 A1 | 6/2014 | Khenansho et al. | |
| 2014/0277099 A1* | 9/2014 | Wallace | A61B 17/12031 606/200 |
| 2014/0277360 A1 | 9/2014 | Girnary et al. | |
| 2016/0100965 A1 | 4/2016 | Nishigishi | |
| 2016/0302794 A1 | 10/2016 | Torp et al. | |
| 2017/0049596 A1 | 2/2017 | Schabert | |
| 2018/0049892 A1 | 2/2018 | Henkes et al. | |
| 2019/0142567 A1 | 5/2019 | Janardhan et al. | |
| 2019/0290458 A1 | 9/2019 | Slazas et al. | |
| 2019/0314179 A1 | 10/2019 | Nageswaran et al. | |
| 2019/0374228 A1 | 12/2019 | Wallace et al. | |
| 2020/0061099 A1 | 2/2020 | Li et al. | |
| 2020/0368049 A1 | 11/2020 | Vong et al. | |
| 2021/0330332 A1 | 10/2021 | Chou et al. | |
| 2022/0062017 A1 | 3/2022 | Zhang et al. | |

FOREIGN PATENT DOCUMENTS

| | | |
|---|---|---|
| CN | 111528956 B | 6/2021 |
| EP | 3250157 A4 | 10/2018 |
| FR | 2939637 A1 | 6/2010 |
| WO | 2004026371 A2 | 4/2004 |
| WO | 2016122862 A1 | 8/2016 |
| WO | 2020134024 A1 | 7/2020 |

\* cited by examiner

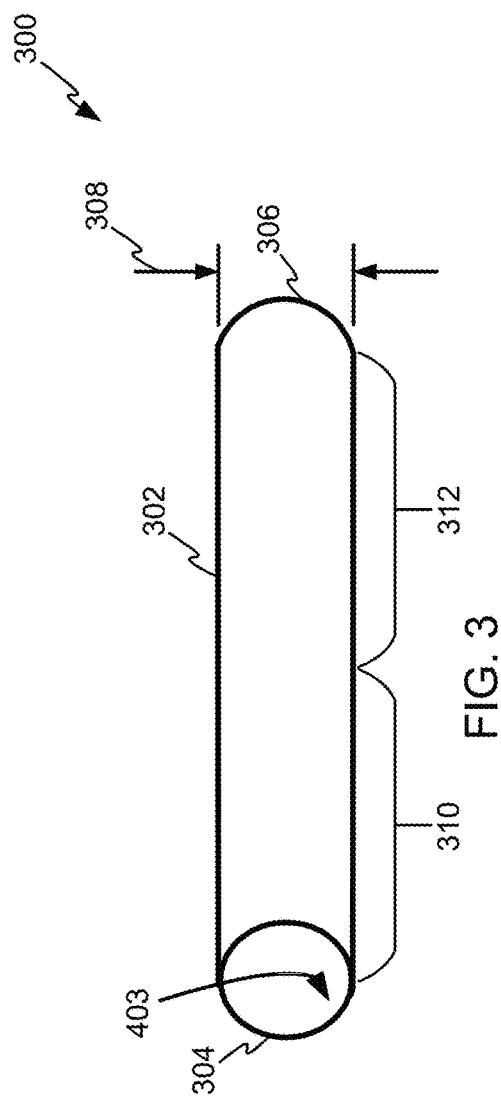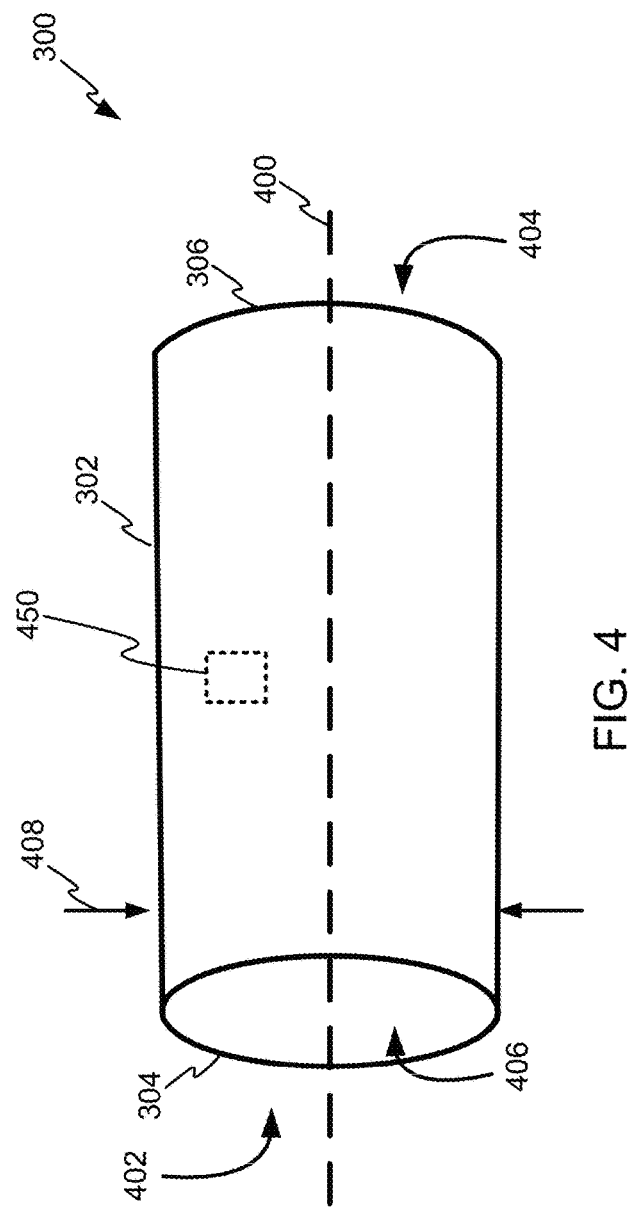

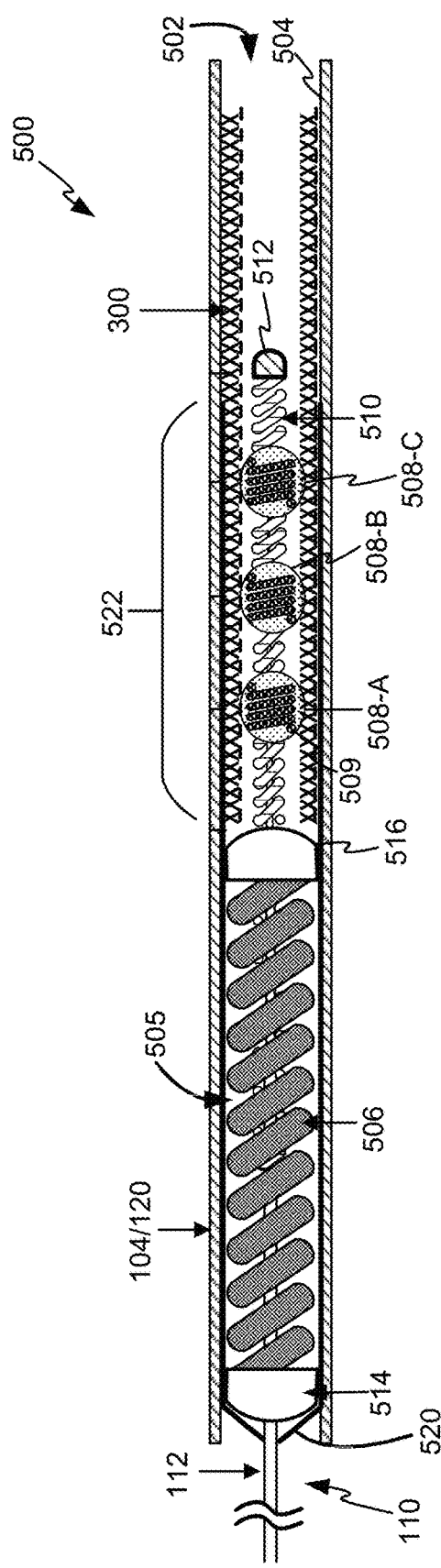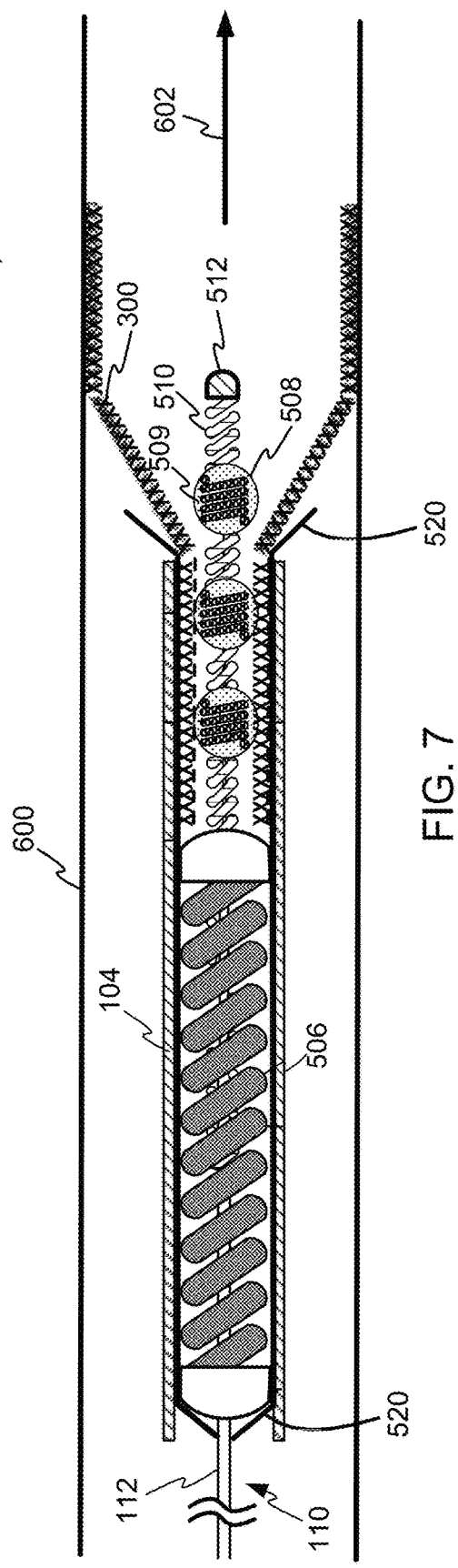

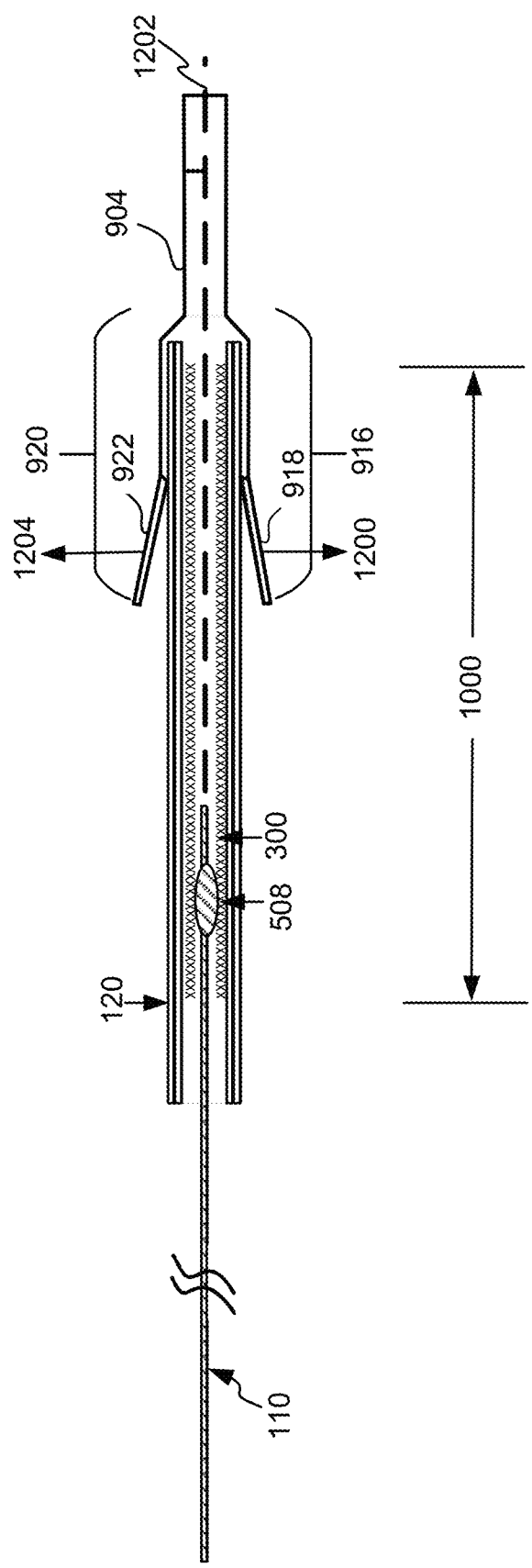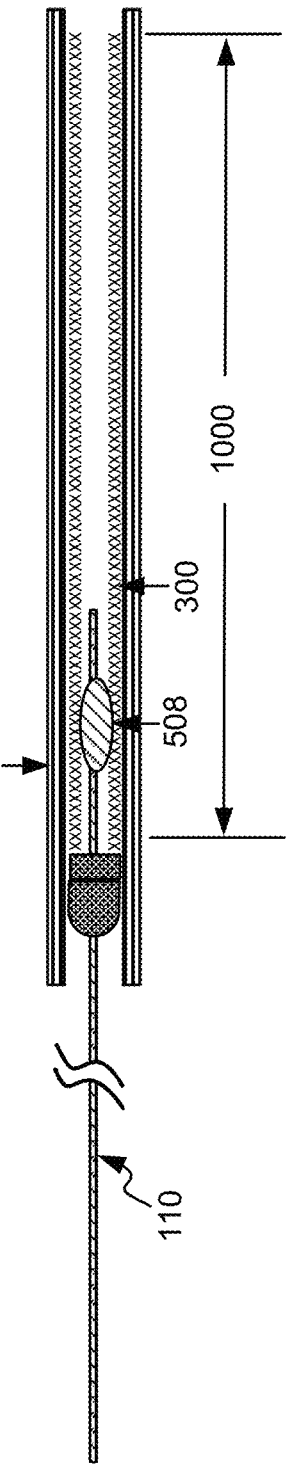

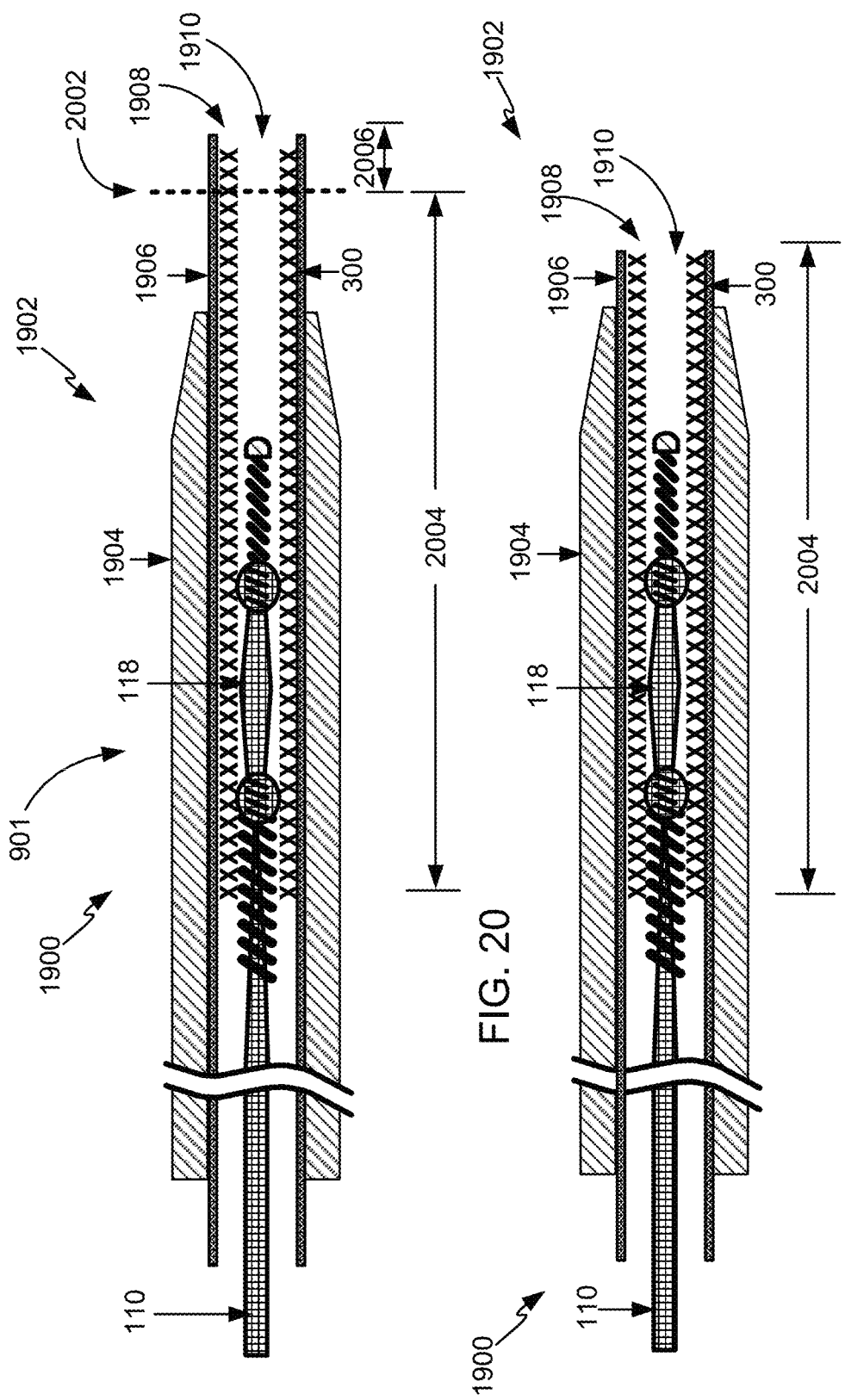

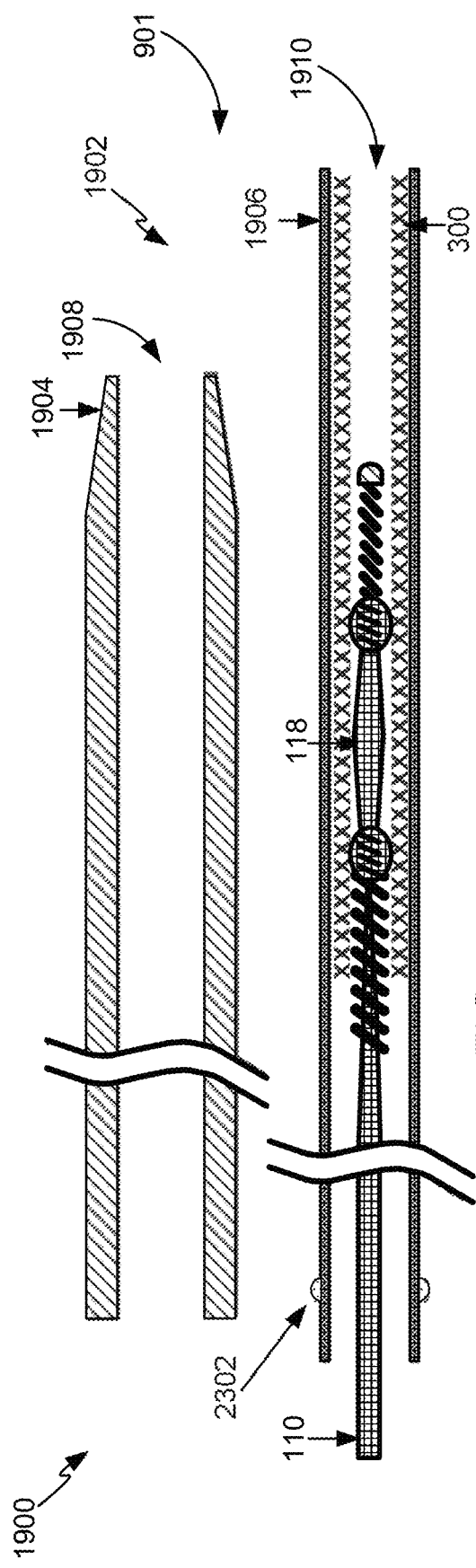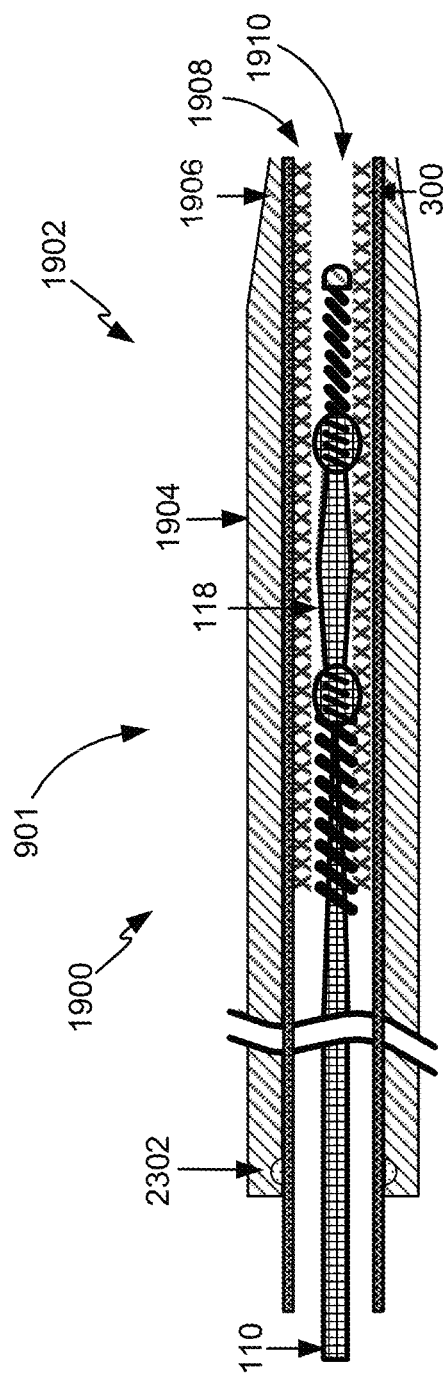
FIG. 23
FIG. 24

SYSTEMS AND METHODS FOR CUSTOMIZABLE FLOW DIVERTER IMPLANTS

CROSS REFERENCE TO RELATED APPLICATION DATA

The present application is a Continuation-in-Part of U.S. patent application Ser. No. 18/236,674 filed Aug. 22, 2023, which is a Continuation-in-Part of U.S. patent application Ser. No. 18/112,904 filed Feb. 22, 2023, the disclosures of which are incorporated herein by reference in their entirety for all purposes.

The subject matter of this application is related to U.S. Provisional Appln. No. 63/313,205 filed Feb. 23, 2022, assigned to the assignee herein, entitled: NEUROVASCULAR FLOW DIVERTER AND DELIVERY SYSTEMS; and U.S. patent application Ser. No. 18/112,963 filed Feb. 22, 2023, assigned to the assignee herein, entitled: NEUROVASCULAR FLOW DIVERTER AND DELIVERY SYSTEMS; and U.S. patent application Ser. No. 18/113,010 filed Feb. 22, 2023, assigned to the assignee herein, entitled: NEUROVASCULAR FLOW DIVERTER AND DELIVERY SYSTEMS; and U.S. patent application Ser. No. 18/236,663 filed Aug. 22, 2023, assigned to the assignee herein, entitled: NEUROVASCULAR FLOW DIVERTER AND DELIVERY SYSTEMS, the disclosures of which are incorporated herein by reference in their entirety for all purposes.

BACKGROUND

An aneurysm is a bulge in a blood vessel caused by a weakness in the blood vessel wall which balloons and fills with blood. Aneurysms frequently occur where a blood vessel branches. As blood passes through the weakened blood vessel, the blood pressure causes a small area to bulge outwards like a balloon. While an aneurysm can form in any blood vessel in the body, they are most common in arteries that transport blood away from the heart, such as the aorta, or in the brain.

An aneurysm that forms inside the brain is referred to as an intracranial aneurysm or as a cerebral aneurysm. Brain aneurysms typically only cause noticeable symptoms if they burst, rupture, or leak. Rupture or bursting of a brain aneurysm creates a serious life-threatening condition known as a subarachnoid hemorrhage. Symptoms of such a hemorrhage include a sudden and agonizing headache, a stiff neck, sickness and vomiting, and pain when looking at light. A subarachnoid hemorrhage is life threatening and is a very serious medical emergency.

Because of the grave risks posed by such hemorrhage, prevention, early detection, and safe and efficacious treatment of cerebral aneurysms is desired. However, the complex nature of the neural vasculature, including the small diameter and tortuous anatomy of many of the blood vessels make such treatments difficult. In light of the risks posed by subarachnoid hemorrhage and the challenges in treating cerebral aneurysms, improved treatment systems and methods are desired.

Aneurysms arise from vessels having a wide range of diameters. Side branches and/or bifurcations increase the need to have varying flow diverter length selections in supply. Hospitals must therefore carry a wide variety of flow diverters having different lengths and diameter sizes, resulting in a large number of SKUs to manage. It becomes economically burdensome to maintain a full range of sizes to optimally match flow diverter implants to a desired location. Improved flexibility in flow diverter length selections, while reducing the number of SKUs, is desired.

BRIEF SUMMARY

The present disclosure relates to systems, devices, and methods for customizing a flow diverter for delivery into a neurovascular blood vessel to treat an aneurysm.

The systems can include an elongate tubular member having a proximal end and a distal end. The elongate tubular member includes an interior wall defining a lumen. The flow diverter includes a proximal end and a distal end and defines a flow channel extending therethrough. The flow diverter is partially contained within the lumen of the elongate tubular member in a constrained configuration. The flow diverter extends a first length beyond the distal end of the elongate tubular member. A deployment wire extends into the lumen of the elongate tubular member and into the flow channel of the flow diverter. The deployment wire includes a proximal end, a distal end, and a distal portion having a taper. The deployment wire includes at least one deployment feature coupled to the flow diverter such that movement of the deployment wire relative to the elongate tubular member moves the flow diverter relative to the elongate tubular member. A tubing extends along and around the distal portion of the elongate tubular member. The tubing extends a second length beyond the distal end of the elongate tubular member. The distal end of the flow diverter is within the tubing. The tubing is cuttable.

The flow diverter is cuttable within the tubing to a variable length. In some embodiments, the tubing comprises graduation markings equally spaced along a distal end of the tubing for cutting the flow diverter and/or the tubing to the desired length. In some embodiments, the first length and the second length are equal.

In some embodiments, deployment features can include a pusher and at least one friction bump. Both the pusher and the at least one friction bump can be located along a distal portion of the deployment wire, with at least one friction bump located distal of the pusher. In some embodiments, the at least one friction bump is inside of the flow channel of the flow diverter and engaged with a portion of the flow diverter. In at least some approaches, a tip coil extends distally from the friction bump. The deployment wire can terminate before the distal end of the flow diverter such that the distal end of the deployment wire does not extend into the tubing. The deployment wire does not extend distally beyond the distal end of the flow diverter.

In some embodiments, a deployment features includes at least on friction bump. The at least one friction bump may be in a plurality of friction bumps. The plurality of friction bumps are equally spaced.

In some embodiments, the system includes a template having a top, a bottom, a front, a back, a first side, and a second side. The template includes graduation markings equally spaced along the bottom of at least one of the front of the template and the back of the template. The graduation markings are configured to aid in cutting the flow diverter to the desired length. The template correlates the graduation markings to a deployed length of the flow diverter.

In at least some embodiments, the template further includes a cutting notch extending through the bottom of the template. The cutting notch is proximate to one of the first side and the second side. The graduation markings are positioned between the cutting notch and the other of the first side and the second side.

The template can include a first set of graduation markings along the bottom of the front of the template and a second set of graduation markings along the bottom of the back of the template. One of the front of the template and the back of the template is configured for right-handed users and the other of the front of the template and the back of the template is configured for left-handed users.

The tubing includes a proximal end, a distal end, a first longitudinal portion having a first proximal pull tab, and a second longitudinal portion having a second proximal pull tab. Each of the first longitudinal portion and the second longitudinal portion extend from the proximal end of the tubing to the distal end of the tubing. The tubing is peelably removeable from the distal portion of the elongate tubular member by separating the first longitudinal portion from the second longitudinal portion. In some embodiments, the tubing includes a polymer tubing. In some embodiments, the tubing is transparent such that the flow diverter is visible within the tubing.

In some embodiments, the system includes a protective sleeve extending along and around the proximal end of the flow diverter. The protective sleeve is configured to reduce friction and/or reduce damage to the flow diverter when the flow diverter is moved relative to the elongate tubular member.

The flow diverter can include a self-expanding member having a proximal end and a distal end. The self-expanding member includes a braid.

In various embodiments, the systems can include an introducer sheath, a catheter, a deployable flow diverter that can be contained in the introducer sheath or in the catheter, a core wire, and one or several deployment features coupled to the core wire and engaging the flow diverter. The core wire can be tapered. The deployment features can include a pusher, one or several friction bumps, one or several deployment coils, a self-expanding element, a supporting coil, a tip coil, and/or an atraumatic tip. These deployment features can be arranged in different combinations to facilitate deployment of the flow diverter.

One aspect of the present disclosure relates to systems, devices, and methods for customizing a flow diverter for delivery into a neurovascular blood vessel to treat an aneurysm. The systems can include an elongate tubular member having a proximal end and a distal end. The elongate tubular member includes an interior wall defining a lumen. The flow diverter includes a proximal end and a distal end. The flow diverter is partially contained within the lumen of the elongate tubular member in a constrained configuration. The flow diverter extends a first length beyond the distal end of the elongate tubular member. A deployment wire extends into the lumen of the elongate tubular member. The deployment wire includes a proximal end, a distal end, and a distal portion having a taper. The deployment wire includes at least one deployment feature coupled to the flow diverter such that movement of the deployment wire relative to the elongate tubular member moves the flow diverter relative to the elongate tubular member. The system includes a template having a top, a bottom, a first side, a second side, a front, and a back. The template includes graduation markings equally spaced along the bottom. The graduation markings are configured to aid in cutting the flow diverter to the variable length.

The flow diverter is cuttable. In some embodiments, the flow diverter includes a braided member including a plurality of strands. The strands can include a wire having a diameter of approximately 0.0008 inches. The wire includes a drawn filled tube (DFT), in some embodiments.

In at least some embodiments, the template further includes a cutting notch extending through the bottom of the template. The cutting notch is proximate to one of the first side and the second side. The graduation markings are positioned between the cutting notch and the other of the first side and the second side.

The template includes a formula configured to aid in cutting the flow diverter to the variable length. The formula can be printed along the top portion of the template. The graduation markings and the formula can be printed on each of the front and the back of the template. In some embodiments, the template correlates the graduation markings to a deployed length of the flow diverter.

The template can include a first set of graduation markings along the bottom of the front of the template and a second set of graduation markings along the bottom of the back of the template. One of the front of the template and the back of the template is configured for right-handed users and the other of the front of the template and the back of the template is configured for left-handed users.

The system can further include a tubing extending along and around the distal portion of the elongate tubular member. The tubing extends beyond the distal end of the elongate tubular member. The distal end of the flow diverter is contained in the tubing. The tubing is peelably removeable from the distal portion of the elongate tubular member.

The tubing includes a proximal end, a distal end, a first longitudinal portion having a first proximal pull tab, and a second longitudinal portion having a second proximal pull tab. Each of the first longitudinal portion and the second longitudinal portion extend from the proximal end of the tubing to the distal end of the tubing. The tubing is peelably removeable from the distal portion of the elongate tubular member by separating the first longitudinal portion from the second longitudinal portion.

In various embodiments, the systems can include an introducer sheath, a catheter, a deployable flow diverter that can be contained in the introducer sheath or in the catheter, a core wire, and one or several deployment features coupled to the core wire and engaging the flow diverter. The core wire can be tapered. The deployment features can include a pusher, one or several friction bumps, one or several deployment coils, a self-expanding element, a supporting coil, a tip coil, and/or an atraumatic tip. These deployment features can be arranged in different combinations to facilitate deployment of the flow diverter.

One aspect of the present disclosure includes a method for customizing a flow diverter for delivery into a neurovascular blood vessel to treat an aneurysm. The method includes determining a desired length of a flow diverter of a flow diverter system. The system includes an elongate tubular member having a proximal end and a distal end and an interior wall defining a lumen. The system includes a flow diverter including a proximal end and a distal end. The flow diverter is partially contained within the lumen of the elongate tubular member in a constrained configuration. The flow diverter extends a first length beyond the distal end of the elongate tubular member. The system includes a deployment wire extending into the lumen of the elongate tubular member. The deployment wire includes a proximal end, and a distal end. The deployment wire includes at least one deployment feature coupled to the flow diverter such that movement of the deployment wire relative to the elongate tubular member moves the flow diverter relative to the elongate tubular member. The system further includes a tubing coupled to the distal portion of the elongate tubular member, wherein the tubing extends distally a second length beyond the distal end of the elongate tubular member, wherein the distal end of the flow diverter is within the tubing. The method includes cutting the flow diverter and the tubing such that the flow diverter is the desired length.

The method includes retracting the flow diverter into the elongate tubular member. The flow diverter can be retracted into the elongate tubular member by distally retracting the deployment wire.

In some embodiments, the method further includes separating the tubing from the distal portion of the elongate tubular member after the flow diverter is retracted into the elongate tubular member. The tubing is separated from the distal portion of the elongate tubular member after the flow diverter is retracted into the elongate tubular member.

The tubing includes a proximal end, a distal end, a first longitudinal portion having a first proximal pull tab, and a second longitudinal portion having a second proximal pull tab. Each of the first longitudinal portion and the second longitudinal portion extend from the proximal end of the tubing to the distal end of the tubing. The tubing is peelably removeable from the distal portion of the elongate tubular member by separating the first longitudinal portion from the second longitudinal portion. Peeling the tubing from the distal portion of the elongate tubular member includes separating the first longitudinal portion from the second longitudinal portion.

The method further includes loading the flow diverter into the elongate tubular member.

One aspect of the present disclosure includes a method for customizing a flow diverter for delivery into a neurovascular blood vessel to treat an aneurysm. The method includes determining a desired length of a flow diverter of a flow diverter system using a template. The system includes an elongate tubular member having a proximal end and a distal end and an interior wall defining a lumen. The system includes a flow diverter including a proximal end and a distal end. The flow diverter is partially contained within the lumen of the elongate tubular member in a constrained configuration. The flow diverter extends a first length beyond the distal end of the elongate tubular member. The system includes a deployment wire extending into the lumen of the elongate tubular member. The deployment wire includes a proximal end, and a distal end. The deployment wire includes at least one deployment feature coupled to the flow diverter such that movement of the deployment wire relative to the elongate tubular member moves the flow diverter relative to the elongate tubular member. The system further includes a tubing coupled to the distal portion of the elongate tubular member, wherein the tubing extends distally a second length beyond the distal end of the elongate tubular member, wherein the distal end of the flow diverter is within the tubing. The method includes cutting the flow diverter and the tubing such that the flow diverter is the desired length.

The template includes a top, a bottom, a front, a back, a first side, and a second side. The template includes graduation markings equally spaced along the bottom of at least one of the front of the template and the back of the template. The graduation markings are configured to aid in cutting the flow diverter to the desired length.

In at least some embodiments, the template further includes a cutting notch extending through the bottom of the template. The cutting notch is proximate to one of the first side and the second side. The graduation markings are positioned between the cutting notch and the other of the first side and the second side.

The template can include a first set of graduation markings along the bottom of the front of the template and a second set of graduation markings along the bottom of the back of the template. One of the front of the template and the back of the template is configured for right-handed users and the other of the front of the template and the back of the template is configured for left-handed users.

The template includes a formula configured to aid in cutting the flow diverter to the variable length. The formula can be printed along the top portion of the template. The graduation markings and the formula can be printed on each of the front of the template and the back of the template. In some embodiments, the template correlates the graduation markings to a deployed length of the flow diverter.

The method includes retracting the flow diverter into the elongate tubular member. The flow diverter can be retracted into the elongate tubular member by distally retracting the deployment wire.

The flow diverter system includes a tubing coupled to the distal portion of the elongate tubular member. The tubing extends distally a second length beyond the distal end of the elongate tubular member. The distal end of the flow diverter can be within the tubing.

In some embodiments, cutting the flow diverter such that the flow diverter is the desired length includes cutting the tubing.

In some embodiments, the method further includes separating the tubing from the distal portion of the elongate tubular member. The tubing is separated from the distal portion of the elongate tubular member after the flow diverter is retracted into the elongate tubular member. The tubing is separated from the distal portion of the elongate tubular member by peeling the tubing from the distal portion of the elongate tubular member.

The tubing includes a proximal end, a distal end, a first longitudinal portion having a first proximal pull tab, and a second longitudinal portion having a second proximal pull tab. Each of the first longitudinal portion and the second longitudinal portion extend from the proximal end of the tubing to the distal end of the tubing. The tubing is peelably removeable from the distal portion of the elongate tubular member by separating the first longitudinal portion from the second longitudinal portion. Peeling the tubing from the distal portion of the elongate tubular member includes separating the first longitudinal portion from the second longitudinal portion.

The method further includes loading the flow diverter into the elongate tubular member.

One aspect relates to a system for customizing a flow diverter for delivery into a neurovascular blood vessel to treat an aneurysm. The system includes a customizing member having a proximal end and a distal end. The customizing member includes an interior wall defining a lumen. The system includes a flow diverter having a proximal end and a distal end. The flow diverter defines a flow channel extending therethrough. The flow diverter is at least partially contained within the lumen of the customizing member in a constrained configuration. The system includes a deployment wire extending into the lumen of the customizing member and into the flow channel of the flow diverter. The deployment wire has a proximal end, a distal end, and a distal wire portion having a taper. The deployment wire can include at least one deployment feature coupled to the flow diverter such that movement of the deployment wire relative to the customizing member moves the flow diverter relative to the customizing member. The deployment wire terminates in a proximal portion of the customizing member.

In some embodiments, the customizing member includes an introducer sheath having a proximal end and a distal end. In some embodiments, the introducer sheath is cuttable. In some embodiments, the flow diverter distally extends beyond a distal end of the introducer sheath. In some embodiments, the flow diverter is wholly contained within the customizing member.

In some embodiments, the customizing member further includes a tubing extending along and around a distal portion of the introducer sheath. In some embodiments, the flow diverter extends a first length beyond a distal end of the introducer sheath. In some embodiments, the tubing extends a second length beyond the distal end of the introducer sheath. In some embodiments, the distal end of the flow diverter is within the tubing, and in some embodiments the tubing is cuttable. In some embodiments, the tubing can be at least one of: a polymer tubing; a transparent tubing; or a semi-rigid tubing.

In some embodiments, the tubing can include graduation markings spaced along a distal end of the tubing. In some embodiments, the graduation markings are equally spaced along the distal end of the tubing.

In some embodiments, the introducer sheath can include an outer introducer sheath layer. In some embodiments, the customizing member further includes an inner tubing. In some embodiments, the inner tubing is cuttable. In some embodiments, the inner tubing is insertable into the outer introducer sheath layer. In some embodiments, the flow diverter is wholly contained within the inner tubing.

One aspect relates to a method for customizing a flow diverter for delivery into a neurovascular blood vessel to treat an aneurysm. The method includes determining a desired length of a flow diverter of a flow diverter system, and cutting a distal portion of the customizing member and the flow diverter such that the flow diverter is the desired length. The flow diverter system includes a customizing member having a proximal end and a distal end. The customizing member includes an interior wall defining a lumen. The flow diverter system includes a flow diverter including a proximal end and a distal end. The flow diverter defines a flow channel extending therethrough. The flow diverter is at least partially contained within the lumen of the customizing member in a constrained configuration. The flow diverter system includes a deployment wire extending into the lumen of the customizing member and into the flow channel of the flow diverter. The deployment wire having a proximal end, a distal end, and a distal wire portion having a taper. The deployment wire includes at least one deployment feature coupled to the flow diverter such that movement of the deployment wire relative to the customizing member moves the flow diverter relative to the customizing member. The deployment wire terminates in a proximal portion of the customizing member.

In some embodiments, the customizing member includes an introducer sheath having a proximal end and a distal end. In some embodiments, the customizing member further includes a tubing extending along and around a distal portion of the introducer sheath. In some embodiments, the flow diverter extends a first length beyond a distal end of the introducer sheath. In some embodiments, the tubing extends a second length beyond the distal end of the introducer sheath. In some embodiments, the distal end of the flow diverter is within the tubing. In some embodiments, the tubing is cuttable. In some embodiments, cutting the distal portion of the customizing member and the flow diverter includes cutting the tubing.

In some embodiments, the tubing includes graduation markings spaced along a distal end of the tubing. In some embodiments, cutting the tubing includes cutting the tubing at one of the graduation markings. In some embodiments, the flow diverter is fully retracted into the introducer sheath following the cutting by distally retracting the deployment wire.

In some embodiments, the method includes separating the tubing from the distal portion of the introducer sheath. In some embodiments, the tubing is separated from the distal portion of the introducer sheath after the flow diverter is retracted into the introducer sheath. In some embodiments, the tubing is separated from the distal portion of the introducer sheath by peeling the tubing from the distal portion of the introducer sheath. In some embodiments, the introducer sheath has an introducer length at least equal to a diverter length of the flow diverter.

In some embodiments, the tubing includes a proximal end, a distal end, a first longitudinal portion having a first proximal pull tab, and a second longitudinal portion having a second proximal pull tab. In some embodiments, each of the first longitudinal portion and the second longitudinal portion extend from the proximal end of the tubing to the distal end of the tubing. In some embodiments, the tubing is peelably removable from the distal portion of the introducer sheath by separating the first longitudinal portion from the second longitudinal portion.

The present disclosure relates to systems, devices, and methods for customizing a flow diverter for delivery into a neurovascular blood vessel to treat an aneurysm. Systems for customizing a flow diverter for delivery into a neurovascular blood vessel to treat an aneurysm include an elongate tubular member having a proximal end and a distal end. The elongate tubular member includes an interior wall defining a lumen. The system further includes a flow diverter including a proximal end and a distal end, where the flow diverter is partially contained within the lumen of the elongate tubular member in a constrained configuration and where the flow diverter extends a first length beyond the distal end of the elongate tubular member. The system further includes a deployment wire extending within the lumen of the elongate tubular member, the deployment wire having a proximal end, a distal end, and a distal portion having a taper. The deployment wire includes at least one deployment feature coupled to the flow diverter such that movement of the deployment wire relative to the elongate tubular member moves the flow diverter relative to the elongate tubular member. The system further includes a housing coupled to the elongate tubular member and defining a template for customizing the flow diverter.

The system may include that the deployment wire terminates in a proximal portion of the peelable tubing. The system may include that the elongate tubular member comprises an introducer sheath having a proximal end and a distal end, wherein the introducer sheath is cuttable.

The system may further include a tubing extending along and around a distal portion of the elongate tubular member, wherein the tubing extends a second length beyond the distal end of the elongate tubular member, wherein the distal end of the flow diverter is within the tubing, and wherein the tubing is cuttable. The system may include that the tubing is peelably removable from the distal portion of the elongate tubular member. The tubing may include a proximal end, a distal end, a first longitudinal portion having a first proximal pull tab, and a second longitudinal portion having a second proximal pull tab, each of the first longitudinal portion and the second longitudinal portion extending from the proximal end of the tubing to the distal end of the tubing, wherein the tubing is peelably removable from the distal portion of the elongate tubular member by separating the first longitudinal portion from the second longitudinal portion. The system may include that the flow diverter is cuttable within the tubing to a variable length.

The template may include equally spaced graduation markings where the graduation markings are configured to aid in cutting the flow diverter to a variable length. The template may further include a cutting aperture, slit, or notch extending through the housing where the cutting aperture, slit, or notch is disposed proximally of the graduation markings. The template may further include a cutting aperture extending through the housing where a width of the cutting aperture constrains a cutting tool to aid in cutting the flow diverter at a desired location or a desired angle. The template may further include an opening extending through the housing for retraction and advancement of the tubing relative to the graduation markings where the opening is disposed proximally of the cutting aperture. The template may further include an alignment member disposed below the graduation markings for guiding the flow diverter relative to the graduation markings and holding the flow diverter stationary during cutting. The template may correlate the graduation markings to a deployed length of the flow diverter. Advantageously, the health care professional is able to determine the desired length and customize the device to the desired length prior to inserting the device.

The at least one deployment feature may include a pusher extending along and around the distal portion of the deployment wire, the pusher having a distal end configured to engage with the proximal end of the flow diverter, at least one friction bump positioned along the distal portion of the deployment wire extending distally beyond the pusher, wherein the at least one friction bump is inside of the flow diverter and engaged with a portion of the flow diverter, and a tip coil extending distally from the at least one friction bump. The system may include that the flow diverter includes a self-expanding member having a proximal end and a distal end. The housing may be a packaging tray.

According to various embodiments, a method for customizing a flow diverter for delivery into a neurovascular blood vessel to treat an aneurysm includes providing a flow diverter delivery system. The system includes an elongate tubular member having a proximal end and a distal end. The elongate tubular member includes an interior wall defining a lumen. The system further includes a flow diverter including a proximal end and a distal end, where the flow diverter is partially contained within the lumen of the elongate tubular member in a constrained configuration and where the flow diverter extends a first length beyond the distal end of the elongate tubular member. The system further includes a deployment wire extending within the lumen of the elongate tubular member, the deployment wire having a proximal end, a distal end, and a distal portion having a taper. The deployment wire includes at least one deployment feature coupled to the flow diverter such that movement of the deployment wire relative to the elongate tubular member moves the flow diverter relative to the elongate tubular member. The system further includes a housing coupled to the elongate tubular member and defining a template for customizing the flow diverter. The system further includes a tubing extending along and around a distal portion of the elongate tubular member, wherein the tubing extends a second length beyond the distal end of the elongate tubular member, wherein the distal end of the flow diverter is within the tubing. The method includes determining a desired length of the flow diverter using the template, advancing or retracting the tubing relative to the housing to align the flow diverter to the template, cutting the tubing and the flow diverter such that the flow diverter is cut to the desired length, and retracting the flow diverter into the elongate tubular member or advancing the elongate tubular member over the flow diverter.

The method may include separating the tubing from the distal portion of the elongate tubular member after retracting the flow diverter into the elongate tubular member or advancing the elongate tubular member over the flow diverter. The method may include moving the deployment wire relative to the elongate tubular member such that the flow diverter moves relative to the elongate tubular member.

Advancing or retracting the tubing relative to the template may include positioning the flow diverter relative to graduation markings equally spaced along the template, wherein the graduation markings are configured to aid in cutting the flow diverter to the desired length. Advancing or retracting the tubing relative to the template may include positioning the tubing within an alignment member disposed below the graduation markings for guiding the flow diverter relative to the graduation markings. Advancing or retracting the tubing may include adjusting the tubing relative to the graduation markings via an opening extending through the housing and disposed proximally of the graduation markings.

Cutting the tubing and flow diverter may include using a cutting tool to cut the flow diverter at a desired location and/or at a desired angle via a cutting aperture, slit, or notch extending through the housing. The cutting aperture, slit, or notch may be positioned between the opening and the graduation markings and constrains the cutting tool during the cutting. The template may correlate the graduation markings to a deployed length of the flow diverter. Retracting the flow diverter into the elongate tubular member may include distally retracting the deployment wire. Advancing the elongate tubular member over the flow diverter may include holding the deployment wire stationary while advancing the elongate tubular member. Separating the tubing from the distal portion of the elongate tubular member may include peeling the tubing away from the distal portion of the elongate tubular member. The method may include that the deployment wire terminates in a proximal portion of the peelable tubing. The housing may include a packaging tray.

In one embodiment, a system for customizing a flow diverter for delivery into a neurovascular blood vessel to treat an aneurysm includes a customizing member including a proximal end and a distal end. The customizing member includes an interior wall defining a lumen. The system further includes a flow diverter comprising a proximal end and a distal end, the flow diverter defining a flow channel extending therethrough where the flow diverter is at least partially contained within the lumen of the customizing member in a constrained configuration. The system further includes a deployment wire extending into the lumen of the customizing member and into the flow channel of the flow diverter, the deployment wire having a proximal end, a distal end, and a distal wire portion having a taper, the deployment wire including at least one deployment feature coupled to the flow diverter such that movement of the deployment wire relative to the customizing member moves the flow diverter relative to the customizing member, the deployment wire terminating in a proximal portion of the customizing member. The system further includes a housing coupled to the customizing member and defining an integrated template for customizing the flow diverter. Various aspects of the present disclosure provide improved flexibility in flow diverter length selections, and specifically enable customization of flow diverter length. This customization decreases the number of SKUs that a hospital must keep in stock, decreases waste, and improves the likelihood of use of a properly-sized flow diverter.

The system may include various optional embodiments. The customizing member may include an introducer sheath having a proximal end and a distal end. The introducer sheath may be cuttable. The introducer sheath may include an outer introducer sheath layer and where the customizing member further comprises an inner tubing where the inner tubing is cuttable and where the inner tubing is insertable into the outer introducer sheath layer and where the flow diverter is wholly contained within the inner tubing. The flow diverter may distally extend beyond a distal end of the introducer sheath. The flow diverter may be wholly contained within the customizing member.

According to various embodiments of the system, the customizing member further may further include a tubing extending along and around a distal portion of the introducer sheath where the flow diverter extends a first length beyond a distal end of the introducer sheath, where the tubing extends a second length beyond the distal end of the introducer sheath, where the distal end of the flow diverter is within the tubing, and where the tubing is cuttable. The tubing may include a polymer tubing, a transparent tubing, or a semi-rigid tubing. The tubing may be peelably removable from the distal portion of the introducer sheath. The tubing may include a proximal end, a distal end, a first longitudinal portion having a first proximal pull tab, and a second longitudinal portion having a second proximal pull tab, each of the first longitudinal portion and the second longitudinal portion extending from the proximal end of the tubing to the distal end of the tubing, wherein the tubing is peelably removable from the distal portion of the introducer sheath by separating the first longitudinal portion from the second longitudinal portion.

According to at least some embodiments of the system, the flow diverter may be cuttable within the tubing to a variable length. The template may include equally spaced graduation markings where the graduation markings are configured to aid in cutting the flow diverter to a variable length. The template may include a cutting aperture, slit, or notch extending through the housing, wherein the cutting aperture, slit, or notch is disposed proximally of the graduation markings. The template may include a cutting aperture extending through the housing, wherein a width of the cutting aperture constrains a cutting tool to aid in cutting the flow diverter at a desired location or a desired angle. The template may include an opening extending through the housing for retraction and advancement of the tubing relative to the graduation markings, wherein the opening is disposed proximally of the cutting aperture. The template may include an alignment member disposed below the graduation markings for guiding the flow diverter relative to the graduation markings and holding the flow diverter stationary during cutting. The template may correlate the graduation markings to a deployed length of the flow diverter.

According to at least some embodiments of the system, the at least one deployment feature may include a pusher extending along and around the distal portion of the deployment wire, the pusher having a distal end configured to engage with the proximal end of the flow diverter, at least one friction bump positioned along the distal portion of the deployment wire extending distally beyond the pusher where the at least one friction bump is inside of the flow diverter and engaged with a portion of the flow diverter, and a tip coil extending distally from the at least one friction bump. The flow diverter may include a self-expanding member having a proximal end and a distal end. The housing may include a packaging tray.

Embodiments disclosed herein provide several beneficial improvements. These include, for example, a decrease in the size of the system. This decrease in size of the system enables the accessing and treating of smaller blood vessels. This increases range of treatable aneurysms, and thus improves patient outcomes. Further, embodiments disclosed herein improve flexibility of the system, thereby also increasing the range of treatable aneurysms.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 3 is a depiction of the flow diverter in a constrained delivery state.

FIG. 4 is a depiction of the flow diverter in an expanded deployed state.

FIG. 6 is an illustration of a flow diverter delivery system.

FIG. 7 is a depiction of the delivery system in a partially deployed configuration.

FIG. 12 is a depiction of the removal of the tubing after the flow diverter has been retracted into the sheath/catheter.

FIG. 13 is a depiction of one embodiment of a customizable flow diverter delivery system after the removal of the tubing.

FIG. 20 is an illustration of one embodiment of a customizable flow diverter delivery system.

FIG. 21 is an illustration of one embodiment of a customizable flow diverter delivery system.

FIG. 23 is an illustration of one embodiment of a customizable flow diverter delivery system.

FIG. 24 is an illustration of one embodiment of a customizable flow diverter delivery system.

DETAILED DESCRIPTION

Figure 1:
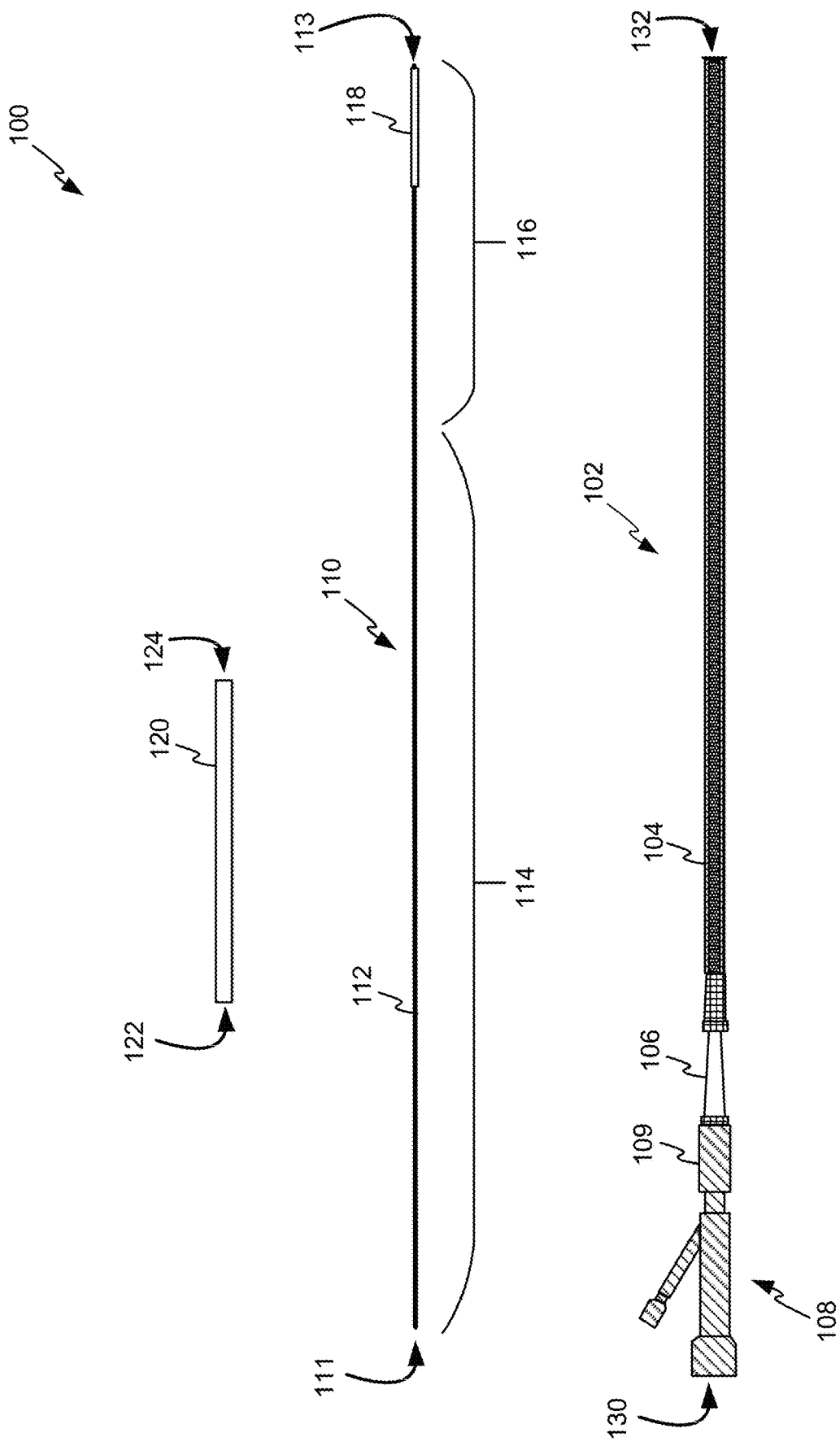
FIG. 1 is a depiction of one embodiment of a system for placement of a flow diverter.

The present relates to flow diverters, flow diverter delivery systems, and methods of delivering a flow diverter. A flow diverter is a device that can be placed within vasculature to divert flow away from portions of the vasculature covered by the flow diverter. As used herein, a flow diverter can be any device that is positionable within a patient's blood vessel and can divert a portion of the blood flow through that blood vessel. In some embodiments, a flow diverter can be an endovascular prosthesis used in treating intracranial aneurysms. A flow diverter can include, for example, a stent such as a laser cut stent, a braided member, or the like. In some embodiments, a flow diverter can comprise a braided member comprising a plurality of braided wires, which wires can be, for example, cobalt-chrome, Nitinol, or the like.

A flow diverter can be used to treat an intracranial aneurysm including, for example, saccular aneurysm and particularly an unerupted saccular aneurysm, or a fusiform shape or circumferential aneurysm. A flow diverter can be placed in a blood vessel to extend across and cover an aneurysm. The flow diverter can divert blood flow away from the aneurysm, thereby reducing blood flow in the aneurysm. Having reduced blood flow, over time, the aneurysm can close and heal.

While simple in principle, the reality of accurately placing a flow diverter in frequently small and tortuous vasculature of the brain can be very complicated. Accordingly, devices are desired that have high flexibility to enable the navigation of this vasculature. Further, such devices should be able to accurately position a flow diverter within a blood vessel. Accurately positioning of a flow diverter can include adjusting the position of the flow diverter, and in some embodiments can include, positioning multiple flow diverters to wholly or partially overlap. The use of multiple partial or wholly overlapping flow diverters can be of particular benefit in dealing with multiple closely spaced aneurysms or with a larger aneurysm. In some embodiments, multiple flow diverters can be positioned to wholly or partially overlap to further reduce blood flow to an aneurysm.

Neurovascular vessels have a wide range of lengths and diameters. Further, the diameter of a neurovascular vessel varies along its length, with the diameter normally decreasing at progressively distal locations of that neurovascular vessel. Hospitals must have varying lengths of flow diverters in supply to accommodate the different sizes neurovascular vessel, of side branches, and/or bifurcations. In addition, hospitals must stock flow diverters in various diameter sizes, resulting in a large number of SKUs to manage. Such a large and varied supply and stock system including the full range of sizes to optimally match flow diverter to a desired location becomes economically burdensome to maintain. Further, the need to have numerous different diameters and lengths of flow diverters complicates surgery, as the best fitting flow diverter must be placed in each location. To ensure a best fit, a surgeon must have flow diverters of the correct length and diameter in the operating room, which can lead to waste. Further, as flow diverters are provided a fixed lengths, a surgeon may be forced to use a flow diverter of a sub-optimal length. Various aspects of the present disclosure provide improved flexibility in flow diverter length selections, and specifically enable customization of flow diverter length. This customization decreases the number of SKUs that a hospital must keep in stock, decreases waste, and improves the likelihood of use of a properly-sized flow diverter.

Various embodiments of the present disclosure provide customizable flow diverter. Conventional designs provide a flow diverter packaged in an introducer sheath on a delivery system where a delivery wire extends past the implant, thereby fixing the length of the flow diverter. Embodiments disclosed herein do not have the deployment wire extending beyond the length of the flow diverter. Embodiments of the present disclosure provide a customizable system that allow users to tailor the length of the implant to match the specifications of the treatment site. Because the deployment wire does not extend distally beyond the distal end of the flow diverter, and terminates proximal to the distal end of the flow diverter, embodiments presented herein provide a delivery system where users can trim the flow diverter to a desired length without compromising the delivery system. Specifically, in some embodiments, users can trim the flow diverter at locations between where the deployment wire terminates and the distal end of the flow diverter. In some embodiments, the deployment wire terminates in a proximal portion of the flow diverter to thereby provide the user with the ability to trim the flow diverter in relatively distal portions of the flow diverter.

Furthermore, the presently disclosed customizable flow diverter delivery system advantageously includes deployment mechanisms which enable customization. For example, in conventional designs, deployment mechanisms are coupled to and/or are configured to be used with the aforementioned deployment wire which extends distally beyond the distal end of the flow diverter. Such mechanisms would prevent customization at the distal end of the flow diverter as there would not be any disposable material up to and including the distal end of the flow diverter. The presently disclosed customizable flow diverter delivery system overcomes these obstacles by providing a proximally located deployment wire and deployment mechanisms, leaving flexibility for adjusting the length of the distal end of the flow diverter.

Embodiments disclosed herein provide several beneficial improvements. These include, for example, a decrease in the size of the system. This decrease in size of the system enables the accessing and treating of smaller blood vessels.

This increases range of treatable aneurysms, and thus improves patient outcomes. Further, embodiments disclosed herein improve flexibility of the system, thereby also increasing the range of treatable aneurysms.

However, and despite the benefit of being able to customize the flow diverter, having a deployment wire that terminates inside of the flow diverter has drawbacks. Namely, the lack of the deployment wire extending beyond the distal end of the flow diverter during deployment of the flow diverter diminishes the ability of the deployment wire to effectively function as a guidewire to assist in the navigation of the vasculature. However, it has been found that the benefit of customizing the flow diverter outweighs the diminished control.

With reference now to FIG. 1 a depiction of one embodiment of a system 100 for placement of a flow diverter is shown. The system 100 can include a catheter system 102. The catheter system 102 can be configured to provide access to the patient's vasculature, and specifically to the patient's neurovasculature. In some embodiments, the catheter system 102 can be configured for insertion into the patient's vasculature at an access point, and for navigating through the patient's vasculature to a location at which the flow diverter is to be delivered.

The catheter system 102 can comprise a proximal end 130 and a distal end 132. The catheter system 102 can comprise an elongate catheter 104 defining a lumen extending through all or portions of the catheter 104. Accordingly, in some embodiments, the catheter system 102 can comprise an elongate tubular member defining a lumen, and specifically the elongate tubular member comprising an interior wall defining a lumen. The catheter 104 can comprises a variety of sizes, materials, and/or manufactures. In some embodiments, the catheter 104 can be flexible and can comprise a biocompatible material. The catheter 104 can comprise, for example, an elongate tubular member can have a diameter of, for example, 0.005 inches, 0.01 inches, 0.017 inches, 0.02 inches, 0.021 inches, 0.027 inches, 0.03 inches, or any other or intermediate diameter.

The catheter 104, which can include a catheter hub 106, can be coupled to an access device. The access device 108 can be a valve such as, for example, a rotating hemostasis valve (RHV) 109. The access device 108 can be a hemostasis valve that can be configured to provide selectable and/or controllable access to the lumen of the catheter 104. In some embodiments, the access device 108 can be configured to minimize blood loss while the catheter 104 is being used. The access device 108 can be sized for use in connection with the catheter 104.

The system 100 for placement of the flow diverter can include a deployment wire 110 comprising a proximal end 111 and a distal end 113. The deployment wire 110 can be configured to facilitate and/or control the advance of the flow diverter into and/or through the catheter system 102, and specifically into and/or through the lumen of the catheter 104. In some embodiments, the proximal end 111 of the deployment wire 110 is configured to be controlled to control the advance of the flow diverter into and/or through the catheter system 102, and the distal end 113 can be configured to be coupled to and/or to interact with the flow diverter to cause the flow diverter to advance into and/or through the catheter system 102.

The deployment wire 110 can comprise a core wire 112. The core wire 112 can comprise an elongate wire that can be flexible to enable navigation vasculature. In some embodiments, the core wire 112 can comprise a unibody reinforced delivery wire. The core wire 112 can comprise a variety of shapes and sizes and can be made from a variety of materials. The core wire 112 can comprise a biocompatible wire that can be, for example, a Nitinol wire.

The core wire 112 can, comprise a proximal portion 114 and a distal portion 116. Compared to the distal portion 116, the proximal portion 114 is relatively closer to the proximal end 111 of the deployment wire 110. Likewise, compared to the proximal portion 114, the distal portion is relatively closer to the distal end 113 of the deployment wire 110.

During a procedure, a distal end of the distal portion 116 can be first inserted into the patient. The core wire 112 can comprise a variety of shapes and sizes. In some embodiments, the core wire 112 can have a constant diameter along its length, and in some embodiments, the core wire 112 can have a non-constant diameter along its length. In some embodiments, the core wire 112 comprises a tapered core wire 112, which tapered core wire 112 comprises a portion having a decreased diameter. In some embodiments, the tapered portion can taper to a point, and in some embodiments, the tapered portion can taper to a flattened delivery tip. The tapered portion can be, all or portions of, for example, the distal portion 116 of the core wire 112. In some embodiments, the portion of the core wire 112 having a decreased diameter can be, for example, up to a distal 5% of the core wire 112, up to a distal 10% of the core wire 112, up to a distal 15% of the core wire 112, up to a distal 20% of the core wire 112, up to a distal 25% of the core wire 112, up to a distal 30% of the core wire 112, up to a distal 40% of the core wire 112, up to a distal 50% of the core wire 112, or any other or intermediate portion.

In some embodiments, for example, the core wire 112 can have a length that is as long as, or longer than the catheter system 102. The core wire 112 can have a maximum outer diameter of, for example, up: 0.1 inches; 0.05 inches, 0.04 inches, 0.03 inches, 0.02 inches, 0.015 inches, 0.01 inches, 0.005 inches, or any other or intermediate value.

The deployment wire 110 can include one or several deployment features 118. The deployment features 118 can be located on the distal portion 116 of the core wire 112. The deployment features 118 can comprise one or several features configured to interact with the flow diverter to enable the core wire 112 to control and/or manipulate the core wire 112. In some embodiments, the deployment features can be configured to enable the core wire 112 to interact with the flow diverter to push the flow diverter into and/or move the flow diverter in and/or through the lumen of the catheter 104. In some embodiments, the deployment features 118 can be configured to couple the flow diverter to the core wire 112 such that the flow diverter can be deployed from the catheter 104 into the patient. Details of the deployment features 118 will be discussed at greater length below.

The flow diverter placement system 100 can include an introducer sheath 120. The introducer sheath 120 can comprise an elongate tubular member having a proximal end 122 and a distal end 124. In some embodiments, each of the proximal end 122 and the distal end 124 of the introducer sheath 120 can be open. The introducer sheath 120 can comprising an interior wall defining a lumen extending through the introducer sheath 120.

Figure 2:
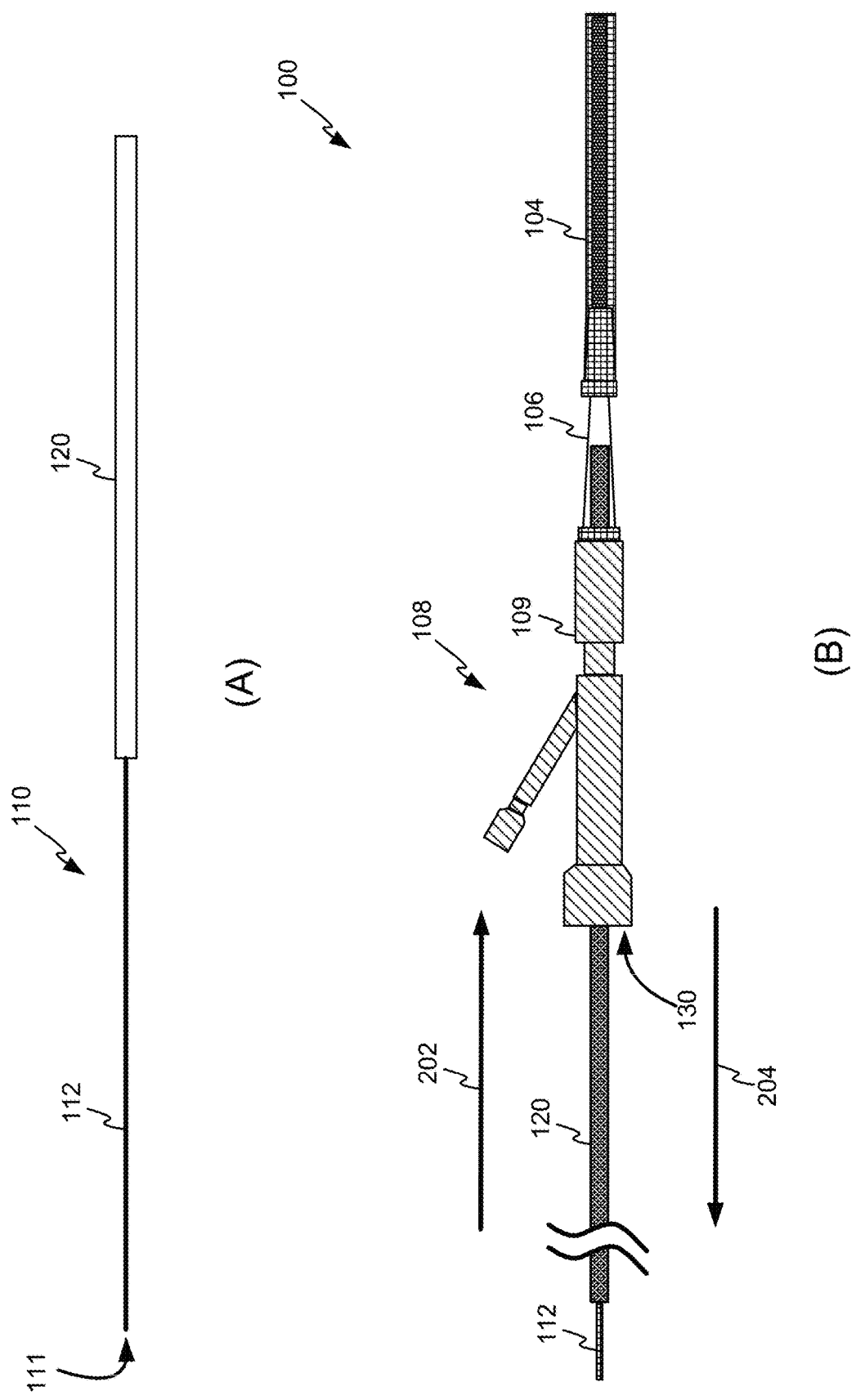
FIG. 2 is a depiction of the introducer sheath and the delivery of the flow diverter to the catheter via the introducer sheath.

The introducer sheath can be configured to hold the flow diverter before the flow diverter is inserted into the catheter system 102, and specifically into the proximal end 130 of the catheter system 102. In some embodiments, the introducer sheath 120 can be configured to hold the flow diverter in the lumen of the introducer sheath. In some embodiments, and as shown in FIG. 2(A), the introducer sheath 120 is holding the flow diverter in the lumen of the introducer sheath 120, and the deployment wire 110 is at least partially inserted into the lumen of the introducer sheath coupling the deployment features 118 of the deployment wire 110 with the flow diverter. As shown in FIG. 2(B), the introducer sheath 120, and specifically the distal end 124 of the introducer sheath 120 can be inserted into and through the access device 108 and into the catheter 104 and specifically into the catheter hub 106 of the catheter 104. In some embodiments, this can include inserting the combination of the introducer sheath containing the flow diverter and the deployment wire 110 into the catheter system 102 and specifically into the catheter 104.

In some embodiments, the introducer sheath 120 can be advanced through the access device 108 and into the catheter 104 in the direction indicated by arrow 202. The core wire 112 can inserted into the catheter system 102, and specifically into the proximal end 130 of the catheter system 102. In some embodiments, the core wire 112 can be inserted into the introducer sheath 120, which introducer sheath can be inserted into the catheter system 102.

The core wire 112 can be advanced in the direction indicated by arrow 202 through the introducer sheath 120 to advance the flow diverter from the introducer sheath 120 into the catheter 104. After the flow diverter is advanced into the catheter 104, the introducer sheath 120 can be retracted from the catheter 104 and from the access device 108 in the directed indicated by arrow 204.

With reference now to FIGS. 3 and 4, perspective view of an embodiment of a flow diverter 300 is shown. The flow diverter 300 can be, for example, a stent, a braided member, or the like. In some embodiments, a flow diverter can comprise an elongate braided member comprising a plurality of braided wires, which wires can be, for example, cobalt-chrome, Nitinol, or the like. The flow diverter 300 can, in some embodiments, comprise a tubular member defined by an external wall 302 having a first end 304, also referred to as a proximal end 304, and a second end 306, also referred to herein as a distal end 306. The flow diverter 300 can include a proximal portion 310 and a distal portion 312. In some embodiments, the proximal portion 310 can comprise a proximal half of the flow diverter 300 and the distal portion 312 can comprise a distal half of the flow diverter 300. In some embodiments, the proximal portion 310 can comprise, approximately, the most proximal third of the flow diverter 300 and the distal portion 312 can comprise the approximately two thirds of the flow diverter 300 distal to the proximal portion 310 of the flow diverter 300. In some embodiments, the proximal portion 310 can comprise, approximately, the most proximal quarter of the flow diverter 300 and the distal portion 312 can comprise the approximately three quarters of the flow diverter 300 distal to the proximal portion 310 of the flow diverter 300.

As seen in FIG. 4, the elongate tubular member of the flow diverter 300 can have a central axis 400 and can extend from a proximal end 402 to a distal end 404. A flow channel 406, also referred to herein as a diverter lumen 406, can be defined by an inner wall 403 of the flow diverter 300 and can extend along the central axis 400 and through the flow diverter 300. In some embodiments, each of the proximal end 402 and the distal end 404 can comprise an opening into the flow channel 406 such that fluid, and specifically blood can flow through the flow channel 406, flowing into the proximal end 402 and out the distal end 404.

The flow diverter 300 can be in a compressed state, also referred to herein as a constrained state, a delivery configuration, or as a constrained configuration as shown in FIG. 3, or can be in an expanded state, also referred to herein as an unconstrained stated and/or unconstrained configuration as shown in FIG. 4. In the constrained configuration, the flow diverter 300 can have a compressed outer diameter 308, in other words, cannot the flow diverter 300 in the constrained configuration is not fully expanded and/or is constrained so as not to be able to fully expand. In some embodiments, the flow diverter 300 can be held in the constrained state when the flow diverter is contained and/or constrained within the introducer sheath 120 and/or in the catheter 104. In some embodiments, the flow diverter can be sized to have a compressed outer diameter 308 that fits in the introducer sheath 120 and/or in the catheter.

In the unconstrained state, the flow diverter 300 can have an expanded outer diameter 408. The expanded diameter 408 can be larger than the compressed outer diameter 308. In some embodiments, the flow diverter 300 can be self-expanding such that when the flow diverter 300 exits the catheter 104 into a patient's blood vessel, the flow diverter 300 automatically expands to match the inner diameter of that blood vessel. In some embodiments, the flow diverter 300 can be made in a variety of sizes for use in blood vessels of different sizes. In some embodiments, the flow diverter 300 can have an expanded diameter 408 of up to 20 mm, up to 12 mm, up to 10 mm, up to 8 mm, up to 7 mm, up to 6 mm, up to 5 mm, up to 4 mm, between 0.5 mm and 10 mm, between 1 mm and 8 mm, between 1.25 mm and 6.5 mm, above 4.25 mm, or any other or intermediate diameter or range of diameters.

In some embodiments, the flow diverter 300 can have an undeployed length and a deployed length. In some embodiments, when the flow diverter 300 is deployed, the length of the flow diverter 300 can change due to the foreshortening of the flow diverter 300, which foreshortening can be related to the expansion of the flow diverter 300. Thus, the flow diverter 300 will experience relatively more foreshortening as the amount of expansion of the flow diverter 300 increases. In some embodiments, the flow diverter 300 can have a fully expanded length of less than approximately one-half of its constrained length, of between approximately one-third and one fourth of its constrained length, or any other or intermediate fully expanded length. Thus, in some embodiments, the flow diverter and have a foreshortening ratio of greater than approximately 2, of between approximately 3 and approximately 4, or any other or intermediate foreshortening ratio.

In some embodiments, the flow diverter 300 can have a constrained length of greater than approximately 10 mm, greater than approximately 15 mm, greater approximately 20 mm, greater than approximately 25 mm, greater than approximately 30 mm, greater than approximately 35 mm, of between approximately 10 mm and approximately 400 mm, of between approximately 25 mm and approximately 240 mm, or any other or intermediate length. In some embodiments, the flow diverter can have a deployed length of, for example, between approximately 5 mm and approximately 60 mm.

The flow diverter can be deployed into a patient's blood vessel through use of the system 100 of FIG. 1. The deployment can involve use of deployment features 118 of the deployment wire 110.

Figure 5:
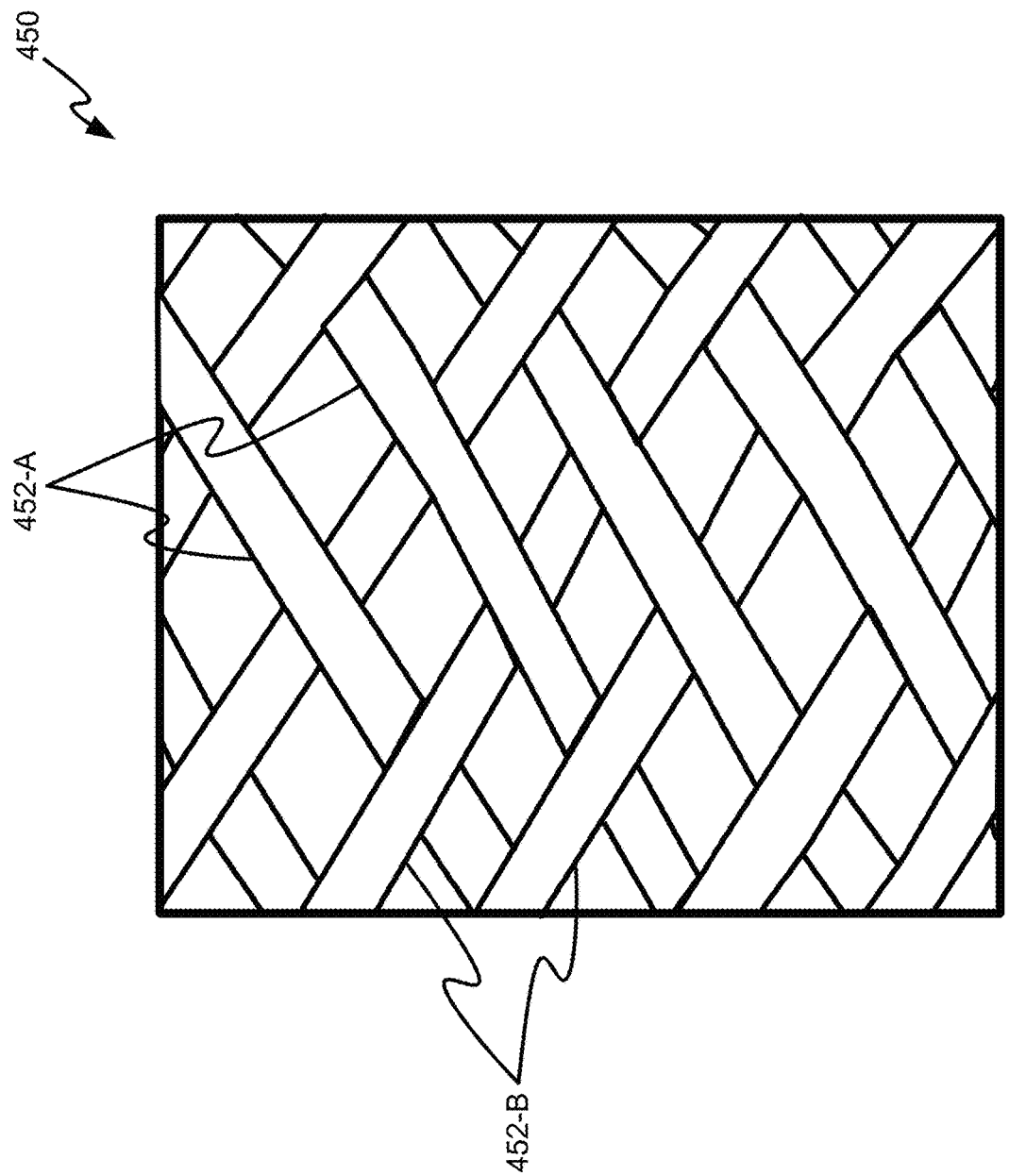
FIG. 5 is a close-up view of a braid of a flow diverter.

The flow diverter 300 can, in some embodiments, comprise a braided member. One embodiment of the braid of the flow diverter is depicted in 450, shown in detail in FIG. 5. As seen in FIG. 5, the braided member can be made from a plurality of wires 452, also referred to herein as strands 452. These wires 452 can comprise a variety of shapes and sizes and can be made from a variety of materials. In some embodiments, for example, the wires 452 can have a diameter of between approximately 0.0002 inches and approximately 0.01 inches, between approximately 0.0005 inches and approximately 0.005 inches, between approximately 0.0007 inches and approximately 0.002 inches, of approximately 0.0008 inches, of approximately 0.001 inches, of approximately 0.0012 inches, or any other or intermediate diameter.

In some embodiments, the wires 452 can comprise a variety of types and/or materials. In some embodiments, the wires 452 can comprise drawn filled tube (DFT). In some embodiments, the DFT can include an inner core and an outer tube. Each of the inner core and the outer tube can comprise a material, which can be a same material, or which can be different materials. In some embodiments, one or both of the inner core and the outer tube can be radiopaque. In some embodiments, for example, the outer tube can provide strength to the braided member of the flow diverter 300 and the inner core can be radiopaque.

In some embodiments, for example, the inner core can comprise platinum and/or a platinum alloy that can include, for example, platinum and tungsten. In some embodiment, the platinum alloy can comprise, for example, approximately 28% platinum. In some embodiments, the outer tube can comprise an alloy such as, for example, stainless teel, nitinol, cobalt chromium alloy such as 35N LT alloy, or the like.

In some embodiments, the wires can be cold worked, and specifically can have a minimum cold work of at least 30%, of at least 60%, of approximately 60.8%, or any other or intermediate amount of cold work. In some embodiments, the wires 452 can have a tensile strength minimum of at least approximately 50,000 PSI, of at least approximately 100,000 PSI, of at least 200,000 PSI, of approximately 235,000 PSI, of approximately 250,000 PSI, or any other or intermediate tensile strength minimum.

The braid of the flow diverter 300 can include any desired number of strands. In some embodiments, the braid of the flow diverter 300 can include between approximately 10 strands and approximately 200 strands, between approximately 20 strands and approximately 150 strands, between approximately 40 strands and approximately 100 strands, approximately 64 strands, or any other or intermediate number of strands. As seen in FIG. 5, the wires 452 can include wires 452-A extending in a first direction and braided with wires 452-B extending in a second direction. The wires 452 can be braided in any desired way including, for example, a 1 wire over 1 under 1 braid, a 1 wire over 2 under 2 braid as shown in FIG. 5, or any other braid.

With reference now to FIG. 6, a schematic illustration of a delivery system 500 is shown. The delivery system 500 can include a flow diverter 300 that can be held in a constrained configuration within a lumen 502 defined by an interior wall 504 of a catheter 104 or of an introducer sheath 120.

The lumen 502 can comprise a variety of shapes and sizes. In some embodiments, the lumen 502 can comprise a cylindrical lumen, and specifically can have a circular cross section. The size of the lumen 502 can, in some embodiments, be defined by an internal diameter. In some embodiments, the lumen 502 can have an internal diameter of, for example, up to: 0.2 inches, 0.1 inches; 0.05 inches, 0.04 inches, 0.03 inches, 0.025 inches, 0.021 inches, 0.02 inches, 0.017 inches, 0.015 inches, 0.01 inches, 0.005 inches, or any other or intermediate value.

The deployment wire 110 can extend at least partially into both the flow diverter 300 and the lumen 502 of the catheter 104 or of the introducer sheath 120. The deployment wire 110, can include the core wire 112 which can extend into the lumen 502 of the catheter 104 and/or of the introducer sheath 120, and the deployment features 118, which are shown wholly within the lumen 502 of the catheter 104 and/or of the introducer sheath 120.

In the embodiment shown in FIG. 6, the deployment features 118 include a pusher 505 such as a pusher coil 506 wrapping around a portion of the core wire 112, one or several friction bumps 508. These one or several friction bumps can include, for example, a first friction bump 508-A, a second friction bump 508-B, and third friction bump 508-C. In some embodiments, these one or several friction bumps 508 can comprises a plurality of friction bumps 508 can be distributed along a portion of the deployment wire 110, and specifically can be distributed along a portion of the core wire 112. In some embodiments, and as shown in FIG. 6, the friction bumps 508 can be positioned inside of the flow channel 406 of the flow diverter 300 and can engage with the flow diverter 300.

In some embodiments the number of friction bumps 508 in the deployment features 118 can vary based on the lengths of the flow diverter 300 being deployed by the deployment features 118, including the friction bumps 508. For example, as the length of the flow diverter 300 being deployed increases, the number of friction bumps 508 used in deploying the flow diverter 300 can increase. Thus, in an embodiment with a relatively shorter flow diverter 300, a relatively smaller number of friction bumps 508 can be used. Similarly, in an embodiment with a relatively longer flow diverter 300, a relatively larger number of friction bumps 508 can be included in the deployment features 118. In some embodiments, this variation of the number of friction bumps 508 with respect to the length of the flow diverter 300 can affect the length of the core wire 112 with respect to flow diverter 300, thereby leading to the termination of the core wire 112 within the flow channel 406 of the flow diverter 300.

In some embodiments, and by terminating in the flow channel 406 of the flow diverter 300, a portion of the flow diverter 300 distal to the termination of the deployment wire 110 can be trimmed without damaging the deployment wire 110 and/or the deployment features 118 of the deployment wire. In some embodiments, the deployment wire 110 can be sized and positioned relative to the flow diverter 300 such that the deployment wire 110 terminates in the proximal portion 310 of the flow diverter 300. In such an embodiment, the termination of the deployment wire 110 in the proximal portion 310 of the flow diverter 300 allows trimming of the distal portion 312 of the flow diverter 300 without damaging the deployment wire 110 and specifically without damaging the deployment features 118 of the deployment wire 110.

In some embodiments, the one or several friction bumps 508 can comprise a single friction bump. This single friction bump can, for example, extend from the pusher 505 to the position of the third friction bump 508-C of FIG. 6. Thus, instead of having multiple friction bumps 508 across this length of the core wire 112, and single friction bump 508, also referred to herein as a friction pad can extend across all or portions of this length of the core wire 112. In some embodiments, this single friction pad can extend beyond a proximal portion of the flow diverter 300 and into a distal portion of the flow diverter 300.

In some embodiments, a single, long friction pad can provide for better engagement with the flow diverter 300. However, embodiments with multiple, spaced-apart friction bumps can provide for improved flexibility of the core wire 112. In some embodiments, the single, long friction pad can comprise the same material as the friction bumps 508, and in some embodiments, the single, long friction pad can comprise a material configured to improve flexibility.

The deployment features 118 further include a support coil 510, also referred to herein as a supporting coil 510, wrapping around a portion of the core wire 112, and particularly winding around the distal portions of the core wire 112, which distal portions can be tapered. As seen in FIG. 3, the supporting coil 510 can extend at least partially through the pusher coil 506, and can extend along the core wire 112 between friction bumps 508 and distally beyond a final friction bump 508, or as shown in FIG. 3, beyond the third friction bump 508-C. Specifically, and as seen in FIG. 6, the support coil 510 can begin at a location between the proximal end 514 and the distal end 516 of the pusher 505 and/or of the pusher coil 506, and can distally extend to a location distally beyond the final friction bump 508. In such an embodiment, the support coil 510 can be intermediate between at least a portion of the pusher 505 and/or the pusher coil 506 and the core wire 112. The deployment features 118 can also include an atraumatic tip 512 at a distal most end of the deployment wire 110.

In some embodiments, for example, the deployment wire 110 and/or the core wire 112 can terminate within the flow diverter 300 when the flow diverter 300 is contained within the catheter 104 and/or the introducer sheath 120. For example, in the embodiment depicted in FIG. 6, the atraumatic tip 512 is located within the flow diverter 300 that is contained within the catheter 104 and/or the introducer sheath 120, and thus the deployment wire 110 and/or the core wire 112 terminates within the flow diverter 300 that is contained within the catheter 104 and/or the introducer sheath 120. In some embodiments, this can include the deployment wire 110 and/or the core wire 112 terminating at a location between the proximal end 304 and the distal end 306 of the flow diverter 300, and specifically can include the deployment wire 110 and/or core wire 112 terminating in the proximal portion 310 of the flow diverter 300.

In some embodiments, the deployment wire 110 and/or the core wire 112 can terminate within the flow diverter 300 when the flow diverter 300 is constrained, deployed, and/or partially deployed, for example, when the flow diverter 300 has a deployed diameter of at least approximately 2 mm, at least approximately 3 mm, at least approximately 4 mm, at least approximately 4.25 mm, at least approximately 5 mm, at least approximately 6 mm, or any other or intermediate deployed diameter. In some embodiments, the deployment wire 110 and/or the core wire 112 can terminate within the flow diverter 300 when the flow diverter 300 is constrained, deployed, and/or partially deployed when the flow diverter 300 has a constrained length of at least approximately 10 mm, of at least approximately 15 mm, of at least approximately 20 mm, of at least approximately 25 mm, of at least approximately 30 mm, of at least approximately 35 mm, or any other or intermediate length. In some embodiments, the deployment wire 110 and/or the core wire 112 can terminate within the flow diverter 300 when the flow diverter 300 is constrained, deployed, and/or partially deployed when the flow diverter 300 has at least one of a constrained length greater than approximately 25 mm of a deployed diameter of greater than approximately 4.25 mm.

In some embodiments, in which the deployment wire 110 and/or the core wire 112 does not extend distally beyond the distal end 306 of the flow diverter 300, the deployment wire 110 and/or core wire 112 can be sized and/or positioned with respect to the flow diverter 300 in the constrained configuration such that the deployment wire 110 and/or the core wire 112 terminate in the proximal portion 310 including the proximal half of the flow diverter 300, terminate in the proximal portion 310 including the most proximal third of the flow diverter 300, terminate in the proximal portion 310 including the most proximal quarter of the flow diverter 300, or terminate in any other or intermediate portion of the flow diverter 300. In some embodiments, this termination location for the deployment wire 110 and/or the core wire 112 can be determined based on the foreshortening ratio of the flow diverter 300.

In some embodiments, and as seen in FIG. 6, the deployment wire 110 and/or the core wire 112 has a length and/or position relative to the length of the flow diverter 300 such that the deployment wire 110 and/or the core wire 112, and specifically the distal end of the deployment wire 110 and/or the core wire 112 terminates within the flow diverter 300 when the flow diverter 300 is contained within the catheter 104 and/or the introducer sheath 120.

In some embodiments, the portion of the support coil 510 extending distally beyond the final friction bump 508 can support the flow diverter 300. Specifically, the portion of the support coil 510 extending distally beyond the final friction bump 508 can extend through at least a portion of the length of the flow diverter 300 and can, in some embodiments, strengthen those portions of the flow diverter 300. Specifically, and in some embodiments, the portion of the support coil 510 extending distally beyond the final friction bump 508 can prevent the flow diverter from collapsing and/or buckling.

The deployment wire 110, including the deployment features 118 can be configured for navigating a patient's vasculature, and specifically for navigating a patient's neurovasculature. Thus, in some embodiments, the deployment features 118 can be configured to facilitate and/or maintain flexibility of the core wire 112, and specifically of the distal portion 116 of the core wire 112.

The pusher coil 506 can be configured to apply a force to the flow diverter 300 when the deployment wire 110 is distally advanced into and/or through the catheter 104 and/or the introducer sheath 120. The pusher coil 506 can comprise a coil formed by wire winding. The wire forming the wire winding can comprise a variety of materials and sizes. In some embodiments, the wire forming the pusher coil 506 can comprise a biocompatible wire such as a Nitinol wire. The wire forming the pusher coil 506 can comprise a diameter of, for example, between 0 and 0.01 inches, between 0 and 0.005 inches, between 0 and 0.002 inches, approximately 0.002 inches, or any other or intermediate diameter.

The pusher coil 506 can have an outer diameter that is sized to fit in the lumen 502 of the catheter 104 and/or of the introducer sheath 120. In some embodiments, the pusher coil 506 can have a diameter that is less than the diameter of the lumen 502 of the catheter 104 and/or less than the inner diameter of the lumen of the introducer sheath 120. The outer diameter of the pusher coil can be sized with respect to the diameter of the lumen 502 of the catheter 104 and/or of the introducer sheath 120 such that flow diverter 300 does not fit between pusher coil 506 and the interior wall 504 of the catheter 104 and/or of the introducer sheath 120. In some embodiments in which the lumen 502 of the catheter 104 and/or of the introducer sheath 120 has an internal diameter of 0.017 inches, the pusher coil 506 can have an outer diameter of, for example, 0.015 inches. In some embodiments in which the lumen 502 of the catheter 104 and/or of the introducer sheath 120 has an internal diameter of 0.021 inches, the pusher coil 506 can have an outer diameter of, for example, 0.019 inches.

The pusher coil 506 can have a proximal end 514 and a distal end 516. In some embodiments, one or both of the proximal end 514 and the distal end 516 of the pusher coil 506 can be configured to affix the pusher coil 506 to the deployment wire 110. In some embodiments, one or both of the proximal end 514 and the distal end 516 of the pusher coil 506 can comprise solder affixing the pusher coil 506 to the deployment wire 110, or in other words, the pusher coil 506 can be soldered to the deployment wire 110. In some embodiments, the distal end 516 of the pusher coil 506 can be further configured to provide a bearing surface with which the pusher coil 506 can apply a force to the flow diverter 300. In some embodiments, the bearing surface can be formed in the solder of the distal end 516. In some embodiments, the distal end 516 of the pusher coil 506 can comprise a bumper portion configured to engage with the flow diverter 300. The bumper portion can be convex to better engage with the flow diverter 300. In some embodiments, the bumper portion can comprise a flattened tube.

The deployment features 118 can comprise one or several friction bumps 508. In some embodiments, a friction bump is configured to press a portion of the flow diverter 300 into the interior wall 504 of the catheter 104 and/or the introducer sheath 120 when that portion of the flow diverter 300 in within the catheter 104 and/or the introducer sheath 120. In some embodiments, the friction bump 508 can comprise a material that engages, and specifically that deformably engages, with the flow diverter 300 such that a friction force between the flow diverter 300 and the friction bump 508 is greater than a friction force between the flow diverter 300 and the interior wall 504 of the catheter 104 and/or introducer sheath 120. Due to the comparatively greater friction force between the friction bump 508 and the flow diverter 300, each friction bump 508 facilitates control of the flow diverter 300, and specifically facilitates control of the position of the flow diverter 300 with respect to the catheter 104 and/or introducer sheath 120. In some embodiments, the interaction between a friction bump 508 and the flow diverter 300 can enable the deployment wire 110 to deploy the flow diverter 300 from the catheter 104 and/or retract and/or partially retract a partially deployed flow diverter 300 back into the catheter 104.

The friction bump 508 can comprise, for example, a deformable material such as an elastomer. In some embodiments, the friction bumps 508 can comprise a polymer that can encase a radiopaque element such as, for example, a platinum coil and/or platinum wire. In some embodiments, the friction bumps 508 can comprise a tungsten loader polymer or a tungsten loaded elastomer. In some embodiments, the friction bumps can comprise a UV glue, which can be, for example, doped with a radiopaque material such as, for example, tantalum powder. In some embodiments some or all of the friction bumps 508 can be radiopaque and/or include a radiopaque element. In some embodiments, the radiopaque element can comprise one or several radiopaque particles embedded in the friction bump 508, and in some embodiments, and as shown in FIG. 6, the friction bump can comprise a radiopaque coil 509, which can comprise, for example, a piece of wire such as a coil of platinum wire.

In some embodiments in which the deployment wire 110 comprises a plurality of friction bumps 508, the friction bumps 508 can be equally or unequally spaced. In some embodiments, the friction bumps 508 can be spaced apart so as to be separated by between 1 mm and 20 mm, by between 1 mm and 15 mm, by between 2 mm and 10 mm, by between 3 mm and 8 mm, by approximately 5 mm, or by any other or intermediate value.

In some embodiments, the deployment features 118 can include support coil 510. Support coil 510 can prevent the core wire 112 from buckling when the core wire 112 is distally advancing the flow diverter 300 in the catheter 104 and/or in the introducer sheath 120. For example, to increase the flexibility of the core wire 112, the core wire 112 can taper at its distal portion 116. This taper can increase the flexibility of the core wire 112, but also decreases the strength of the core wire 112. This decrease in strength of the core wire 112 can result in the core wire 112 buckling when the core wire 112 is used to distally advance the flow diverter 300 in the catheter 103 and/or in the introducer sheath 120. The supporting coil 510 can extend along portions of the core wire 112 to prevent the core wire 112 from buckling. Thus, through the combination of the tapered core wire 112 and the support coil 510, the deployment wire 110 can be flexible to navigate tortuous vasculature while also having sufficient strength to deploy the flow diverter 300.

As seen in FIG. 6, the support coil 510 can extend over portions of the core wire 112, and specifically over all or portions of the distal portion 116 of the core wire 112. As further seen in FIG. 6, the support coil 510 can extend over the core wire 112 between the friction bumps 508, and distally beyond the last friction bump 508, or more specifically, distally beyond the third friction bump 508-C.

The wire forming the support coil can comprise a diameter of, for example, between 0 and 0.01 inches, between 0 and 0.005 inches, between 0 and 0.002 inches, approximately 0.002 inches, or any other or intermediate diameter. In some embodiments, the wire forming the support coil 510 can have the same diameter as the wire forming the pusher coil 506, and in some embodiments, the wire forming the support coil 510 can have a different diameter than the wire forming the pusher coil 506. In some embodiments, the supporting coil 510 can have an outer diameter of, for example, up to 0.04 inches, up to 0.03 inches, up to 0.02 inches, up to 0.015 inches, up to 0.01 inches, up to 0.005 inches, up to 0.001 inches, or any other or intermediate value.

The deployment wire 110 can extend distally beyond the friction bumps 508, and in some embodiments, distally beyond the third friction bump 508-C. The deployment wire 110 can terminate with an atraumatic tip 512 that can be located at the distal end of the deployment wire 110. In some embodiments, the portion of the deployment wire 110 extending distally beyond the friction bump 508 can include a portion of the support coil 510. The atraumatic tip 512 can be configured to not damage tissue it may be bumped into during the performing of a procedure, and specifically during the deploying of a flow diverter 300 in a patient's vasculature. The atraumatic tip 512 can be attached to the distal end of the core wire 112 and/or to the distal end of the support coil 510. The atraumatic tip can have a diameter matching the outer diameter of the supporting coil 510. In some embodiments, the atraumatic tip 512 can be spaced apart from the last friction bump 508 by between 1 mm and 20 mm, by between 1 mm and 15 mm, by between 2 mm and 10 mm, by between 3 mm and 8 mm, by approximately 5 mm, or by any other or intermediate value.

In some embodiments, the delivery system, and as shown in FIG. 6, the delivery system 500 can include a retraction sleeve 520. The retraction sleeve 520 can be coupled to the deployment wire 110 and can extend over a proximal portion 522 of the flow diverter 300. In some embodiments, the retraction sleeve 520 can extend over the proximal portion 522 of the flow diverter 300 when the flow diverter 300 is contained within the introducer sheath 120 and/or the catheter 104. In some embodiments, the retraction sleeve 520 can extend some or all of the length of the deployment features 118, and thus can extend over some or all of the proximal portion 522 of the flow diverter 300 engaging with the deployment features 118.

In some embodiments the retraction sleeve 520 can be positioned intermediate between the proximal portion 522 of the flow diverter 300 and the introducer sheath 120 and/or the catheter 104 and can thereby reduce friction between the proximal portion 522 of the flow diverter 300 and the introducer sheath 120 and/or the catheter 104. In some embodiments, the retraction sleeve 520 can not only decrease friction between the proximal portion 522 of the flow diverter 300 and the introducer sheath 120 and/or the catheter 104, but can also protect the proximal portion 522 of the flow diverter from damage that may arise from movement of the flow diverter 300 with respect to the introducer sheath 120 and/or the catheter 104 such as can occur during the deployment and/or retraction of the flow diverter 300.

The retraction sleeve 520 can comprise a flexible polymer that can be coupled to the deployment wire 110. In some embodiments, the retraction sleeve 520 can be coupled to the deployment wire 110 at a position distal of all or portions of the deployment features 118, as shown in FIG. 6. In some embodiments, the retraction sleeve 520 can comprise a heat-shrink polymer tube that can be positioned over the proximal portion 522 of the flow diverter 300 and over a portion of the deployment wire 110 distal of the flow diverter 300. The retraction sleeve 520 can then be heat-shrunk around the flow diverter 300 to snugly fit around the flow diverter 300.

The retraction sleeve 520 can further include one or more slits extending proximally from a distal end of the retraction sleeve 520. The one or more slits separate the portion of the retraction sleeve 520 extending over the proximal portion 522 of the flow diverter 300 into a plurality of segments. For example, in an embodiment of the retraction sleeve 520 containing two slits, the retraction sleeve 520 can be divided into two pieces, which can be two equal halves. The one or more slits can allow the retraction sleeve 520 to open and separate from the flow diverter 300 as the flow diverter 300 is deployed. Thus, as seen in FIG. 7, as the retraction sleeve 520 protrudes distally beyond the catheter 104. As seen the retraction sleeve 520 extending distally beyond the catheter 104 has split and separated from the flow diverter 300, allowing the flow diverter 300 to expand, and allowing the retraction of the retraction sleeve 520 into the catheter 104 upon full deployment of the flow diverter 300.

With reference now to FIG. 7, a schematic depiction of the delivery system 500 in a partially deployed configuration is shown. As seen in FIG. 7, the catheter 104 containing the deployment wire 110 and the flow diverter 300 is in a blood vessel 600. As further seen in FIG. 7, the deployment wire 110 has been distally advanced, as indicated by arrow 602, with respect to the catheter 104, thereby partially deploying the flow diverter 300. The combination of the friction bumps 508 and the pusher coil 506 engage with the flow diverter 300 to cause the flow diverter 300 to distally advance in and out of the catheter 104 when the deployment wire 110 is distally advanced. As the deployment wire 110 is distally advanced, the flow diverter 300 deploys from the catheter 104 and begins to expand. This distal advance continues until the flow diverter 300 is fully deployed. Alternatively, if the flow diverter 300 has not been fully deployed from the catheter 104, and in the event that at least one of the friction bumps 508 is still within the catheter 104 and engaging with the flow diverter 300, the flow diverter 300 can be retracted and/or partially retracted into the catheter 104. In some embodiments, a successful deployment of a flow diverter 300 can be achieved by only distally advancing the deployment wire 110, and in some embodiments, a successful deployment of the flow diverter 300 can be achieved by alternatingly distally advancing and proximally retracting the flow diverter 300 until a desired positioning and/or deployment is achieved.

Figure 8:
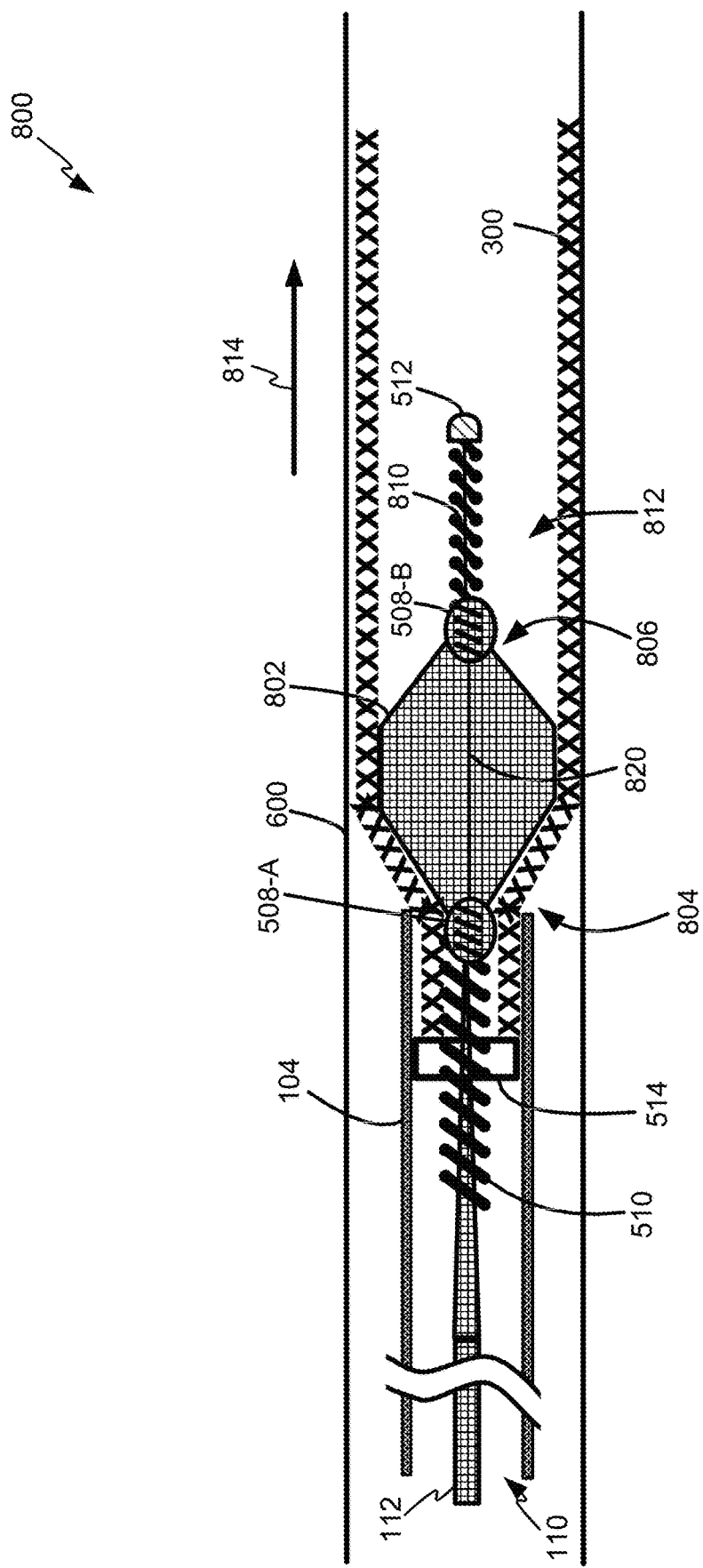
FIG. 8 is a depiction of the delivery system in a partially deployed configuration.

With reference now to FIG. 8, a schematic depiction of one embodiment of a dynamic delivery system 800 is shown. The system 800 can include a flow diverter 300 that can be held in a constrained state within the lumen 502 of the catheter 104 and/or of an introducer sheath 120. In some embodiments, the flow diverter 300 can comprise an expandable, braided member that can define a flow channel 406. In some embodiments, the flow diverter 300 can comprise a self-expanding braided member.

The flow diverter 300 can be positioned in a lumen 502 of the catheter 104 and/or of the introducer sheath 120. In some embodiments, the flow diverter 300 can be positioned in a lumen 502 of the catheter 104 and/or of the introducer sheath 120 circumferentially between the interior wall 504 defining the lumen 502 of the catheter 104 and/or of the introducer sheath 120 and the expanding element, which can be a self-expanding element, discussed at greater length below.

The deployment wire 110 can extend at least partially into both the flow diverter 300 and the lumen 502 of the catheter 104 or of the introducer sheath 120. The deployment wire 110, can include the core wire 112 which can extend into the lumen 502 of the catheter 104 and/or of the introducer sheath 120, and the deployment features 118, which are shown wholly within the lumen 502 of the catheter 104 and/or of the introducer sheath 120. The deployment features 118 are coupled to the flow diverter such that movement of the deployment wire 110 and/or of the core wire 112 with respect to the catheter 104 and/or the introducer sheath 120 likewise moves the flow diverter 300 relative to the catheter 104 and/or the introducer sheath 120.

In some embodiments, and as depicted in FIG. 8, the deployment wire 110 and the core wire 112 terminate within the flow channel of the flow diverter 300, in other words, do not extend distally beyond the distal end of the flow diverter 300. In some embodiments, the deployment wire 110 and/or the core wire 112 are sized and/or configured such that neither the deployment wire 110 nor the core wire 112 extends distally beyond the distal end 306 of the flow diverter 300 when the flow diverter 300 is in the constrained configuration, or in the unconstrained configuration after being deployed from the catheter 104. Thus, the atraumatic tip 512 at the distal end of the deployment wire 110 is located within the flow diverter 300 and not distally beyond the distal end 306 of the flow diverter 300.

The deployment features 118 include one or more friction bumps 508, the supporting coil 510, a pusher 514, an expanding element 802, a tip coil 810, and an atraumatic tip 512. The tip coil can be a flexible tip coil 810. In some embodiments, the flexible tip coil 810 and/or the flexible tip coil 810 and the atraumatic tip 512 can facilitate in navigating the system 800 and/or the core wire 112 through the vasculature, and specifically through tortuous vasculature.

In some embodiments, some or all of these deployment features 118 engage with, or as shown in FIG. 8, are engaged with the flow diverter 300. The deployment features 118 are engage and/or can be engaged with the flow diverter 300 such that movement of the core wire 112 results in corresponding movement of the flow diverter 300.

The expanding element 802 can comprise a self-expanding element 802 or a controlled expanding element. In some embodiments, the self-expanding element 802 can expand upon exiting the catheter 104. In some embodiments, the controlled expanding element can expand when controlled to expand. The controlled expanding element can comprise, for example, a stent, a braid, a balloon, or the like. In some embodiments in which the expanding element 802 comprises a braided member, the thickness of the stands of the braid can be varied to achieve a desired effect. For example, the strands can be thicker to provide increased expansion force, or the stands can be thinner to provide increased flexibility. In some embodiments, the strands can comprise a variety of material including, for example, DFT, which can be, for example, radiopaque. In some embodiments, the strands can comprise a polymer such as a high tensile strength polymer. In some embodiments, a polymer used in the strands can advantageously increase friction between the expanding element 802 and the flow diverter 300, thereby increasing the ability of the expanding element 802 to retract the flow diverter 300. In embodiments in which the stands comprise a polymer, that polymer can be treated and/or doped to be radiopaque.

In some embodiments, the materials of the flow diverter 300 and/or the expanding element 802 can be selected to minimize a compressed diameter of the flow diverter 300 around the expanding element 802. In some embodiments, for example, the selection and use of a high tensile strength material, such as a material having a tensile strength at or above 100 kpsi, 150 kpsi, 200 kpsi, 250 kpsi, or the like, the fully compressed expanding element 802 can have an outer diameter, for example, between approximately 0.005 inches and 0.035 inches, between approximately 0.01 inches and 0.015 inches, of approximately 0.013 inches, or any other or intermediate outer diameter. In such an embodiment, when the flow diverter 300 is axially positioned around and over the expanding element 802, the combination of the expanding element 802 and the flow diverter 300, both in a compressed state can have an outer diameter of between, for example, approximately 0.01 inches 0.04 inches, between approximately 0.015 inches and 0.035 inches, an outer diameter of approximately 0.017 inches, or any other or intermediate outer diameter. As used herein, "approximately" indicates values falling within: +/−5% of the associated value, +/−10% of the associated value, and/or +/−20% of the associated value. Thus, the combination of the flow diverter 300 and the expanding element 802 can fit in a catheter 104 having an inner diameter between, for example, approximately 0.01 inches and 0.04 inches, between approximately 0.015 inches and 0.035 inches, of approximately 0.017 inches, or any other or intermediate inner diameter.

In some embodiments, the controlled expanding element can include one or several features configured to enable control of the expansion of the controlled expanding element. These features can include one or several wires, catheters, rods, or the like. In some embodiments, the controlled expanding element can be expanded by bring axially compressing the controlled expanding element such that a proximal end of the controlled expanding element is brought closer to a distal end of the controlled expanding element. While the following discussion focuses on use of the self-expanding element 802, it will be appreciated that the self-expanding element 802 can be replaced with the controlled expanding element.

As shown in FIG. 8, the self-expanding element 802 comprises a proximal end 804, also referred to herein as a first end 804, and a distal end 806, also referred to herein as a second end 806. The proximal end 804 of the self-expanding element 802 can be coupled to the distal end 113 of the deployment wire 110, and more specifically to the distal end 113 of the core wire 112. The self-expanding element 802 can, as shown in FIG. 8, distally extend from the proximal end 804 to the distal end 806 of the self-expanding element 802.

The self-expanding element 802 can comprise a stent or a braided member. In some embodiments, the self-expanding element comprises a laser cut stent. The self-expanding element 802 can comprise a variety of shapes and sizes and can be made from a variety of materials. In some embodiments, the self-expanding element 802 can be made from Nitinol, a drawn filled tube which can comprise, for example, Nitinol, a cobalt chromium exterior and a platinum interior, a mixture of, for example, Nitinol and cobalt chromium, or the like. In some embodiments, the self-expanding element 802 can comprise a plurality of braided strands, at least some of which can be radiopaque.

The self-expanding element 802 can be configured to engage with the flow diverter 300 when the flow diverter is contained within the catheter 104 and/or in the introducer sheath 120 such that movement of the deployment wire 110, and specifically of the core wire 112, results in corresponding movement of the flow diverter 300. When the self-expanding element 802 has deployed from the catheter 104, the self-expanding element 802 expands to a fully expanded state, or to a maximum expanded state allowed by the blood vessel in which the self-expanding element 802 is contained. In some embodiments, the self-expanding element 802 can be distally advanced and/or proximally retracted through the flow diverter 300.

In some embodiments, the expanding element 802, such as the controlled expanding element or the self-expanding element 802 can generate radial forces which can expand the flow diverter 300 to a greater degree than would otherwise occur. For example, even if the flow diverter 300 is self-expanding, the expanding element 802 such as the controlled expanding element or the self-expanding element 802 may generate greater radial, expansive forces than generated by the flow diverter 300. By moving the expanding element 802 through the flow diverter 300, these greater radial, expansive forces generated by the expanding element 802 can be applied to the flow diverter 300 and can further expand the flow diverter 300. This increased expansion can increase and/or improve the contact between the flow diverter 300 and the blood vessel 600. In some embodiments, the use of an expanding element 802 such as the controlled expanding element or as the self-expanding element.

In some embodiments, the expanding element 802, when unconstrained, can have a diameter greater than a diameter of the unconstrained flow diverter 300, and in some embodiments, the expanding element 802, when unconstrained, can have a diameter less than a diameter of the unconstrained flow diverter 300. Thus, in some embodiments, and when unconstrained, the expanding element 802 can have a diameter greater than, or less than the diameter of the blood vessel 600. In some embodiments, when deploying a flow diverter 300, kinks, twists, compression, or bends can occur in the flow diverter 300, which can prevent the expansion of the flow diverter 300. In some embodiments, the expanding element 802 can straighten, remedy, and/or eliminate these kinks, twists, compression, or bends in the flow diverter 300 by expanding to a diameter less than the diameter of the blood vessel 600. In such an embodiment, an expansion by the expanding element 802 of less than the diameter of the blood vessel 600 can straighten, remedy, and/or eliminate these kinks, twists, compression, or bends in the flow diverter 300, which can result in the flow diverter 300 self-expanding to engage with the wall of the blood vessel 600. In such an embodiment, while the expanding element 802 may not force the flow diverter 300 to expand to engage with the wall of the blood vessel, the expanding element 802 can force the flow diverter 300 to expand sufficiently to eliminate, straighten, and/or remedy these kinks, twists, compression, or bends in the flow diverter 300 such that the flow diverter 300 can self-expand to engage with the wall of the blood vessel 600. Thus, in some embodiments, the expanding element 802 initiates expansion, which is then continued and completed by the flow diverter 300.

Alternatively, in some embodiments, the diameter of the expanding element 802 can be such that the movement of the expanding element 802 through the deployed flow diverter 300 forces the deployed flow diverter 300 to expand to engage with the wall of the blood vessel 600. In such an embodiment, the expanding element 802 can expand to a diameter that is equal to and/or greater than the diameter of the blood vessel 600.

In some embodiments, the expansion of the expanding element 802 can result in the shortening of the expanding element 802. This shortening can move the distal end 113 of the core wire 112 proximally. This can specifically move the atraumatic tip 512 proximally. This proximal movement of the distal end 113 of the core wire 112 and/or of the atraumatic tip 512 can decrease the distal extension of those portions of the core wire 112 into the blood vessel, thereby decreasing the risk of damage to the blood vessel.

The one or more friction bump 508 can be coupled to the deployment wire 110, and specifically can be coupled to the core wire 112 and/or to the support coil 510. In some embodiments, the one or more friction bumps 508 can be directly coupled to the deployment wire 110 and specifically to the core wire 112, and in some embodiments, the one or more friction bumps 508 can be indirectly coupled to the deployment wire 110 and specifically to the core wire 112 via, for example, the self-expanding element. In some embodiments, the friction bumps 508 can be coupled directly to the support coil 510. In some embodiments, the friction bump 508 can be soldered to the supporting coil 510, which solder can infiltrate the supporting coil 510 can further couple the friction bump 508 to the core wire 112.

In some embodiments, one or more friction bumps 508 can be located at one or both of the ends of the self-expanding element. Thus, in some embodiments, at least one of the friction bumps 508 is located at one of the proximal end 804 and the distal end 806. In some embodiments, at least one of the friction bumps 508 is located at one of the proximal end 804 and the distal end 806, and another of the friction bumps is located at the other of the proximal end 804 and the distal end 806. As seen in FIG. 8, the friction bumps 508 include a first friction bump 508-A located at, adjacent to, and/or on the proximal end 804 of the self-expanding element 802, and a second friction bump 508-B located at, adjacent to, and/or on the distal end 806 of the self-expanding element 802. In some embodiments, the friction bump 508 can extend across and/or over a portion of the self-expanding element 802. In some embodiments, one or more of the friction bumps 508 can be radiopaque, and/or can include a radiopaque element such as a wire coil 509. In some embodiments, the expanding element 802, and/or one or both of the friction bumps 508 can facilitate in retracting a partially deployed flow diverter 300 wholly or partially into the catheter 104. In some embodiments, the first friction bump 508-A, due to its relatively most proximal position, can best facilitate retraction of the flow diverter 300 wholly or partially into the catheter 104 as compared to the relatively more distally located expanding element 802 and the second friction bump 508-B.

In some embodiments, the first friction bump 508-A can be coupled to the proximal end 804 of the expanding element 802 and/or to the distal end of the core wire 112. In some embodiments, the first friction bump 508-A can be coupled to supporting coil 510. Specifically, in some embodiments, the first friction bump 508-A can directly couple to the supporting coil 510. In some embodiments, the first friction bump 508-A can be soldered to the supporting coil 510, which solder can infiltrate the supporting coil 510 and can further couple the first friction bump 508-A to the core wire 112 and specifically to the distal end of the core wire 112. In some embodiments, this solder can form all or portions of the first friction bump 508-A.

In some embodiments, the second friction bump 508-B can be coupled to the distal end 806 of the expanding element 802 and/or to the tip coil 810. In some embodiments, the second friction bump 508-B can be soldered to the distal end 806 of the expanding element 802 and/or to the tip coil 810. In some embodiments, this solder can form all or portions of the second friction bump 508-B.

The system can include a support coil 510. The support coil 510 can extend around and/or along at least part of the distal portion 116 of the core wire 112, including, along and/or around the distal end 113 of the core wire 112. The support coil 510 can, in some embodiments, extend from a location proximal of the self-expanding element 802 to the self-expanding element 802, and/or from a location proximal to the first friction bump 508-A to the first friction bump 508-A. In some embodiments, the support coil 510 can extend at least partially into the first friction bump 508-A.

In some embodiments, the core wire 112 terminates at and/or in the first friction bump 508-B. Thus, in some embodiments, the distal end 806 of the expanding element 802 does not directly couple to a distal end of the core wire 112, but rather is indirectly coupled to the distal end of the core wire 112 via the proximal end 804 of the expanding element 802. Thus, in some embodiments, the core wire 112 does not extend through the expanding element 802. In some embodiments, this coupling of only the proximal end 804 of the expanding element 802 to the core wire 112 allows the expanding element 802 to shorten in connection with the radial expansion of the expanding element 802. In some embodiments, the absence of the core wire 112 extending through the expanding element 802 increases the flexibility of the expanding element 802.

In some embodiments in which the core wire 112 terminates at the proximal end 804 of the expanding element 802, a coupling wire 820 can connect to the distal end 806 of the expanding element 802, to the tip coil 810, and/or to the atraumatic tip 512. In some embodiments, the coupling wire 820 can be configured to prevent loss of distal portions of the deployment wire 110 in the event that, for example, the expanding element 802, the tip coil 810, and/or the atraumatic tip 512 break. In such an embodiment, the coupling wire 820 enables retraction of the distal portions of the deployment wire 110 from the patient.

In some embodiments, the coupling wire 820 can connect to the distal end of the core wire 112, and in some embodiments, the coupling wire 820 can extend parallel and/or through the core wire 112, and can, in some embodiments, be used as a pull wire to control expansion and/or to facilitate expansion of the expanding element 802.

In some embodiments, the coupling wire 820 can be taught when the expanding element 802 is contained within the catheter 104 and/or in the introducer sheath 120, and the coupling wire 820 can be slack when the expanding element 802 is deployed from the catheter 104 and/or is in the expanded configuration.

The system 800 can, in some embodiments, include a tip coil 810, which can be a flexible tip coil 810. The tip coil 810 can distally extend from the self-expanding element 802, and specifically can distally extend from the distal end 806 of the self-expanding element 802. The tip coil 810 can extend distally beyond the self-expanding element 802 and can terminate in an atraumatic tip 512. The atraumatic tip 512 can, in some embodiments, be at the distal most point of the tip coil 810. In some embodiments, the flexible tip coil 810 and/or the flexible tip coil 810 and the atraumatic tip 512 can facilitate in navigating the system 800 and/or the core wire 112 through the vasculature, and specifically through tortuous vasculature.

An embodiment of the deployment of the flow diverter with the system 800 is shown in FIG. 8. The catheter 104 has been inserted into the vascular system and has been advanced to a location proximate to a treatment site 812, which location can be at, near, or beyond the treatment site 812. In some embodiments, the position of the catheter can be determined via imaging, such as via fluoroscopy.

As seen in that figure, the deployment wire 110 and the flow diverter 300 are distally advanced in the direction indicated by arrow 814 until the flow diverter 300 exits the catheter 104. As the flow diverter 300 exits the catheter 104, the flow diverter 300 can begin to expand and can begin to engage the interior of the blood vessel 600. In some embodiments, the distal advance of the deployment wire 110 and the flow diverter 300 can continue until the flow diverter 300 is fully deployed. Alternatively, if the flow diverter 300 has not been fully deployed from the catheter 104, the flow diverter 300 can be retracted and/or partially retracted into the catheter 104. In some embodiments, the flow diverter 300 can be retracted and/or partially retracted into the catheter 104 until the proximal most of the friction bumps 508 and/or the self-expanding element 802 exits the catheter 104. In some embodiments, the position of the flow diverter 300, of the catheter 104, of the friction bumps 508 and/or the self-expanding element 802 can be determined via imaging, and specifically via imaging of radiopaque elements and/or portions of the catheter 104, of the friction bumps 508, and/or the self-expanding element 802. In some embodiments, and based on the results of this imaging, it can be determined if the flow diverter 300 can be retracted and/or partially retracted into the catheter 104.

When the self-expanding element 802 exits the catheter 104, the self-expanding element 802 expands and applies radially outward forces to the flow diverter 300 causing the flow diverter 300 to further expand. Alternatively, in the event that a controlled expanding element is being used, open exiting the catheter 104, the controlled expanding element can be expanded.

The self-expanding element 802 can continue to be distally advanced relative to the catheter 104 until the flow diverter 300 is fully deployed. When the flow diverter 300 is fully deployed, the self-expanding element 802 can be distally advanced through the flow diverter 300 to fully and/or maximally expand the flow diverter 300, at which point the self-expanding element 802 can be proximally retracted through the flow diverter 300 and then back into the catheter 104. In some embodiments, the distal advance and the proximal retraction of the expanding element 802 through the flow diverter 300 can be repeated multiple times before retracting the expanding element 802 into the catheter 104. In some embodiments, the repeated movement of the expanding element 802 through the deployed flow diverter 300 can facilitate in achieving full deployment of the flow diverter 300, specifically in the event that all or portions of the flow diverter 300 have not fully deployed. This movement of the self-expanding element 802, first distally and then proximally through the flow diverter 300 can increase the expansion of the flow diverter 300 and improve the connection between the flow diverter and the blood vessel 600.

Once the self-expanding element 802 has been retracted into the catheter 104, the catheter can be retracted and/or one or several additional flow diverters can be delivered to the treatment site.

As shown in FIG. 8, a graphical depiction of an embodiment of delivering a flow diverter 300, and specifically for delivery a flow diverter 300 into a blood vessel 600 to treat an aneurysm is shown. In some embodiments, the blood vessel can be a neurovascular blood vessel, or in other words, can be a blood vessel in or around the patient's brain. In some embodiments, the delivery of the flow diverter 300 into the blood vessel 600 can include the partial deployment of the flow diverter 300 from a catheter 104, and/or the full or partial retraction of the flow diverter 300 into the catheter 104. As used herein, a full retraction occurs when the flow diverter 300 is retracted until it is completely contained with the catheter 104, and a partial retraction occurs when a portion of the flow diverter 300 remains exterior to the catheter 104 after retraction of the flow diverter 300.

In some embodiments, the flow diverter can be fully or partially deployed subsequent to the retraction of the flow diverter 300 into the catheter 104. In some embodiments, the flow diverter 300 can be partially deployed and retracted once, and in some embodiments, the flow diverter 300 can be repeatedly partially deployed and retracted into the catheter 104.

In some embodiments, the flow diverter 300 can be retracted into the catheter 104 and removed from the blood vessel. In some embodiments, the flow diverter 300 can be replaced with another flow diverter 300 of a different size, such as, for example, a flow diverter having a larger or a smaller diameter. In some embodiments, the flow diverter 300 can be retracted and redeployed to improve expansion of the flow diverter 300. In some embodiments, for example, a retracting and redeploying the flow diverter 300 can result in a more complete opening of the flow diverter 300, and/or improved contact between all or portions of the flow diverter 300 and the blood vessel in which it is deployed.

In some embodiments, the flow diverter 300 can be retracted and/or redeployed to affect the portion of the blood vessel covered by the deployed flow diverter 300. In some embodiments, for example, and by controlling a position and/or movement of both the catheter 104 and the core wire 112 during deployment, the coverage of the flow diverter 300 of the blood vessel in the treatment location can be affected. For example, and after a distal portion of the flow diverter 300 has engaged with the blood vessel, thereby coupling the flow diverter 300 to the blood vessel, the length of the deployed flow diverter can be affected by retracting the catheter 104 while deploying the flow diverter 300. Specifically, the relative speed of the retraction of the catheter 104 with respect to the deployment of the flow diverter 300 can affect the length of the flow diverter 300. For example, by retracting the catheter 104 relatively slowly with respect to the deployment of the flow diverter 300, the length of the deployed flow diverter can be decreased. Alternatively, by retracting the catheter 104 relatively quickly with respect to the deployment of the flow diverter 300, the flow diverter 300 can be stretched while being deployed and the length of the deployed flow diverter 300 can be increased.

In some embodiments, and by controlling the length of the deployed flow diverter 300, the surgeon can affect the diameter of the deployed flow diverter 300. Specifically, as the length of the deployed flow diverter increases, the deployed, unconstrained diameter of the flow diverter decreases. Thus, in some embodiments in which a flow diverter 300 is deployed into a blood vessel having a larger diameter, the surgeon may decrease the length of the deployed flow diverter to achieve the desired deployed diameter of the flow diverter 300.

Figure 9:
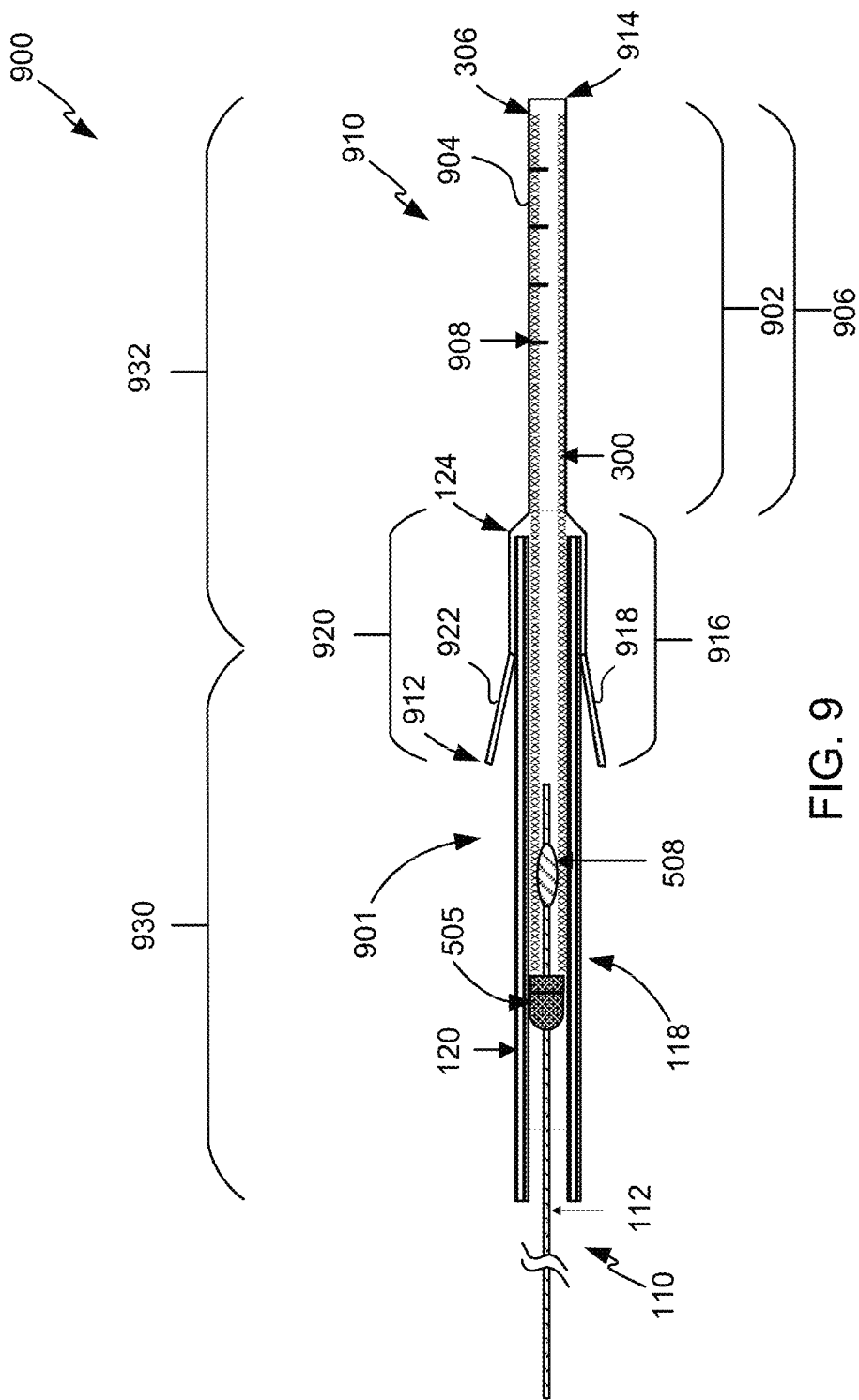
FIG. 9 is an illustration of one embodiment of customizable flow diverter delivery system.

With reference now to FIG. 9, a schematic depiction of a customizable delivery system 900 is shown. As seen in FIG. 9, the deployment wire 110 and the flow diverter 300 are positioned at least partially within the introducer sheath 120. As seen in FIG. 9, in some embodiments, no portion of the deployment wire 110 extends distally beyond the distal end 307 of the flow diverter 300. As further seen in FIG. 9, in some embodiments, no portion of the deployment wire 110 extends distally beyond the distal end 124 of the introducer sheath 120 before the flow diverter 300 is customized.

As further seen in FIG. 9, the deployment wire 110 including the tapered core wire 112 is coupled deployment features 118, which, as shown in FIG. 9, include the pusher 505 and the friction bump 508 as described in detail above. Although FIGS. 9 through 16 depict embodiments with the friction bump 508 and/or the pusher 505, these embodiments could include the deployment features 118 depicted in FIG. 8, specifically, for example, the expanding element 802 and the friction bumps 508-A, 508-B.

The combination of the friction bump 508 and the pusher 505 engage with the flow diverter 300 to cause the flow diverter 300 to distally advance in and out of the catheter 104 when the deployment wire 110 is distally advanced. As the deployment wire 110 is distally advanced, the flow diverter 300 deploys from the catheter 104 and begins to expand. This distal advance continues until the flow diverter 300 is fully deployed. Alternatively, if the flow diverter 300 has not been fully deployed from the catheter 104, and in the event that the friction bump 508 is still within the catheter 104 and engaging with the flow diverter 300, the flow diverter 300 can be retracted and/or partially retracted into the catheter 104. In some embodiments, a successful deployment of a flow diverter 300 can be achieved by only distally advancing the deployment wire 110, and in some embodiments, a successful deployment of the flow diverter 300 can be achieved by alternatingly distally advancing and proximally retracting the flow diverter 300 until a desired positioning and/or deployment is achieved. According to system 900 as shown in FIG. 9, the flow diverter 300 extends a first length 902 beyond the distal end 124 of the introducer sheath 120.

The system 900 as shown in FIG. 9 further includes a customizing member 901 that can allow the customizing of the flow diverter 300. The customizing member 901 can, in some embodiments, allow customizing of the flow diverter 300 before insertion of the flow diverter 300 into the catheter 104.

The customizing member 901 can comprise an elongate tubular member having a proximal end and a distal end. In some embodiments, the elongate tubular member of the customizing member 901 comprises an interior wall defining a lumen. In some embodiments, the customizing member 901 can include one or several cuttable portions that allow cutting, and thereby customizing of the flow diverter 300.

The customizing member 901 can include a proximal portion 930 and a distal portion 932. In some embodiments, the proximal portion 930 can comprise a proximal half of the customizing member 901 and the distal portion 932 can comprise a distal half of the customizing member 901. In some embodiments, the proximal portion 930 can comprise, approximately, the most proximal third of the customizing member 901 and the distal portion 932 can comprise the approximately two thirds of the customizing member 901 distal to the proximal portion 930 of the customizing member 901. In some embodiments, the proximal portion 930 can comprise, approximately, the most proximal quarter of the customizing member 901 and the distal portion 932 can comprise the approximately three quarters of the customizing member 901 distal to the proximal portion 930 of the customizing member 901.

In some embodiments, the customizing member 901 can include one or several components. The customizing member 901 can include the introducer sheath 120. In some embodiments, the introducer sheath 120 can be cuttable to customize the flow diverter 300. In some embodiments, the customizing member 901 can include the introducer sheath 120 coupled and/or coupleable to another feature which is cuttable for customization of the flow diverter 300. In some embodiments, for example, the customizing member 901 can include a tubular member such as the introducer sheath 120 and a cuttable support which extends along and around the distal end 124 of the elongate tubular member (e.g., the introducer sheath 120). In some embodiments, the cutable support can be a tubing 904 which extends along and around the distal end 124 of the elongate tubular member (e.g., the introducer sheath 120). The tubing 904 may be a polymeric tubing attached to the distal end 306 of the flow diverter 300. The tubing 904 preferably comprises a polymer tubing including heat shrinkable PTFE, Pebax, Polyolefin, FEP. In at least some embodiments, the tubing 904 is transparent, partially transparent, or opaque. For example, in at least some approaches, the flow diverter 300 is visible or partially visible within the tubing 904.

In some embodiments, and as depicted in FIGS. 9 through 17, the deployment features 118 and/or the deployment wire 110 do not distally extend into the tubing 904, but rather terminate in the introducer sheath 120. In some embodiments, the deployment features and/or the deployment wire 110 terminate in a proximal portion 930 of the customizing member 901. Thus, in some embodiments, the deployment features terminate in the proximal portion 310 of the flow diverter 300 which proximal portion of the flow diverter 300 is contained in the introducer sheath 120 and not in the tubing 904.

The tubing 904 extends a second length 906 beyond the distal end 124 of the introducer sheath 120. As seen in FIG. 9, the distal end 306 of the flow diverter 300 can be contained within the tubing 904. The tubing 904 is preferably cuttable and configured to enable customization of the length of the flow diverter 300 via cutting of the tubing 904 and the therein contained flow diverter 300. In at least some embodiments, the tubing is semi-rigid and peelable.

In at least some approaches, the first length 902 and the second length 906 are equal such that the flow diverter 300 and the tubing 904 distally extend the same length beyond the distal end 124 of the introducer sheath 120. In other approaches, the second length 906 (e.g., the length the tubing 904 extends beyond the distal end 124 of the introducer sheath 120) may be more or less than the first length 902 (e.g., the length the flow diverter 300 extends beyond the distal end 124 of the introducer sheath 120). In at least some embodiments, the deployment wire 110 terminates before the distal end 306 of the flow diverter 300 such that the distal end of the deployment wire 110 does not extend into the tubing 904. The deployment wire 110 does not extend distally beyond the distal end 306 of the flow diverter 300.

In some embodiments, the flow diverter 300 is cuttable within the tubing 904 to a desired length. Specifically, in some embodiments, the combination of the dimensions and composition of the individual strands in the flow diverter 300 and the weave of the braid can make the flow diverter 300 cuttable. In some embodiments, this can include, for example, a weave of the braid that does not unravel when the flow diverter 300 is cut. The heat shrink tubing restrains the braid and maintains the braid in a constrained configuration. In various approaches, the braid has been heat treated to maintain its shape and tubular configuration.

Via cutting of the flow diverter 300, the desired length of the flow diverter 300 may be customizable such that a physician tailors the length of the flow diverter 300 to match the specifications of the treatment site. For example, the physician may trim the flow diverter 300 within the tubing 904 to a desired length without compromising the delivery system 900. The tubing 904 aids the flow diverter 300 trimming-on-demand process.

In at least some embodiments, the tubing 904 comprises graduation markings 908 equally spaced along a portion of the tubing 904, and specifically along a distal portion 910 of the tubing 904. In various embodiments, the flow diverter 300 may include graduation markings 908 equally spaced along a portion of the flow diverter 300 in a manner such that the graduation markings 908 are visible through the tubing 904. The graduation markings 908 may be used as a ruler for guiding the cutting of the flow diverter 300 and/or the tubing 904 to the desired length.

The tubing 904 comprises a proximal end 912 and a distal end 914 opposite the proximal end 912, a first longitudinal portion 916 have a first proximal pull tab 918, and a second longitudinal portion 920 having a second proximal pull tab 922. In some embodiments, the first longitudinal portion 916 is coupled to the second longitudinal portion 920 via a coupling portion, which coupling portion is relatively thinner than each of the first longitudinal portion 916 and the second longitudinal portion 920. Each of the first longitudinal portion 916 and the second longitudinal portion 920 extend from the proximal end 912 of the tubing 904. In various embodiments, the tubing 904 is peelably removable from the distal portion of the introducer sheath 120 by separating the first longitudinal portion 916 from the second longitudinal portion 920, using the first proximal pull tab 918 and the second proximal pull tab 922, in a manner which would be understood by one having ordinary skill in the art. Specifically, in some embodiments, the peeling of the tubing 904 from the introducer sheath can include the separating of the first longitudinal portion 916 from the second longitudinal portion 920 along the coupling portion.

Figure 10:
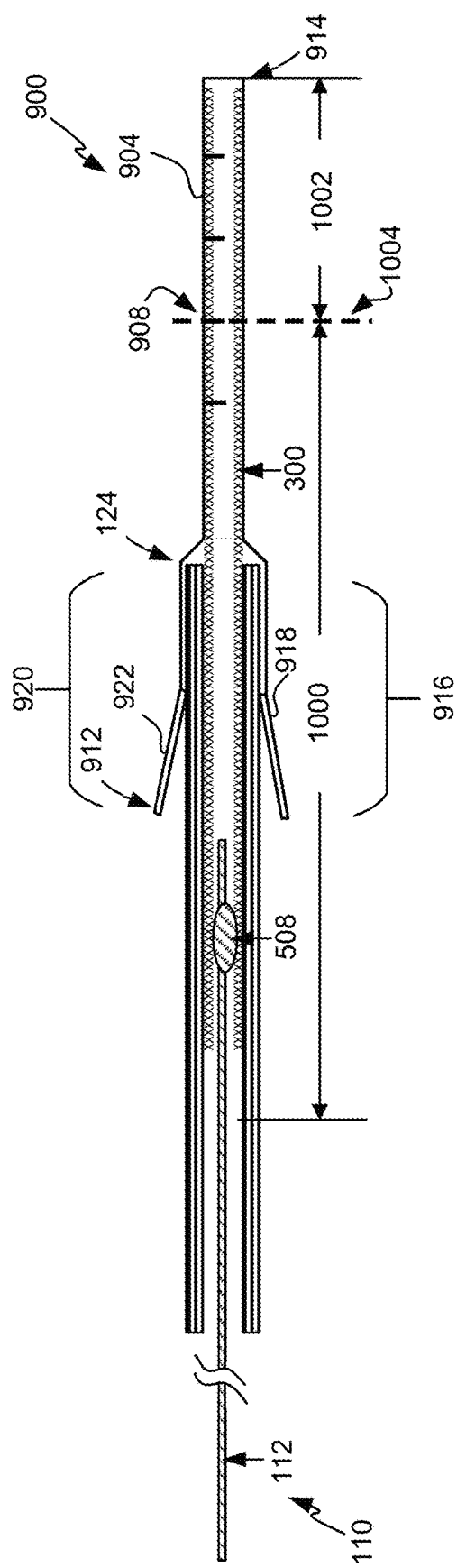
FIG. 10 is a depiction of a desired length in one embodiment of a customizable flow diverter delivery system.
Figure 11:
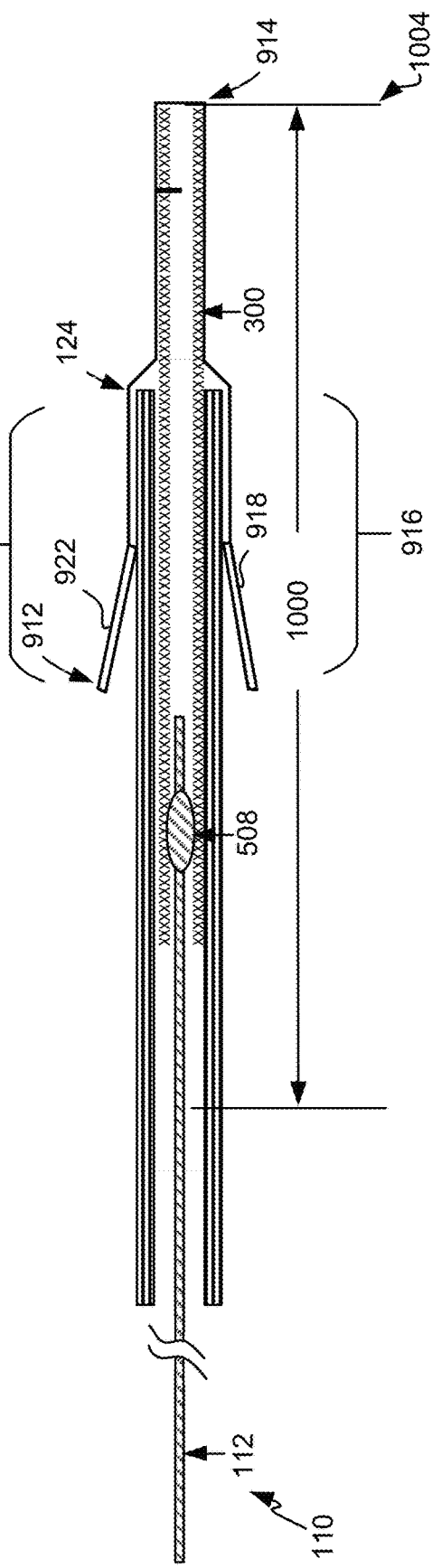
FIG. 11 is a depiction of one embodiment of a customizable flow diverter delivery system after the tubing and the flow diverter have been cut to the desired length.

As shown in FIG. 10, the system 900 may be used to customize the length of the flow diverter 300 to a desired length 1000. In at least some embodiments, a discarded section 1002 may be removed (e.g., cut) from the tubing 904 having the flow diverter 300 located within the tubing 904. The graduation markings 908 may be used to measure the desired length 1000 and/or the discarded section 1002 to determine where a cut 1004 should be made. Referring now to FIG. 11, the discarded section 1002 has been removed and the desired length 1000 remains.

As shown in FIG. 12, the tubing 904 first longitudinal portion 916 having a first proximal pull tab 918 and second longitudinal portion 920 having a second proximal pull tab 922 can be peelably removed from the distal portion of the introducer sheath 120 by separating the first longitudinal portion 916 from the second longitudinal portion 920, using the first proximal pull tab 918 and the second proximal pull tab 922, in a manner which would be understood by one having ordinary skill in the art. For example, the first longitudinal portion 916 is pulled by the pull tab 918 in a first direction 1200 generally perpendicular to a longitudinal axis 1202 of the introducer sheath 120. Similarly, the second longitudinal portion 920 is pulled by the pull tab 922 in a second direction 1204 generally perpendicular to a longitudinal axis 1202 of the introducer sheath 120 and opposite from the first direction 1200.

In at least some embodiments, the desired length 1000 of the flow diverter 300 is retracted into the introducer sheath 120 such that the flow diverter 300 is substantially within the introducer sheath 120, prior to or during the peelable removal of the tubing 904. In some embodiments, the introducer sheath 120 has a length such that the entire flow diverter 300 can be retracted from the tubing 904 into the introducer sheath 120 whether the flow diverter 300 is trimmed or untrimmed. In some such embodiments, the introducer sheath 120 has a length greater than or equal to the length of the untrimmed flow diverter 300. Thus, in some embodiments the combined length of the introducer sheath 120 with the attached tubing is longer than the untrimmed flow diverter. The flow diverter 300 can be retracted into the introducer sheath 120 via actuation of the deployment wire 110 and movement relative to the introducer sheath 120, in a manner described in detail above. For example, retracting the flow diverter 300 into the introducer sheath 120 is performed by distally retracting the deployment wire 110.

Pealably removing the tubing 904 includes separating the tubing 904 from the distal portion of the introducer sheath 120. The tubing 904 may be separated from the distal portion of the introducer sheath 120 by peeling the tubing 904 from the distal portion of the introducer sheath 120 as described above where peeling the tubing 904 includes separating the first longitudinal portion 916 from the second longitudinal portion 920, however, separating the tubing 904 from the distal portion of the introducer sheath 120 may be performed in other ways, such as, for example, only one pull tab is used to separate the tubing 904. In some approaches, the tubing 904 is separated from the distal portion of the introducer sheath 120 after the flow diverter 300 is retracted into the introducer sheath.

Figure 14:
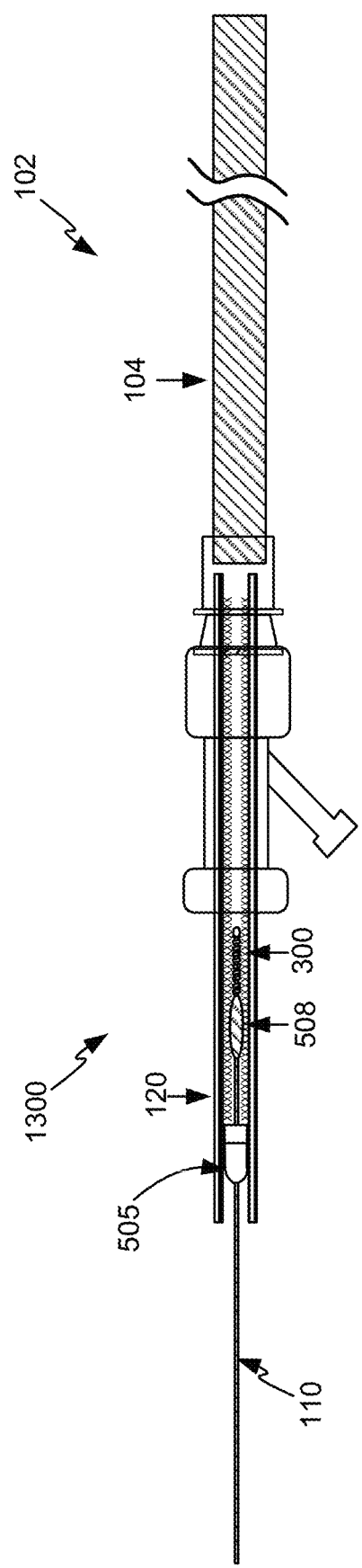
FIG. 14 is a depiction of an introducer sheath and the delivery of the flow diverter to the catheter via the introducer sheath.

Referring now to FIG. 13, after the tubing 904 is peelably removed from the distal portion of the introducer sheath 120 and the desired length 1000 of the flow diverter 300 is retracted into the introducer sheath 120, the remaining system 1300 may be loaded into the catheter system 102, and specifically into the catheter 104 of the catheter system 102 via actuation of the deployment wire 110 as shown in FIG. 14. The flow diverter 300 can then be delivered to a neurovascular vessel (e.g., blood vessel 600). This can include moving a distal end 132 of the catheter system 102 proximate to a treatment location, for example, advancing the catheter system 102 proximal to a treatment location within a neurovascular blood vessel, advancing a core wire through the microcatheter, and deploying the flow diverter from the microcatheter and into the neurovascular blood vessel 600 to treat an aneurysm by advancing the pusher and the at least on friction bump via advancement of the core wire.

In some embodiments, the catheter system 102 can be positioned distal, and in some embodiments, just distal of the treatment location. In some embodiments, the distal advance of the deployment wire 110 with respect to the catheter system 102 can likewise cause the flow diverter 300 to distally advance with respect to the catheter system 102. In some embodiments, the flow diverter 300 can be deployed by advancing the deployment wire 110 with respect to the catheter system 102. In some embodiments, this advancing of the deployment wire 110 with respect to the catheter system 102 can include retracting the catheter system 102 in the blood vessel 600 while maintaining the position of the deployment wire 110 with respect to the blood vessel 600, advancing the deployment wire 110 with respect to the blood vessel 600 while maintaining the position of the catheter system 102 with respect to the blood vessel 600, or simultaneously retracting the catheter system 102 with respect to the blood vessel 600 while advancing the deployment wire 110 with respect to the blood vessel 600.

In some embodiments, the flow diverter 300 expands and/or begins to expand as the flow diverter 300 exits the catheter system 102. The flow diverter 300 can continue to be deployed via the further distal advance of the deployment wire 110 and thus of the flow diverter, and the flow diverter 300 can be fully deployed.

After the flow diverter 300 has been fully deployed, the deployment wire 110 can be distally retracted into the catheter system 102, and the catheter can be retracted from the treatment location, and from the patient's vasculature. In some embodiments, one or several additional flow diverters 300 can be deployed to the treatment location. This can include placing an additional flow diverter on top of one or several previously deployed flow diverter 300. Alternatively, one or several additional flow diverters 300 can be placed to be partially overlapping to increase the length of treated blood vessel 600. In such an embodiment, a distal end of an additional flow diverter can be overlappingly placed over the proximal end or a previously placed flow diverter 300.

In some embodiments, at least one of the pusher and the at least one friction bump is radiopaque. Delivery of the catheter system 102 may include imaging the at least one of the pusher and the at least one friction bump to determine a position of the flow diverter in the neurovascular blood vessel and a position of the pusher and/or the at least one friction bump with respect to the microcatheter.

In some embodiments, the flow diverter is retracted into the microcatheter when at least one of the at least one friction bump has not exited the microcatheter. In at least some aspects, the positioning of the microcatheter is adjusted with respect to the treatment location based on the imaging.

In various aspects, the flow diverter is loaded into the catheter system 102. In some embodiments, loading the flow diverter into the microcatheter includes inserting an introducer sheath containing the flow diverter through an access device into the microcatheter, and advancing the deployment wire through the introducer sheath to advance the flow diverter from the introducer sheath into the microcatheter.

Figure 15:
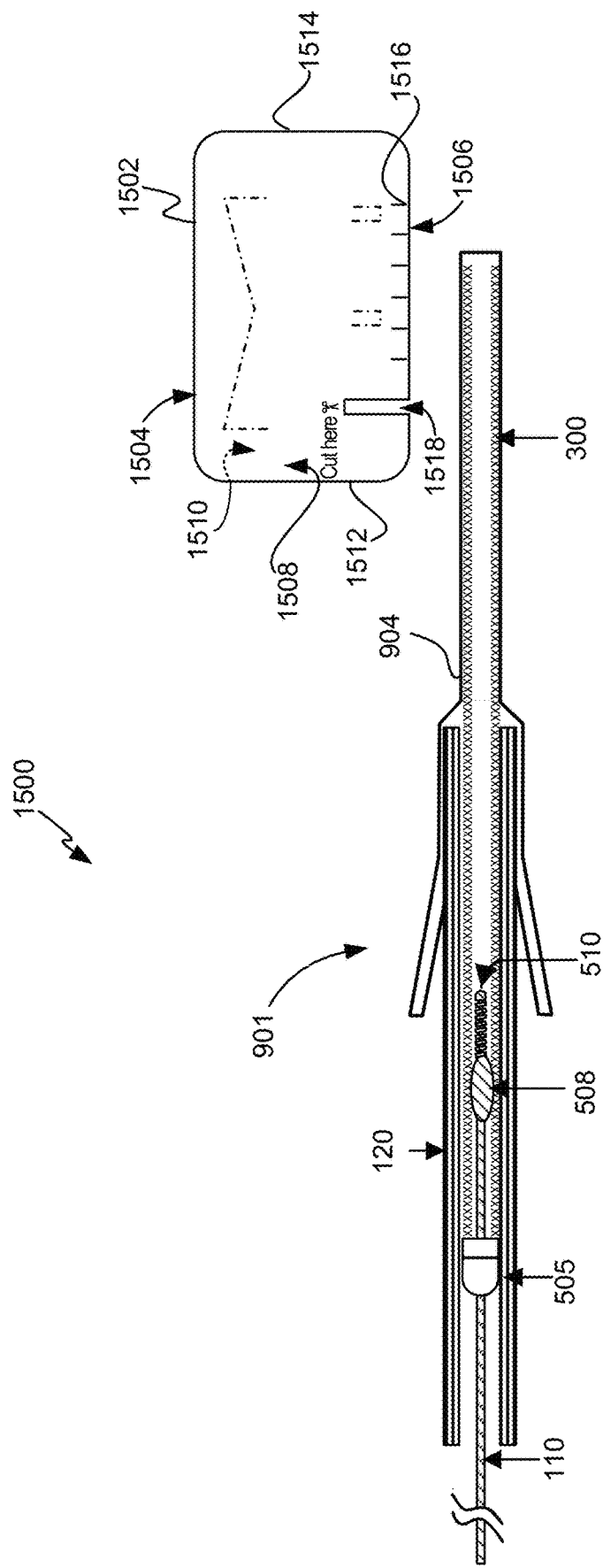
FIG. 15 is an illustration of one embodiment of a customizable flow diverter delivery system.

As shown in FIG. 15, a second customizable flow diverter delivery system 1500 includes a template 1502. The template 1502 comprises a top 1504, a bottom 1506, a front 1508, a back 1510, a first side 1512, and a second side 1514. The template 1502 includes graduation markings 1516 similar to graduation markings 908 shown at least in FIG. 9. The graduation markings 1516 are configured to aid in cutting the flow diverter 300 to a desired length in a similar manner as described above. The graduation markings 1516 preferably correlate to a deployed length of the flow diverter 300.

In some embodiments, the tubing 904 may comprise graduation markings such as those shown at least in FIG. 9. The second customizable flow diverter delivery system 1500 depicts an alternative and/or supplemental approach to guiding a physician to cut the flow diverter 300 within the peelably removable tubing 904 to a desired length. In at least some approaches, graduation markings may be provided on both the tubing 904 and a template 1502 supplied with a flow diverter delivery system.

In various embodiments, the template 1502 includes a cutting aperture, slit, or notch 1518 extending through the bottom 1506 of the template 1502. The cutting aperture, slit, or notch 1518 is proximate to one of the first side 1512 and the second side 1514. The graduation markings 1516 may be positioned between the cutting aperture, slit, or notch 1518 and the other of the first side 1512 and the second side 1514. For example, the graduation markings 1516 are positioned between the cutting aperture, slit, or notch 1518 and the first side 1512. In another example, the graduation markings 1516 are positioned between the cutting aperture, slit, or notch 1518 and the second side 1514, as shown in FIG. 15.

In some embodiments, the template 1502 includes a first set of graduation markings along the bottom 1506 of the front 1508 of the template 1502 and a second set of graduation markings along the bottom 1506 of the back 1510 of the template 1502. In one embodiment, one of the front 1508 of the template 1502 and the back 1510 of the template 1502 is configured for right-handed users and the other of the front 1508 of the template 1502 and the back 1510 of the template 1502 is configured for left-handed users.

In various embodiments, the template 1502 comprises a formula configured to aid in cutting the flow diverter 300 to the desired length, not shown. The formula may be printed along the top 1504 of the template 1502. For example, the formula may be printed along the top portion of the template 1502. In other examples, the formula may be centered on either the front 1508 and/or the back 1510 of the template 1502. The formula may be printed anywhere along the template 1502 on either side. In a preferred embodiment, the formula and the graduation markings 1516 are printed on each of the front 1508 and the back 1510 of the template 1502.

In at least one embodiment, the formula includes:

$$L_T = L_I - L_D R$$
$$R = 0.27D + 1.2$$

where:
$L_T$=Trimmed Length
$L_D$=Deployed Length
$L_I$=Insheath Length

R=Ratio
D=Implant Diameter

In one example, an implant diameter (D) is 4 mm, the desired deployed length ($L_D$) is 25 mm, and the Insheath length ($L_I$) is 80 mm.

To calculate:

$$R = 0.27(4) + 1.2 = 2.28$$

$$L_T = 80 - 25(2.28) = 23 \text{ mm}$$

Therefore, in order to achieve a deployed length of 25 mm, an operator needs to trim off 23 mm.

Figure 16:
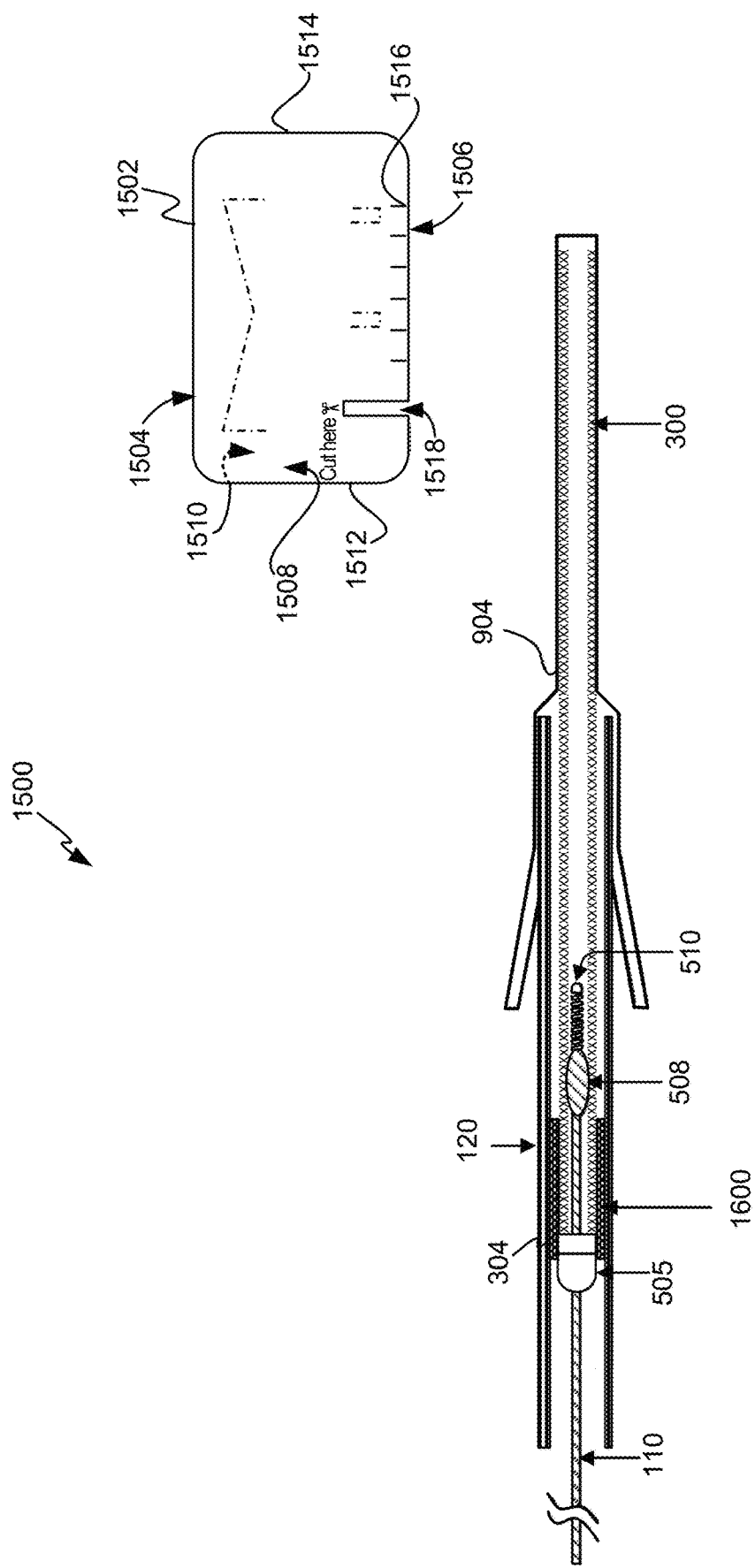
FIG. 16 is an illustration of one embodiment of a customizable flow diverter delivery system having a protective sleeve.

As shown in FIG. 16, the second customizable flow diverter delivery system 1500 includes a protective sleeve 1600 extending along and around a proximal end 304 of the flow diverter 300, wherein the protective sleeve 1600 is configured to reduce friction and/or reduce damage to the flow diverter 300 when the flow diverter 300 is moved relative to the elongate tubular member (e.g., introducer sheath 120). In various approaches, the protective sleeve 1600 extends beyond the proximal end 304 of the flow diverter 300 and/or the pusher 505, as shown in FIG. 16.

The protective sleeve 1600 may be a heat shrink plastic. In some embodiments, the protective sleeve 1600 can comprise a flexible polymer that is coupled to the deployment wire 110. In some embodiments, the protective sleeve 1600 can be coupled to the deployment wire 110 at a position distal of all or portions of the deployment features (e.g., such as friction bump 508, support coil 510, etc.). In some embodiments, the protective sleeve 1600 can comprise a heat-shrink polymer tube that can be positioned over the proximal end 304 of the flow diverter 300 and over a portion of the deployment wire 110 distal of the flow diverter 300. The protective sleeve 1600 can then be heat-shrunk around the flow diverter 300 to snugly fit around the flow diverter 300. The protective sleeve 1600 is coupled to the pusher 505 and/or the core wire 112.

The protective sleeve 1600 may further include one or move slits (not shown) extending proximally from a distal end of the protective sleeve 1600. The one or more slits separate the portion of the protective sleeve 1600 extending over the proximal end 304 of the flow diverter 300 into a plurality of segments. For example, in an embodiment of the protective sleeve 1600 containing two slits, the protective sleeve 1600 can be divided into two pieces, which can be two equal halves. The one or more slits can allow the protective sleeve 1600 to open and separate from the flow diverter 300 as the flow diverter 300 is deployed. The protective sleeve 1600 may extend distally beyond the catheter 104 and split such that the protective sleeve 1600 separates from the flow diverter 300, allowing the flow diverter 300 to expand, and allowing the retraction of the protective sleeve 1600 into the catheter 104 upon full deployment of the flow diverter 300.

Figure 17:
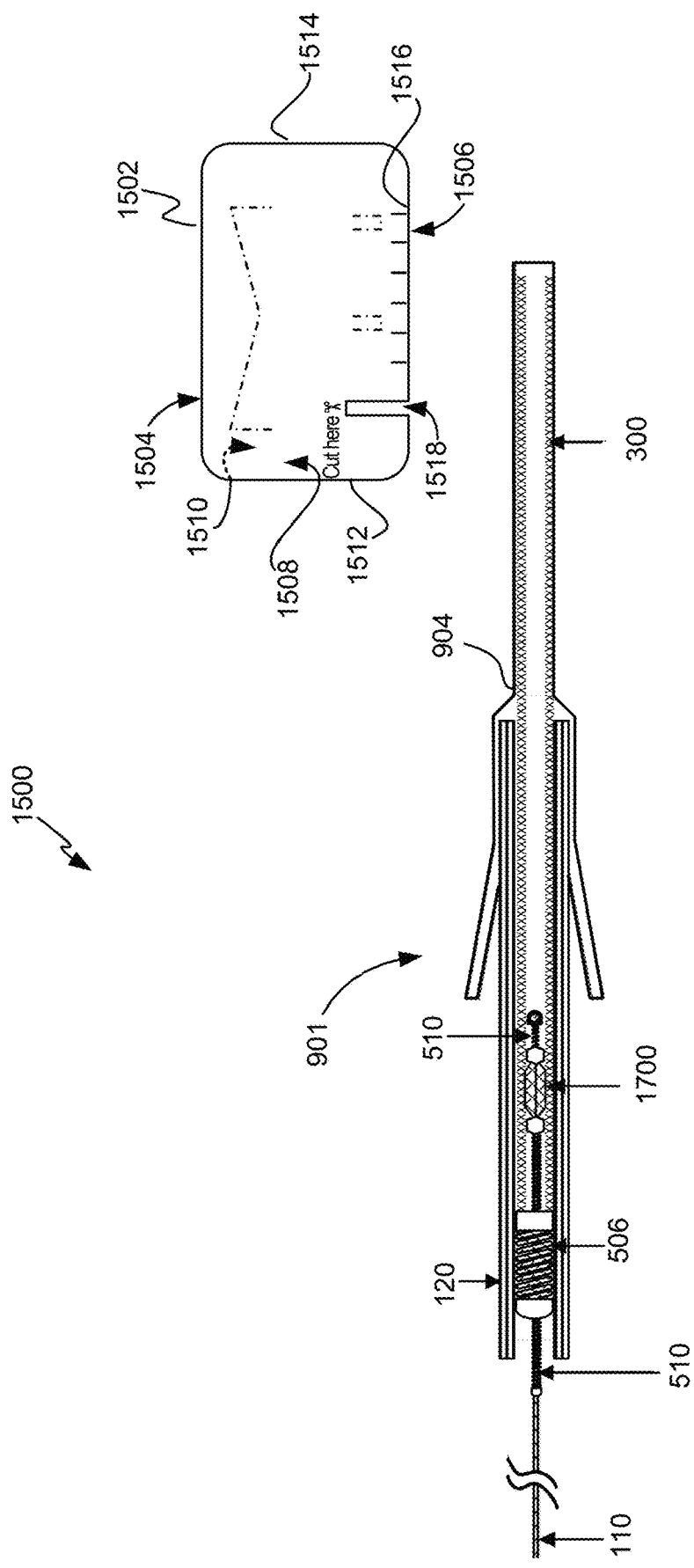
FIG. 17 is an illustration of one embodiment of a customizable flow diverter delivery system having a self-expanding element.

As shown in FIG. 17, the second customizable flow diverter delivery system 1500 includes the customizing member 901 an expanding element 1700 wherein the expanding element 1700 is configured to reduce friction and/or reduce damage to the flow diverter 300 when the flow diverter 300 is moved relative to the elongate tubular member (e.g., introducer sheath 120). The expanding element 1700 may be a self-expanding element or a controlled expanding element. In some embodiments, a self-expanding element can expand upon exiting the catheter 104. In some embodiments, the controlled expanding element can expand when controlled to expand. The expanding element 1700 can comprise, for example, a stent, a braid, a balloon, or the like. In some embodiments in which the expanding element 1700 comprises a braided member, the thickness of the stands of the braid can be varied to achieve a desired effect. For example, the strands can be thicker to provide increased expansion force, or the stands can be thinner to provide increased flexibility. In some embodiments, the strands can comprise a variety of material including, for example, DFT, which can be, for example, radiopaque. In some embodiments, the strands can comprise a polymer such as a high tensile strength polymer. In some embodiments, a polymer used in the strands can advantageously increase friction between the expanding element 1700 and the flow diverter 300, thereby increasing the ability of the expanding element 1700 to retract the flow diverter 300. In embodiments in which the stands comprise a polymer, that polymer can be treated and/or doped to be radiopaque.

Figure 18:
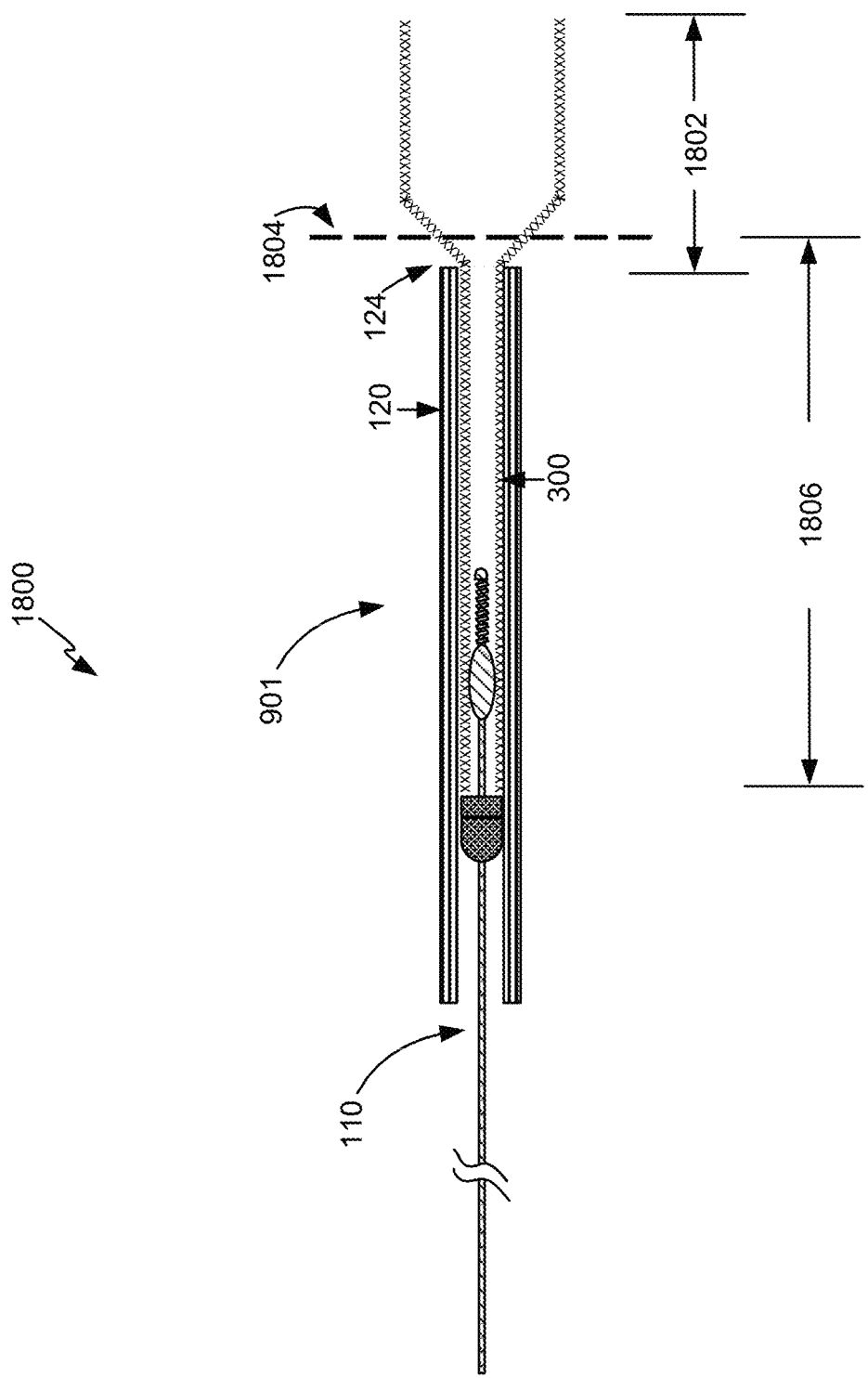
FIG. 18 is an illustration of one embodiment of a customizable flow diverter delivery system.

Referring now to FIG. 18, a customizable flow diverter delivery system 1800 may be implemented without tubing. In such an embodiment, the customizing member 901 does not include distally attached cuttable tubing as shown in previous embodiments. In this alternative embodiment, the flow diverter 300 may extend a length 1802 beyond the distal end 124 of the introducer sheath 120. As further seen, in such an embodiment, the deployment wire 110 terminates within the introducer sheath 120 such that the deployment wire 110 does not distally extend beyond the distal end 124 of the introducer sheath 120. A physician may use a template (not shown) to measure and cut 1804 the flow diverter 300 to the desired length 1806 and the flow diverter 300 may be retracted into the introducer sheath 120 as described in detail above. In such an embodiment, and as discussed above with respect to FIGS. 9 through 17. The introducer sheath 120 can have a length sufficient to receive the entirety of the flow diverter 300, whether trimmed or untrimmed.

Figure 19:
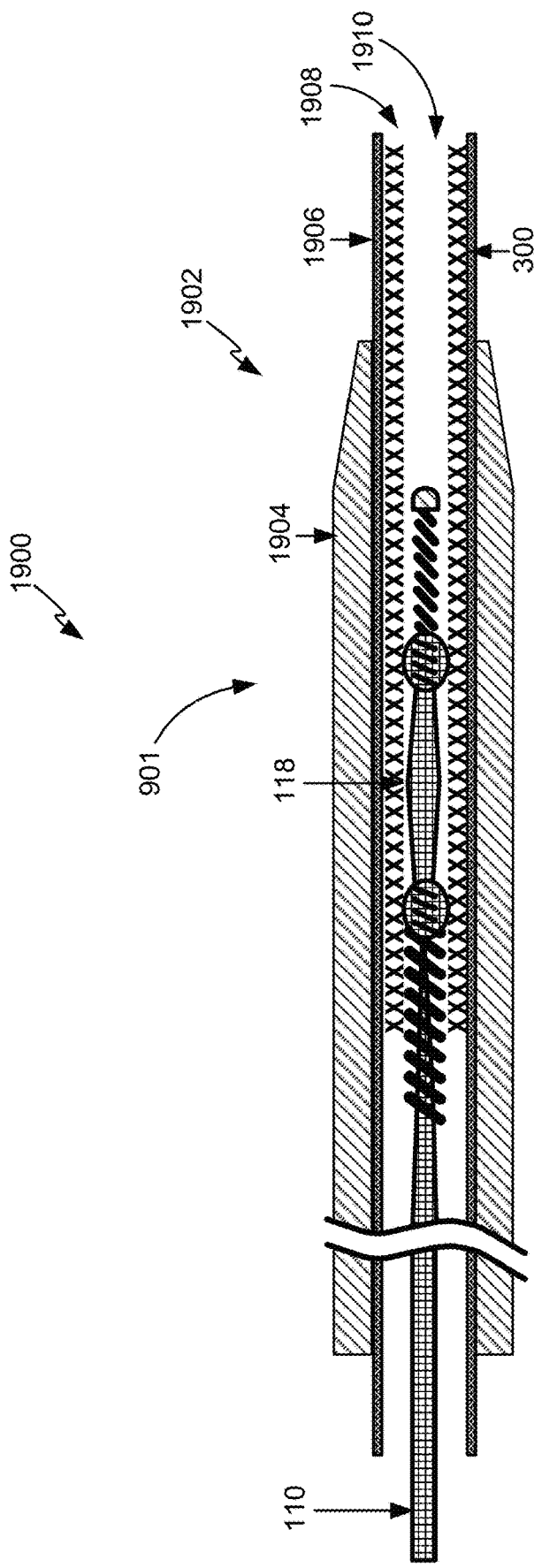
FIG. 19 is an illustration of one embodiment of a customizable flow diverter delivery system.

Referring now to FIG. 19, a customizable flow delivery system 1900 includes a customizing member 901 including a cuttable introducer sheath 1902. The cuttable introducer sheath 1902 includes an outer introducer sheath layer 1904 and an inner cuttable tubing 1906 surrounding the flow diverter 300. In some approaches, the outer introducer sheath layer 1904 is rigid and the inner cuttable tubing 1906 is semi-rigid (e.g., similar to the tubing 904 described in detail above). In some embodiments, the outer introducer sheath layer 1904 has a length sufficient to receive the entirety of the flow diverter 300, whether trimmed or untrimmed.

In various approaches, the introducer sheath 1902 (e.g., the outer introducer sheath layer 1904) may be tapered distally. In other approaches, the introducer sheath 1902 is not tapered and includes a constant diameter throughout the length of the introducer sheath 1902.

In one alternative embodiment, not shown, the introducer sheath 1902 is a unitary, cuttable feature. For example, the introducer sheath 1902 only comprises a relatively thin and rigid material in contrast to the embodiment including the outer introducer sheath layer 1904 and the inner cuttable tubing 1906 and as shown in FIG. 19. In some embodiments, the unitary, cuttable introducer sheath 1902 is semi-rigid to allow cutting of the introducer sheath 1902, but is sufficiently rigid to engage with the catheter hub 106 to allow transfer of the flow diverter 300 from the introducer sheath 1902 to the catheter 104.

The outer introducer sheath layer 1904 defines an outer sheath layer lumen 1908 and the inner cuttable tubing 1906 defines an inner tubing lumen 1910. A flow diverter (such as flow diverter 300 described in detail above) is contained within the inner tubing lumen 1910 in a constrained position, as shown in FIG. 19.

In various embodiments, the system 1900 includes a deployment wire (such as deployment wire 110 described in detail above) extending into the inner tubing lumen 1910 and into the flow channel of the flow diverter 300. As the deployment wire 110 is distally advanced, the flow diverter 300 deploys from the catheter 104 and begins to expand. This distal advance continues until the flow diverter 300 is fully deployed.

As shown in FIG. 20, the inner cuttable tubing 1906 and the flow diverter 300 may be cut 2002 to a desired length 2004 according to any of the aspects described in detail above. As seen in FIGS. 20 through 26, the deployment wire 110 and/or the deployment features 118 terminate proximally of the distal end of the flow diverter 300, and specifically terminate proximally of the location at which the flow diverter 300 may be cut 2002 such that the cutting of the flow diverter 300 does not cut the deployment wire 110 and/or the deployment features 118.

In some embodiments, the flow diverter 300 can be cut 2002 to the desired length 2004. For example, the inner cuttable tubing 1906 may include graduation markings and/or be provided with a template having graduation markings for enabling a physician to determine and measure the desired length 2004. The remaining portion 2006 may be discarded after performing the cut 2002 (e.g., after cutting the inner cuttable tubing 1906 and the flow diverter 300) as depicted in FIG. 21.

Figure 22:
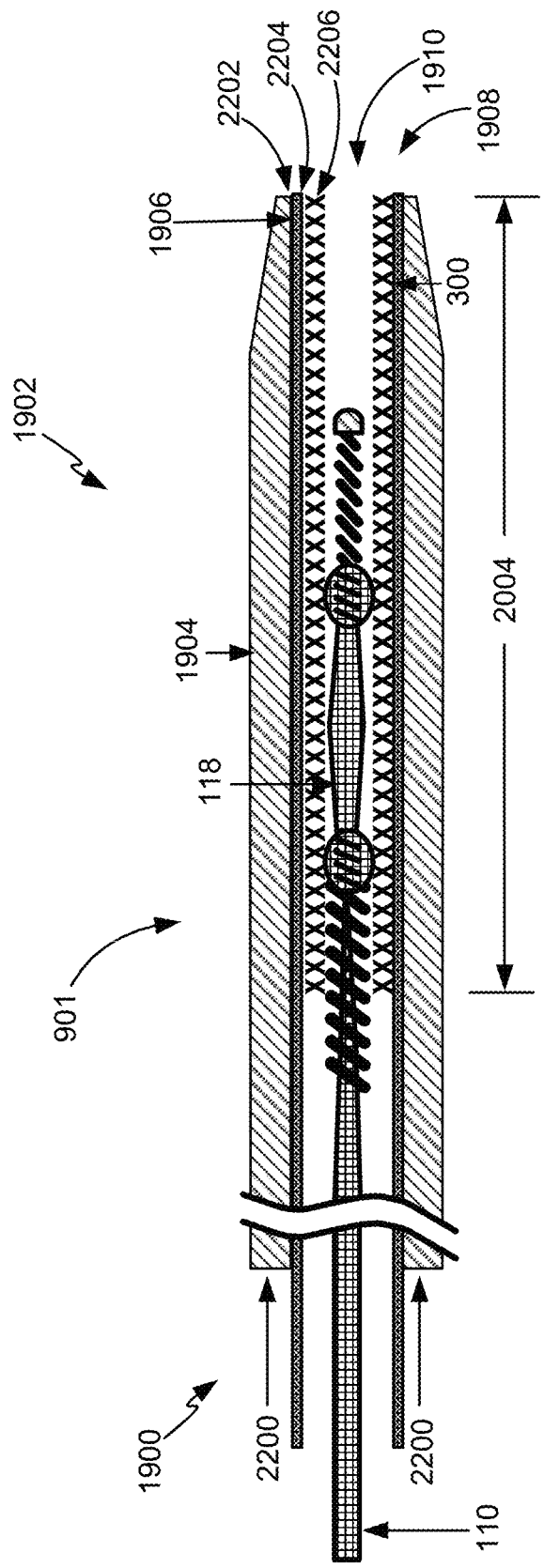
FIG. 22 is an illustration of one embodiment of a customizable flow diverter delivery system.

In some embodiments, as shown in FIG. 22, after cutting the inner cuttable tubing 1906 and the flow diverter 300, the outer introducer sheath layer 1904 may be advanced distally 2200 position the inner tubing within the outer sheath layer such that a distal end of the inner tubing is within the outer sheath layer lumen. In another embodiment, the outer introducer sheath layer 1904 may be advanced distally 2200 to align the distal end 2202 of the outer introducer sheath layer 1904 with the distal end 2204 of the inner cuttable tubing 1906 and/or the distal end 2206 of the flow diverter 300. In another embodiment, the inner cuttable tubing 1906 and the flow diverter may be retracted into the outer introducer sheath layer 1904. In yet another embodiment, the inner cuttable tubing 1906 and the flow diverter 300 are provided separately from outer introducer sheath layer 1904 and, after the cutting, the trimmed inner cuttable tubing 1906 and the flow diverter 300 are inserted into the outer introducer sheath 1904, as illustrated in exemplary FIGS. 23-26.

In an alternative embodiment as shown in FIG. 23, the customizing member 901 includes the inner cuttable tubing 1906 and the outer introducer sheath layer 1904. In the embodiment of FIG. 23, the inner cuttable tubing 1906 and the flow diverter 300 are provided separately from outer introducer sheath layer 1904. The inner cuttable tubing 1906 includes one or more locking elements 2302. The one or more locking elements 2302 may be spaced around the circumference of the inner cuttable tubing 1906. In one exemplary aspect, the inner cuttable tubing 1906 includes at least two locking elements 2302 located on opposite sides of the inner cuttable tubing 1906, as shown.

In some aspects, the locking elements 2302 are located on the outer introducer sheath layer 1904. The one or more locking elements 2302 may be spaced around the circumference of the outer introducer sheath layer 1904. In one exemplary aspect, the outer introducer sheath layer 1904 includes at least two locking elements 2302 located on opposite sides of the outer introducer sheath layer 1904.

In various embodiments, after cutting the inner cuttable tubing 1906 and the flow diverter 300, the trimmed inner cuttable tubing 1906 and the flow diverter 300 are inserted into the outer introducer sheath 1904 and the locking elements 2302 are wedged between the outer introducer sheath layer 1904 and the inner cuttable tubing 1906 and are configured to lock the position of the outer introducer sheath layer 1904 relative to the inner cuttable tubing 1906, as shown in FIG. 24.

In another embodiment, the inner cuttable tubing 1906 and the flow diverter 300 are provided in the outer introducer sheath layer 1904 and the distal ends of the inner cuttable tubing 1906 and the flow diverter 300 extend beyond the distal end of the outer introducer sheath layer 1904 for cutting to a desired length. After cutting the inner cuttable tubing 1906 and the flow diverter 300, the outer introducer sheath layer 1904 may be retracted such that the locking elements 2302 are wedged to the outer introducer sheath layer 1904.

Figure 25:
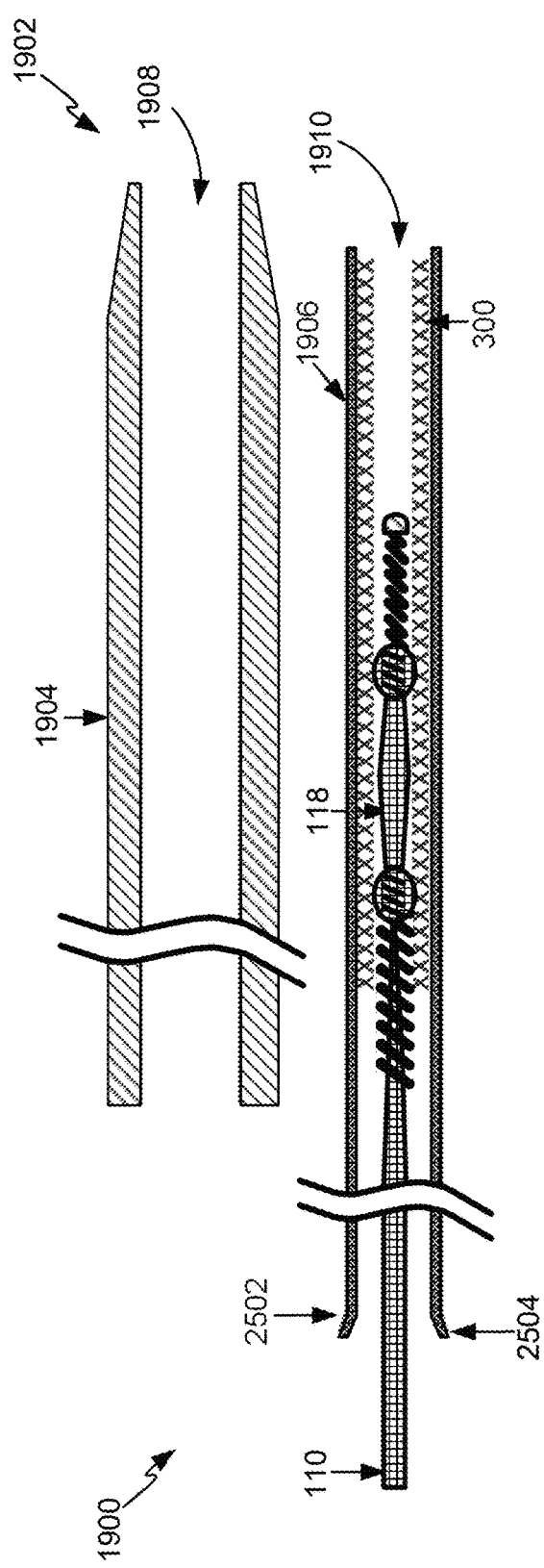
FIG. 25 is an illustration of one embodiment of a customizable flow diverter delivery system.

Alternatively, as shown in FIG. 25, the inner cuttable tubing 1906 includes a flared end 2502 around the circumference of the proximal end 2504 of the inner cuttable tubing 1906.

In various embodiments, the flared end 2502 is wedged between the inner cuttable tubing 1906 to the outer introducer sheath layer 1904 and is configured to lock the position of the outer introducer sheath layer 1904 relative to the inner cuttable tubing 1906.

Figure 26:
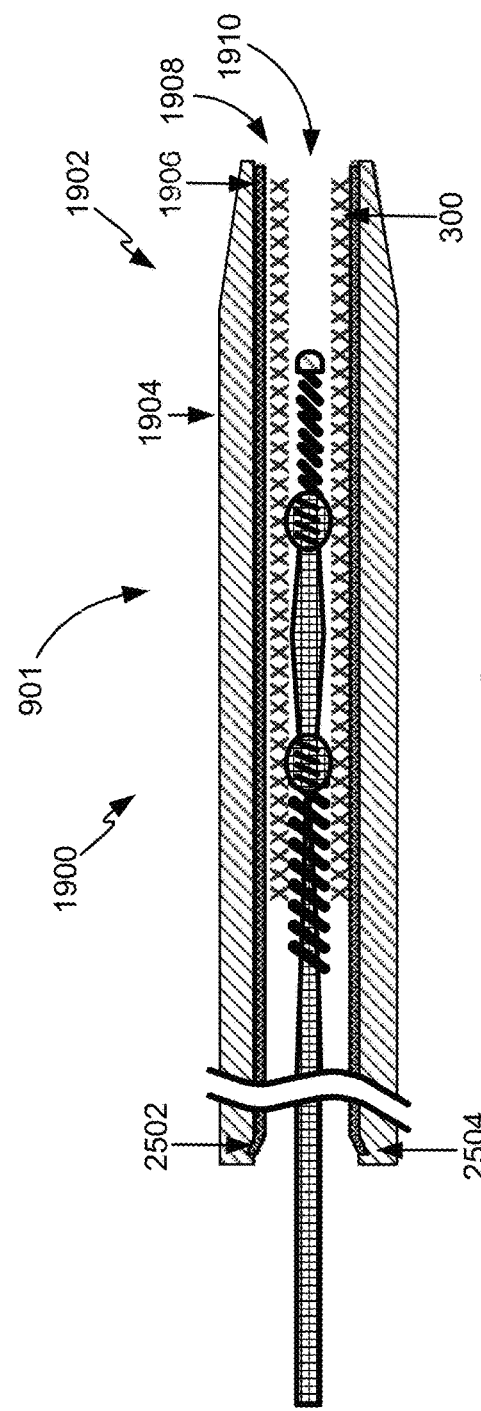
FIG. 26 is an illustration of one embodiment of a customizable flow diverter delivery system.

In various embodiments, after cutting the inner cuttable tubing 1906 and the flow diverter 300, the trimmed inner cuttable tubing 1906 and the flow diverter 300 are inserted into the outer introducer sheath 1904 and the flared end 2502 is wedged between the outer introducer sheath layer 1904 and the inner cuttable tubing 1906 and are configured to lock the position of the outer introducer sheath layer 1904 relative to the inner cuttable tubing 1906, as shown in FIG. 26.

In another embodiment, the inner cuttable tubing 1906 and the flow diverter 300 are provided in the outer introducer sheath layer 1904 and the distal ends of the inner cuttable tubing 1906 and the flow diverter 300 extend beyond the distal end of the outer introducer sheath layer 1904 for cutting to a desired length. After cutting the inner cuttable tubing 1906 and the flow diverter 300, the outer introducer sheath layer 1904 may be retracted over the flared end 2502 is wedged to the outer introducer sheath layer 1904.

Figure 27:
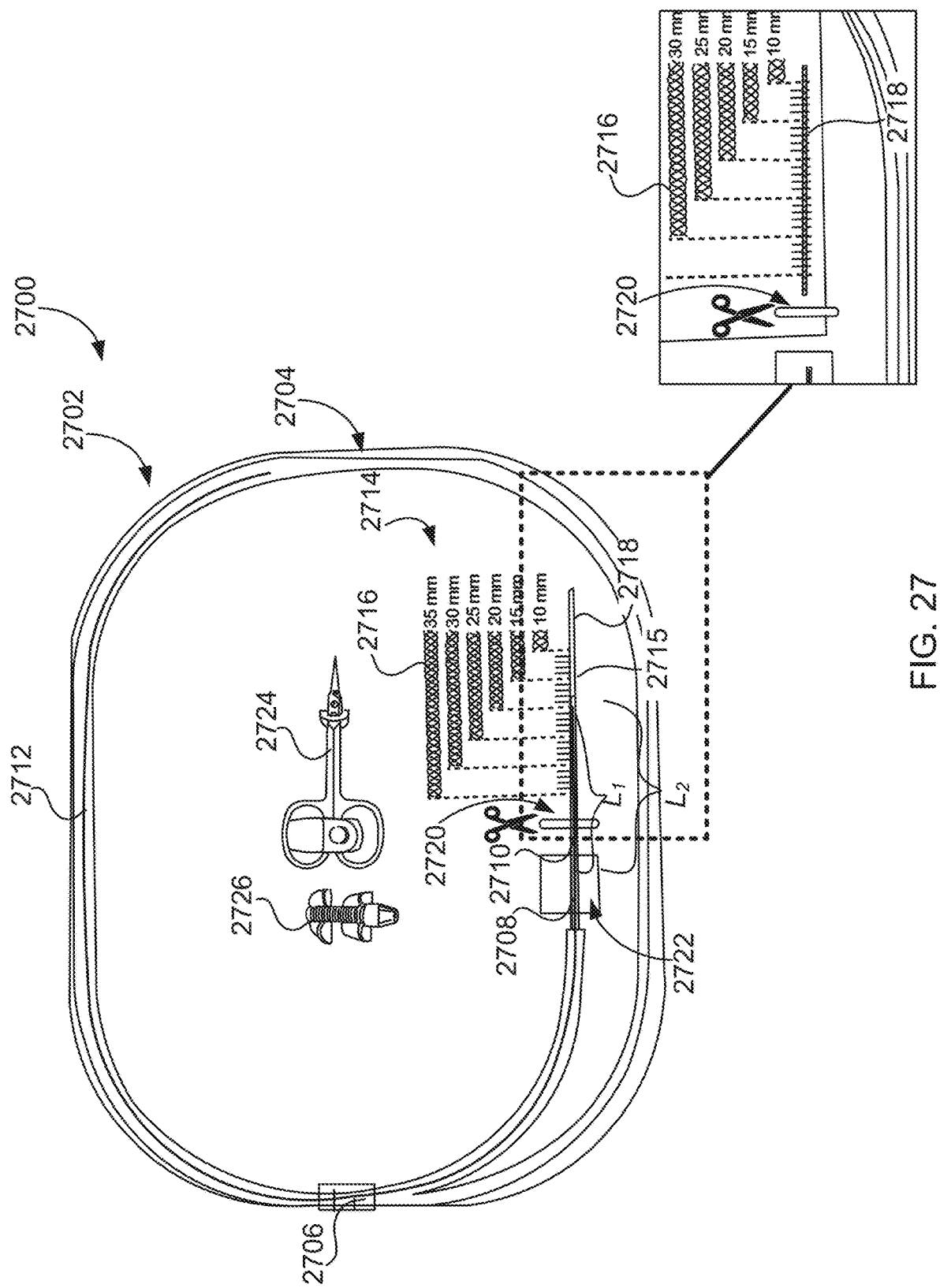
FIG. 27 is an illustration of one embodiment of packaging for a customizable flow diverter delivery system.

FIG. 27 is an illustration of one embodiment of packaging for a customizable flow diverter delivery system. In various embodiments, "packaging" may be interchangeably referred to as "housing" unless otherwise noted herein. System 2700 includes packaging 2702 which is primary packaging or packaging that is in direct contact with the flow diverter delivery device 2704. Packaging 2702 may provide a backing for supporting the flow diverter delivery device 2704 during transportation, storage, or the like. For example, the packaging 2702 may include a packaging tray. In particular, the flow diverter delivery device 2704 may be removably coupled to the packaging 2702 via fastening members 2706 such as an adhesive, ties, clips, twists, or the like. The packaging 2702 may be formed of any material, including, but not limited to, paper, plastic, corrugated cardboard, glass, metal, wood, foam, etc., or any combination thereof. The fastening members 2706 may be integrally formed with the packaging 2702 and/or the fastening members 2706 may be separately formed and used with the packaging 2702.

According to various embodiments, the flow diverter delivery device 2704 may include an elongate tubular member 2708, such as an introducer, including any of the various embodiments described with respect to other figures. For example, the elongate tubular member 2708 is a cuttable introducer. The flow diverter delivery device 2704 may include a flow diverter 2710 at least partially contained within the lumen of the elongate tubular member 2708 in a constrained configuration. As shown in FIG. 27, the flow diverter 2710 extends a first length $L_1$ beyond the distal end of the elongate tubular member 2708. The flow diverter delivery device 2704 may include a deployment wire 2712 extending into the lumen of the elongate tubular member 2708 and movement of the deployment wire 2712 relative to the elongate tubular member 2708 moves the flow diverter 2710 relative to the elongate tubular member 2708, as described in detail above.

The flow diverter delivery device 2704 may further include a peelable tubing 2715 extending along and around the distal portion of the elongate tubular member 2708. The cuttable, peelable tubing 2715 may include a peelable FEP. In other embodiments, the cuttable, peelable tubing 2715 may include any polymer tubing material. In various embodiments, the tubing 2715 extends a second length $L_2$ beyond the distal end of the elongate tubular member 2708. In an exemplary embodiment, the distal end of the flow diverter 2710 is within the tubing 2715 and the tubing 2715 is cuttable, as described in detail above. The tubing 2715 is peelably removable from the elongate tubular member 2708.

As further shown in FIG. 27, the packaging 2702 includes an integrated template 2714. The template 2714 may include graduation markings 2716. The graduation markings 2716 are configured to aid in cutting the flow diverter 2710 to a desired length. The template 2714 may correlate the graduation markings 2716 to a deployed length of the flow diverter 2710. The graduation markings 2716 may be equally spaced according to various embodiments. For example, the graduation markings 2716 may be incremental increases along a scale. In other embodiments, the graduation markings 2716 are not equally spaced. For example, various lengths may be predetermined and marked on the template 214. The template 2714 may be directly printed on the packaging 2702 in some embodiments. In other embodiments, the template 2714 is a sticker or insert that is coupled to the packaging 2702 in a manner known in the art. The packaging 2702 may further include an alignment member 2718 disposed below the graduation markings 2716. The alignment member 2718 may be a clear tube, lumen, etc., for aligning the flow diverter delivery device 2704 relative to the graduation markings 2716, e.g., to ensure that the flow diverter delivery device 2704 is straight and parallel to the graduation markings 2716 for accurately determining a desired length of the flow diverter 2710. The inset of FIG. 27 highlights the position of the alignment member 2718 relative to the graduation markings 2716 and the cutting aperture, slit, or notch 2720.

In various embodiments, the alignment member 2718 may include a frictional surface that engages with the flow diverter delivery device 2704 for holding the flow diverter delivery device 2704 in place during the cutting. Furthermore, the alignment member 2718 frictionally engages with the flow diverter delivery device 2704 for preventing the health care professional for unintentionally pulling out the flow diverter delivery device 2704 too far and too fast (e.g., beyond the desired length).

According to at least some embodiments, the template 2714 including graduation markings 2716 may not be a physical template. For example, the template 2714 may be projected onto, or otherwise optically provided, the packaging 2702 or a component thereof. The template 2714 may be visible to a health care professional via a microscope, a mobile phone, or other imaging device to aid in cutting the flow diverter 2710 to a variable length.

The packaging 2702 including the template 2714 may further include a cutting aperture, slit, or notch 2720 extending through the packaging 2702. The cutting aperture, slit, or notch 2720 may be disposed proximally of the graduation markings 2716. In various embodiments, the cutting aperture, slit, or notch 2720 is slot for a pair of scissors, a blade, trimmers, clippers, snips, or other cutting tool, to be inserted into for cutting the flow diverter delivery device 2704. In at least some embodiments, the cutting aperture, slit, or notch 2720 is sized and shaped for ensuring alignment of the scissors within the cutting aperture, slit, or notch 2720 and accuracy of the cut relative to the graduation markings 2716. For example, the cutting aperture, slit, or notch 2720 is sized and shaped such that the scissors do not laterally translate (e.g., thereby varying the length of the flow diverter delivery device 2704) once inserted into the cutting aperture, slit, or notch 2720. Said another way, the width of the cutting aperture, slit, or notch 2720 constrains a cutting tool to aid in cutting the flow diverter at a desired location and/or at a desired angle. For example, according to various embodiments, a health care professional may cut the flow diverter at a right angle (e.g., perpendicular) to an axis of the flow diverter. In other embodiments, a 45 degree angle may be desired.

In some embodiments, the packaging 2702 may further include an opening 2722 for retraction and advancement of the flow diverter delivery device 2704 relative to the graduation markings 2716. The opening 2722 may be a pinch opening for a health care professional to pinch through and laterally translate the flow diverter delivery device 2704 relative to the template 2714 and the graduation markings 2716. Once aligned, the health care professional may pinch and hold the flow diverter delivery device 2704 through the opening 2722 to maintain the position of the flow diverter delivery device 2704 during the cutting. In exemplary embodiments, the opening 2722 is disposed proximally of the cutting aperture, slit, or notch 2720 such that the cutting aperture, slit, or notch 2720 is disposed between the opening 2722 and the alignment member 2718 and/or the graduation markings 2716.

The packaging 2702 may further include a pair of scissors 2724 (or any cutting tool) for performing the cutting. Accordingly, the cutting aperture, slit, or notch 2720 may be sized and shaped to accommodate the scissors 2724 provided with the flow diverter delivery device 2704 for ensuring accuracy of the cutting.

In various embodiments, the packaging 2702 may include a torquer 2726 and/or various other components for use with the flow diverter delivery device 2704. The packaging 2702 may include more or less components than those shown herein, as would be appreciated by one having ordinary skill in the art upon reading the present disclosure.

Figure 28:
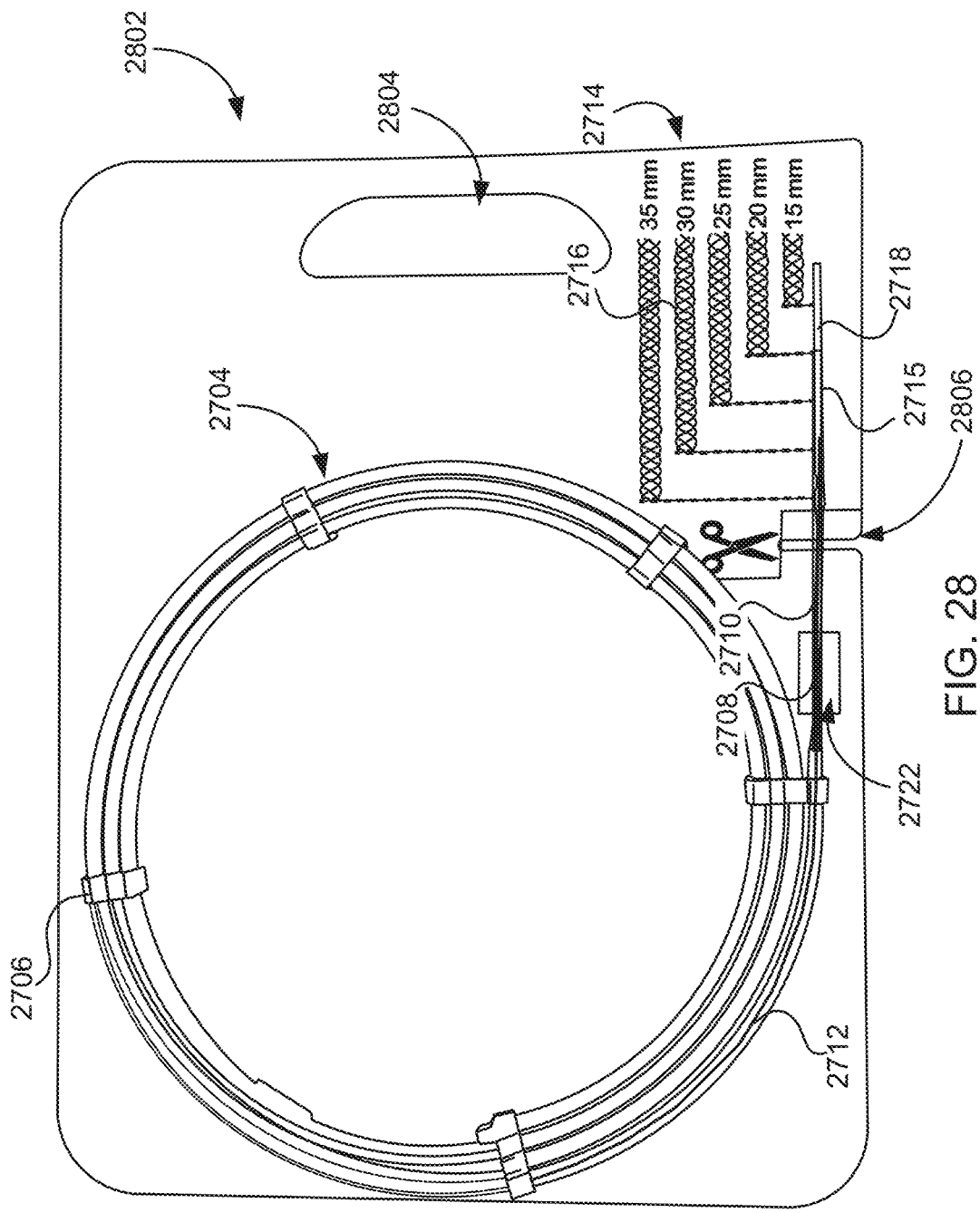
FIG. 28 is an illustration of one embodiment of packaging for a customizable flow diverter delivery system.
Figure 29:
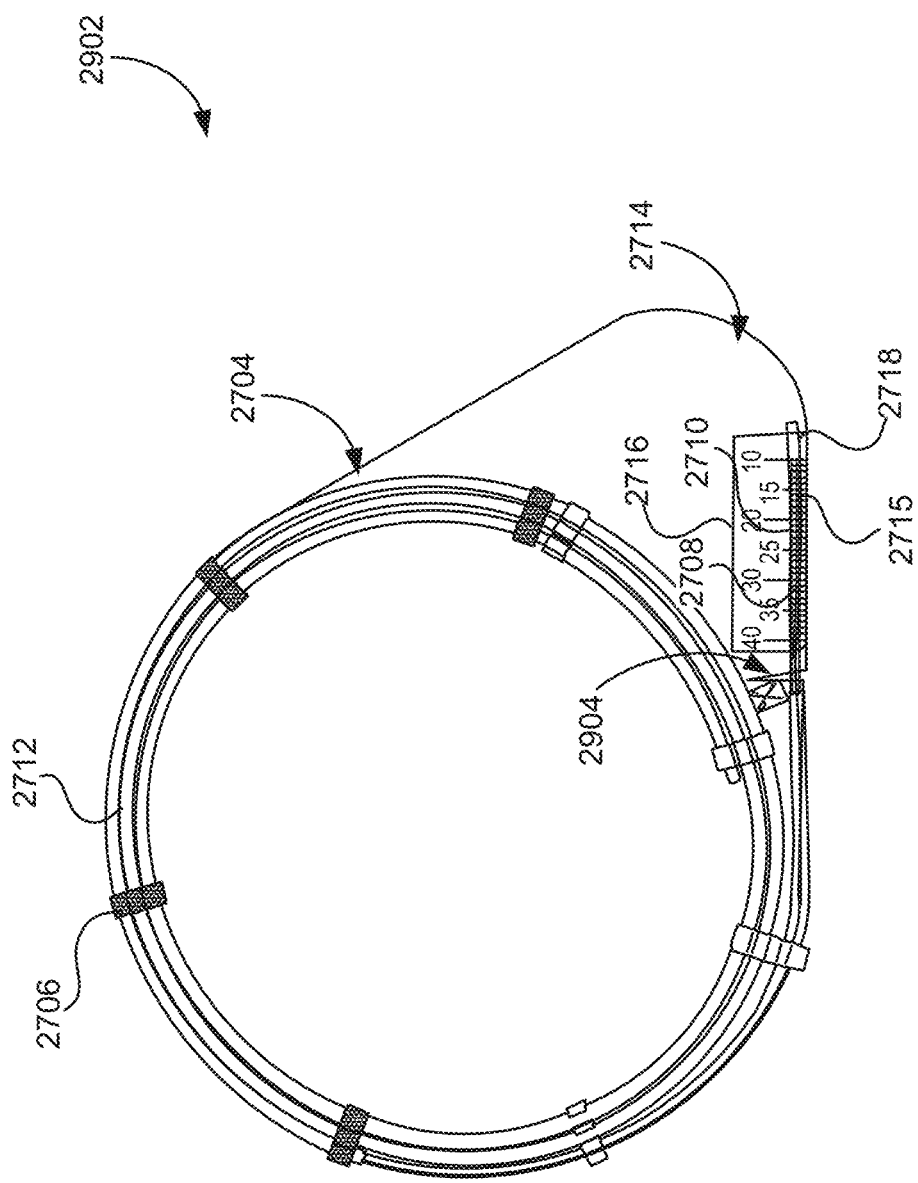
FIG. 29 is an illustration of one embodiment of packaging for a customizable flow diverter delivery system.
Figure 30:
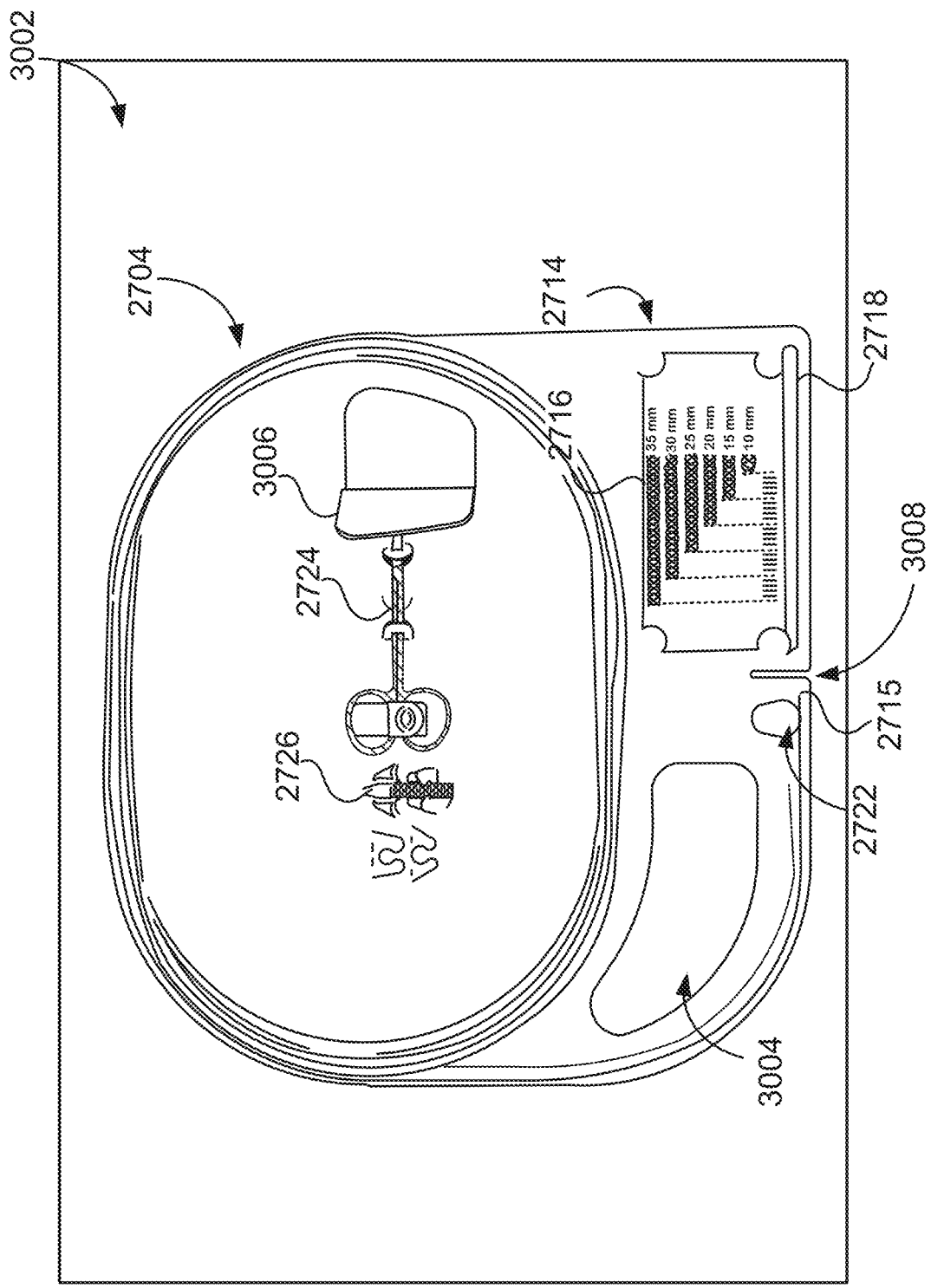
FIG. 30 is an illustration of one embodiment of packaging for a customizable flow diverter delivery system.

FIGS. 28-30 illustrate various embodiments of packaging for a customizable flow diverter delivery system. FIGS. 28-30 illustrate alternative configurations having additional openings, such as opening 2804 and opening 3004, that provide additional handles for handling the packaging 2702. Elements may have similar form and function unless otherwise noted herein. Accordingly, elements having similar form and function may be similarly numbered throughout FIGS. 28-30. FIG. 28 illustrates packaging 2802 having an exemplary alternative cutting aperture, slit, or notch 2806 that extends through a bottom edge of the packaging 2802. FIG. 29 illustrates a simplified embodiment of packaging 2902 that does not include any openings and a cutting aperture, slit, or notch 2904 that extends through a bottom edge of the packaging 2902. FIG. 30 illustrates packaging 3002 including an additional opening 3004 and a flap 3006 for covering the sharp ends of the scissors 2724. FIG. 30 further includes an exemplary alternative cutting aperture, slit, or notch 3008 that extends through a bottom edge of the packaging 3002.

Figure 31:
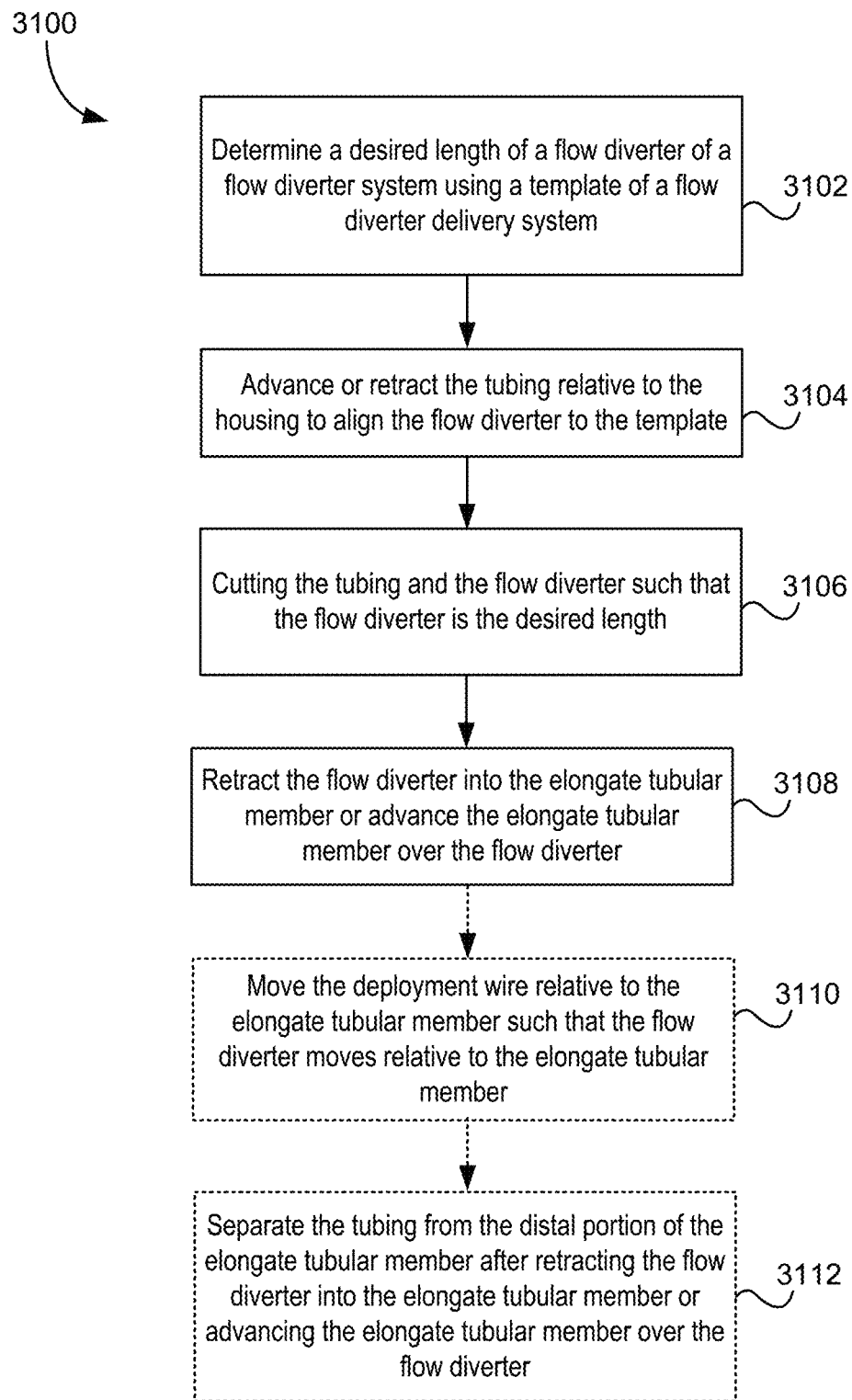
FIG. 31 is a flowchart of a method of customizing a flow diverter delivery system.

FIG. 31 is a flowchart of a method of customizing a flow diverter delivery system. Method 3100 includes various embodiments for customizing a flow diverter for delivery into a neurovascular blood vessel to treat an aneurysm. Method 3100 includes providing a flow diverter system including any of the embodiments described in detail above. In particular, method 3100 includes using flow diverter system including packaging as described with respect to FIGS. 27-30. Method 3100 includes step 3102. Step 3102 includes determining a desired length of a flow diverter of a flow diverter system using the template for customizing the flow diverter. Advantageously, the health care professional is able to determine the desired length and customize the device to the desired length prior to inserting the device. In various embodiments, the template correlates the graduation markings to a deployed length of the flow diverter. Various embodiments of method 3100 describe a housing for the flow diverter system which may refer to any of the packaging embodiments described with respect to FIGS. 27-30.

Step 3104 includes advancing or retracting the tubing relative to the housing to align the flow diverter to the template. Advancing or retracting the tubing relative to the template may include positioning the flow diverter relative to graduation markings equally spaced along the template. The graduation markings are configured to aid in cutting the flow diverter to the desired length. Step 3104 may further include positioning the tubing within an alignment member disposed below the graduation markings for guiding the flow diverter relative to the graduation markings and holding the flow diverter stationary during cutting. An opening disposed at a proximate end of the graduation markings in the housing may be used to advance or retract the tubing relative to the template.

Step 3106 includes, using a cutting aperture, slit, or notch disposed within the housing, cutting the tubing and the flow diverter such that the flow diverter is cut to the desired length. In various embodiments, the cutting aperture, slit, or notch is positioned between the opening and the graduation markings. Cutting the flow diverter such that the flow diverter is the desired length may include cutting the tubing provided with the flow diverter system. Cutting may further include using a cutting tool, such as provided scissors, to cut the flow diverter at a desired location and/or a desired angle via a cutting aperture, slit, or notch extending through the housing.

Step 3108 includes retracting the flow diverter into the elongate tubular member or advancing the elongate tubular member over the flow diverter. The flow diverter may be fully retracted into the elongate tubular member following the cutting. According to various embodiments, the flow diverter is retracted into the elongate tubular member by distally retracting a deployment wire coupled to the flow diverter. In various embodiments, method 3100 may include step 3110 including moving the deployment wire relative to the elongate tubular member such that the flow diverter moves relative to the elongate tubular member. Advancing the elongate tubular member over the flow diverter may include holding the deployment wire stationary while advancing the elongate tubular member.

In various embodiments, method 3100 may further step 3112 including separating the tubing from the distal portion of the elongate tubular member. For example, the tubing may be separated from the distal portion of the elongate tubular member after the flow diverter is retracted into the elongate tubular member. The tubing may be separated from the distal portion of the elongate tubular member by peeling the tubing from the distal portion of the elongate tubular member according to various embodiments described herein. Method 3100 may proceed with loading the flow diverter within the elongate tubular member into an microcatheter or the like for insertion into vasculature of a patient, as would be appreciated by one having ordinary skill in the art upon reading the present disclosure.

FIGS. 32A-32E illustrate exemplary process steps for customizing a flow diverter using a flow diverter delivery system as described herein. According to various embodiments, a health care professional may inject contrast into vasculature of a patient to perform fluoroscopic road mapping in order to measure and estimate the diameter of the target vessel and/or the neck width of the aneurysm. Accordingly, a desired length of a flow diverter may be determined.

Figure 32A:
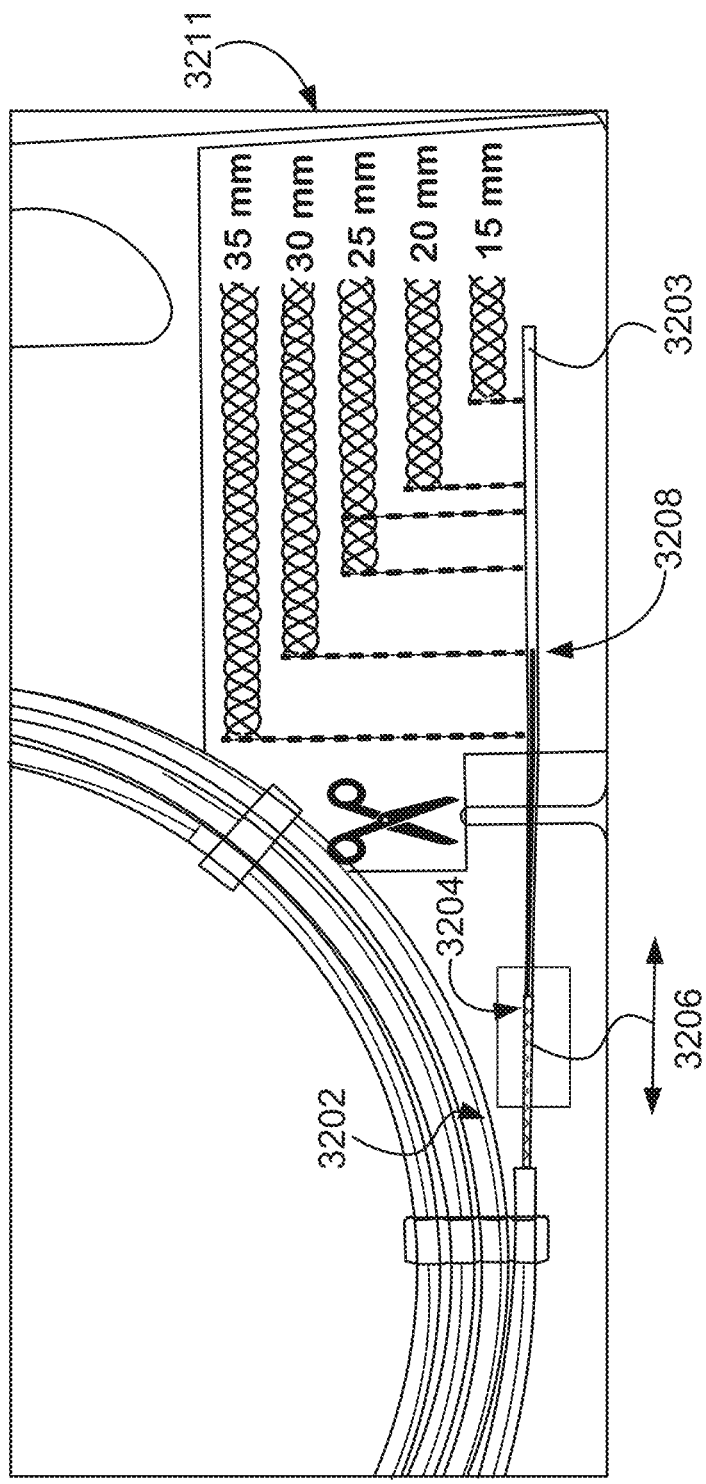
FIGS. 32A-32E illustrate exemplary process steps for customizing a flow diverter delivery system.

FIG. 32A illustrates preparation of a customizable flow diverter according to embodiments of the present disclosure. FIG. 32A illustrates at least embodiments of step 3104 of method 3100 described with respect to FIG. 31. In particular, FIG. 32A illustrates the device 3202 positioned within an opening 3204. The device 3202 may be translated 3206 such that a distal end of the device 3202 is aligned 3208 with the template 3211 and a graduation marking corresponding to a desired length of the deployed flow diverter. For example, the device 3202 illustrated in FIG. 32A will have a final deployed length of 30 mm. In some embodiments, at least a portion of the device 3202 is positioned within an alignment member 3203 for maintaining the device 3202 in a straight configuration and parallel to the template 3211 for accurate measuring, etc. A health care professional may align the device 3202 and pinch the device 3202 through the opening 3204 for proceeding to the cutting 3210 illustrated in FIG. 32B.

Figure 32B:
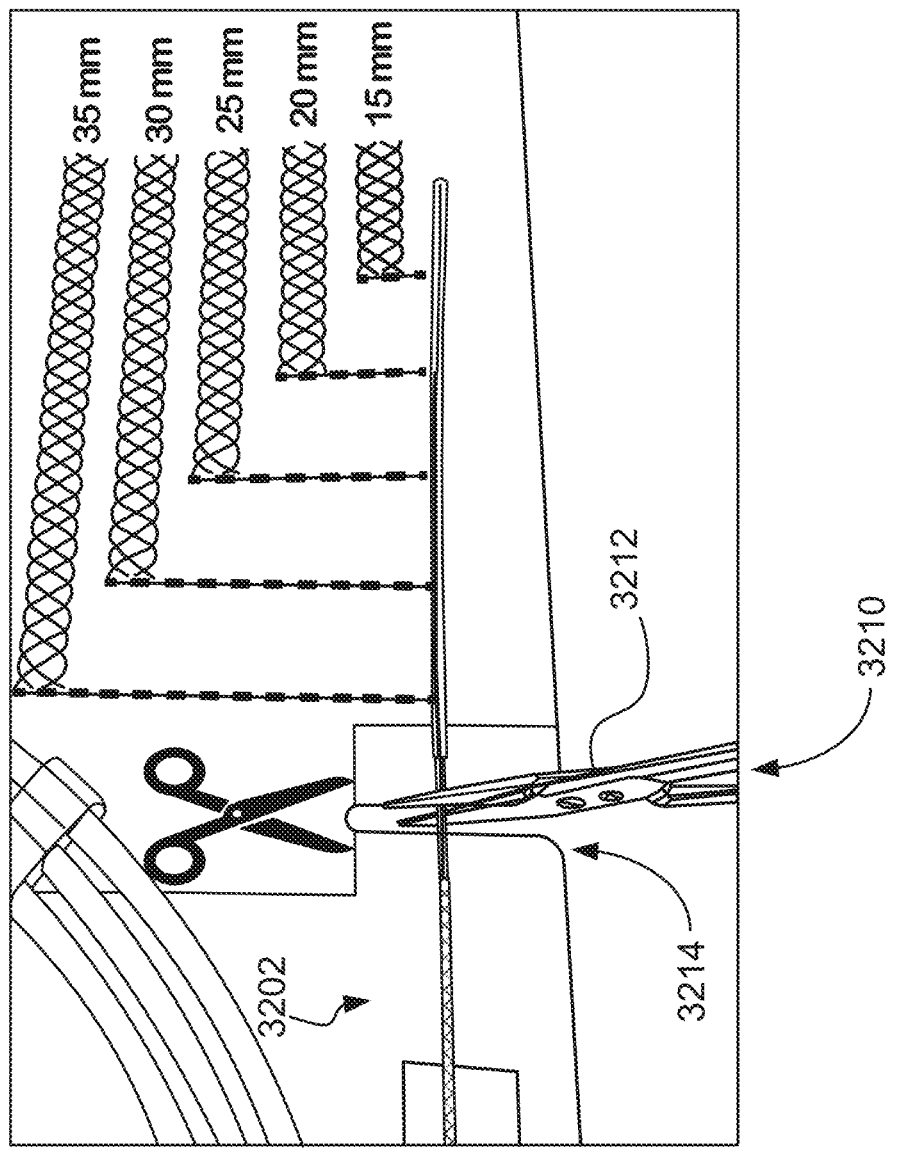

FIG. 32B illustrates cutting 3210 the device 3202 to the desired length by inserting the scissors 3212 through a cutting aperture, slit, or notch 3214, as described in detail above. FIG. 32B illustrates at least embodiments of step 3106 of method 3100 described with respect to FIG. 31.

Figure 32C:
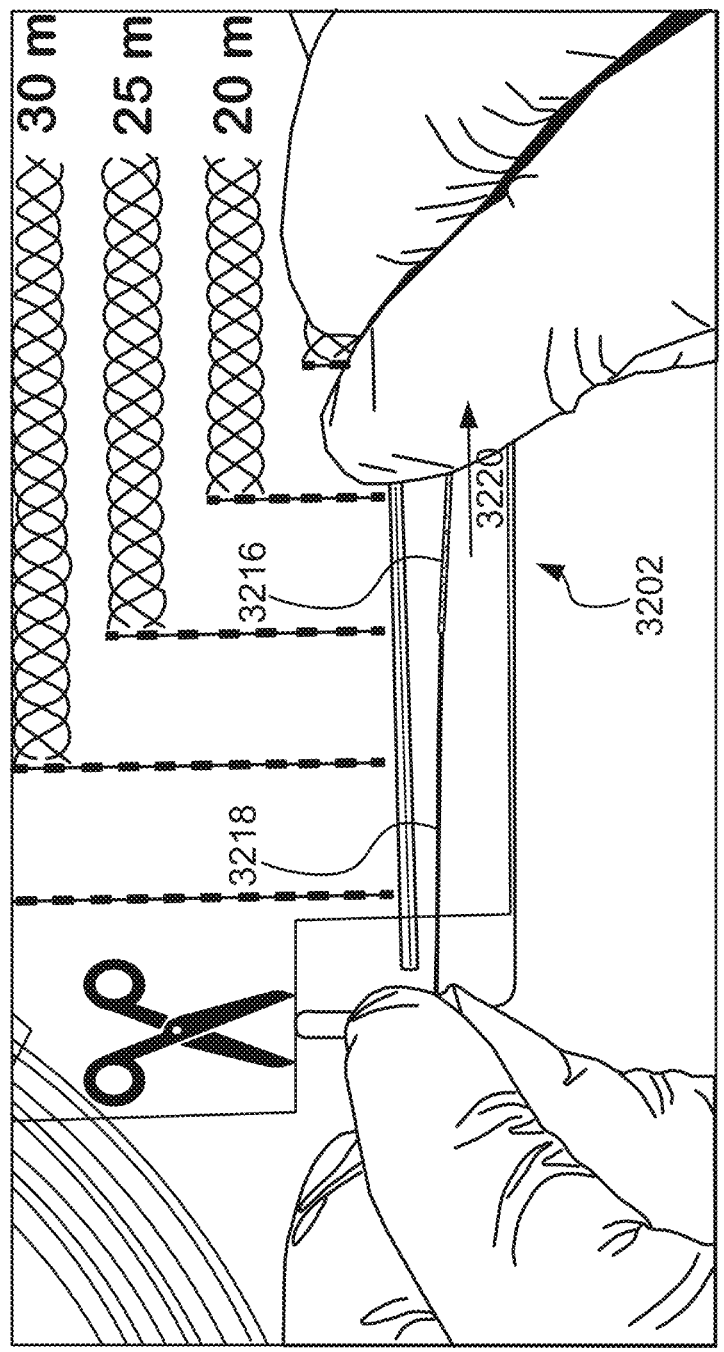

FIG. 32C illustrates the device 3202 removed from the packaging such that the sheath 3216 is exposed. A health care professional should inspect the device 3202 and the sheath 3216 for any damage. The device 3202 is retracted into the sheath 3216 by advancing the sheath 3216 forward 3220 while holding the deployment wire 3218 in place. The sheath 3216 may be advanced forward 3220 until the device 3202 is fully retracted into the sheath 3216. FIG. 32C illustrates at least embodiments of step 3108 of method 3100 described with respect to FIG. 31.

Figure 32D:
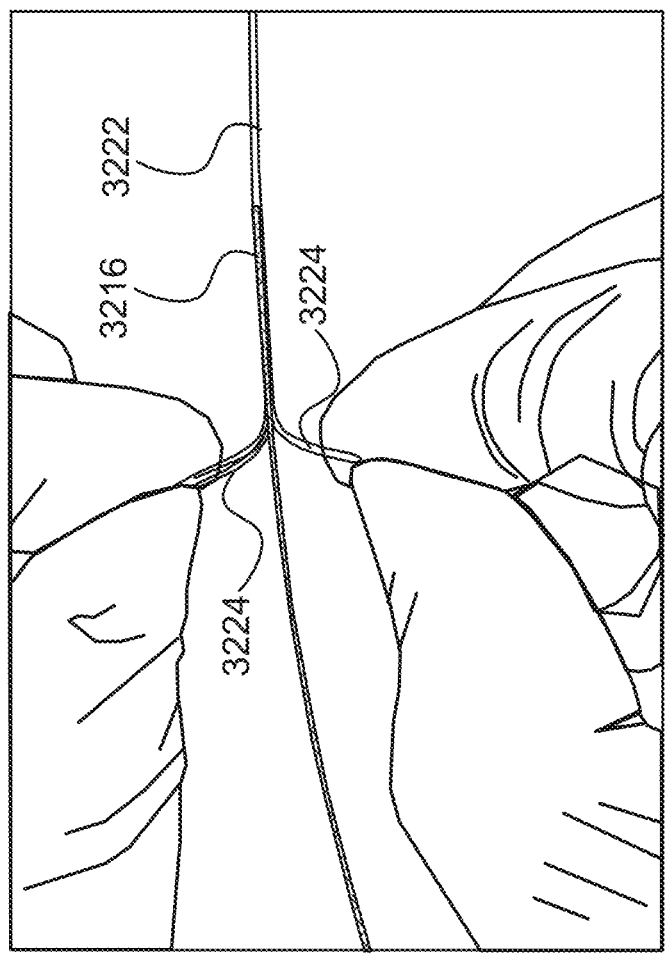
Figure 32E:
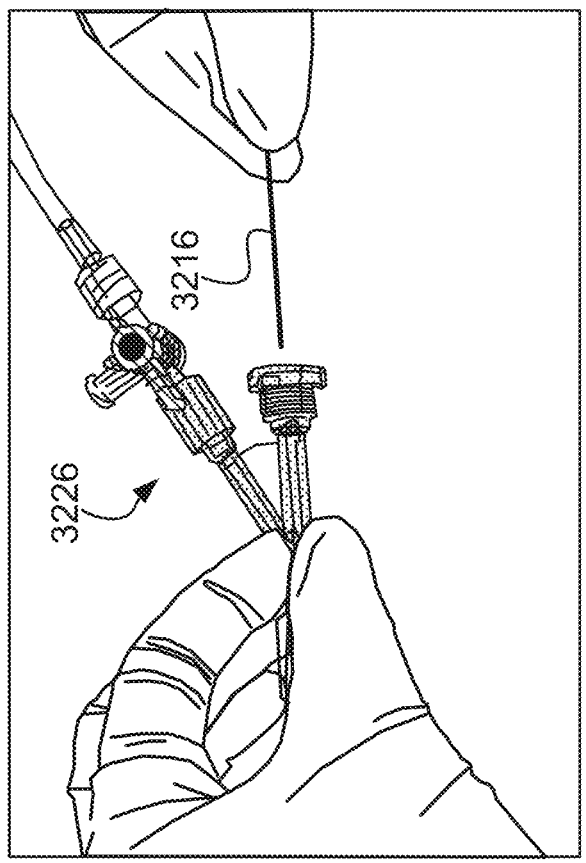

FIG. 32D illustrates removing the peelable tubing 3222 from the sheath 3216 having the device 3202 retracted therein by pulling on one or more tabs 3224. FIG. 32E illustrates inserting the sheath 3216 having the device 3202 retracted therein into a rotating hemostasis valve (RHV) 3226. A distal tip of the sheath 3216 may be seated at the distal end of a microcatheter hub (not shown) and the RHV 3226 may be closed around the sheath 3216 to secure the RHV 3226 to the sheath 3216. The device 3202 may then be advanced until the device 3202 is fully inserted into the microcatheter and the sheath 3216 may be removed, according to at least some embodiments. Further embodiments of deploying the device 3202 may include any of the embodiments described in the present disclosure.

Various embodiments of the present disclosure advantageously reduce the number of sizes (e.g., reduces the inventory) a health care provider has to maintain in stock. For example, instead of carrying a plurality of flow diverters lengths for each diameter, a health care provider is able to provide 26 variations of length and diameter by stocking only 3 sizes customizable flow diverter delivery systems as described herein and illustrated by Table 1 below. Said another way, a health care provider must maintain, track, and store 26 different products as opposed to 3 different products. Accordingly, embodiments of the customizable technology described herein provide the longest length (that is customizable to a desired shorter length) for each desired diameter, thereby reducing the number of SKUs in an inventory by 75% (from 158 SKUs to 26 SKUs, as shown in Table 1 below).

TABLE 1

Size Offering Matrix for Customizable Flow Diverters

| Uncontraint Diameter (mm) | Vessel Diameter (mm) | 10 | 12 | 14 | 16 | 20 | 25 | 30 | 35 | 40 | Catheter ID (inch) | | |
|---|---|---|---|---|---|---|---|---|---|---|---|---|---|
| 2.25 | 2.00 | ● | ● | ● | ● | ● |   |   |   |   | 0.017 | 0.021 | / |
| 2.50 | 2.25 | ● | ● | ● | ● | ● | ● |   |   |   | 0.017 | 0.021 | / |
| 2.75 | 2.50 |   | ● | ● | ● | ● | ● | ● |   |   | 0.017 | 0.021 | / |
| 3.00 | 2.75 |   | ● | ● | ● | ● | ● | ● |   |   | 0.017 | 0.021 | / |
| 3.25 | 3.00 |   |   | ● | ● | ● | ● | ● | ● |   | 0.017 | 0.021 | / |
| 3.50 | 3.25 |   |   | ● | ● | ● | ● | ● | ● |   | 0.017 | 0.021 | / |
| 3.75 | 3.50 |   |   | ● | ● | ● | ● | ● | ● |   | 0.017 | 0.021 | / |
| 4.00 | 3.75 |   |   | ● | ● | ● | ● | ● | ● |   | 0.017 | 0.021 | / |
| 4.25 | 4.00 |   |   | ● | ● | ● | ● | ● | ● |   | 0.017 | 0.021 | / |
| 4.50 | 4.25 |   |   | ● | ● | ● | ● | ● | ● | ● | / | 0.021 | / |
| 4.75 | 4.50 |   |   | ● | ● | ● | ● | ● | ● | ● | / | 0.021 | / |
| 5.00 | 4.75 |   |   | ● | ● | ● | ● | ● | ● | ● | / | 0.021 | / |
| 5.25 | 5.00 |   |   | ● | ● | ● | ● | ● | ● | ● | / | 0.021 | / |
| 5.50 | 5.25 |   |   |   | ● | ● | ● | ● | ● | ● | / | / | 0.027 |
| 5.75 | 5.50 |   |   |   | ● | ● | ● | ● | ● | ● | / | / | 0.027 |
| 6.00 | 5.75 |   |   |   | ● | ● | ● | ● | ● | ● | / | / | 0.027 |
| 6.25 | 6.00 |   |   |   | ● | ● | ● | ● | ● | ● | / | / | 0.027 |

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A system for customizing a flow diverter for delivery into a neurovascular blood vessel to treat an aneurysm, the system comprising:
   an elongate tubular member having a proximal end and a distal end, the elongate tubular member comprising an interior wall defining a lumen;
   a flow diverter comprising a proximal end and a distal end, wherein the flow diverter is partially contained within the lumen of the elongate tubular member in a constrained configuration, wherein the flow diverter extends a first length beyond the distal end of the elongate tubular member;
   a deployment wire extending within the lumen of the elongate tubular member, the deployment wire having a proximal end, a distal end, and a distal portion having a taper, the deployment wire comprising at least one deployment feature coupled to the flow diverter such that movement of the deployment wire relative to the elongate tubular member moves the flow diverter relative to the elongate tubular member; and
   a housing coupled to the elongate tubular member and defining a template for customizing the flow diverter.

2. The system of claim 1, wherein the elongate tubular member comprises an introducer sheath having a proximal end and a distal end, wherein the introducer sheath is cuttable.

3. The system of claim 1, further comprising a tubing extending along and around a distal portion of the elongate tubular member, wherein the tubing extends a second length beyond the distal end of the elongate tubular member, wherein the distal end of the flow diverter is within the tubing, and wherein the tubing is cuttable.

4. The system of claim 3, wherein the tubing is peelably removable from the distal portion of the elongate tubular member.

5. The system of claim 4, wherein the deployment wire terminates in a proximal portion of the peelable tubing.

6. The system of claim 3, wherein the tubing comprises a proximal end, a distal end, a first longitudinal portion having a first proximal pull tab, and a second longitudinal portion having a second proximal pull tab, each of the first longitudinal portion and the second longitudinal portion extending from the proximal end of the tubing to the distal end of the tubing, wherein the tubing is peelably removable from the distal portion of the elongate tubular member by separating the first longitudinal portion from the second longitudinal portion.

7. The system of claim 3, wherein the flow diverter is cuttable within the tubing to a variable length.

8. The system of claim 1, wherein the template comprises equally spaced graduation markings, wherein the graduation markings are configured to aid in cutting the flow diverter to a variable length.

9. The system of claim 8, wherein the template further comprises a cutting aperture, slit, or notch extending through the housing, wherein the cutting aperture, slit, or notch is disposed proximally of the graduation markings.

10. The system of claim 8, wherein the template further comprises an alignment member disposed below the graduation markings for guiding the flow diverter relative to the graduation markings and holding the flow diverter stationary during cutting.

11. The system of claim 8, wherein the template correlates the graduation markings to a deployed length of the flow diverter.

12. The system of claim 1, wherein the template further comprises a cutting aperture extending through the housing, wherein a width of the cutting aperture constrains a cutting tool to aid in cutting the flow diverter at a desired location or desired angle.

13. The system of claim 12, wherein the template further comprises an opening extending through the housing for retraction and advancement of the tubing relative to the graduation markings, wherein the opening is disposed proximally of the cutting aperture.

14. The system of claim 1, wherein the at least one deployment feature comprises:
a pusher extending along and around the distal portion of the deployment wire, the pusher having a distal end configured to engage with the proximal end of the flow diverter;
at least one friction bump positioned along the distal portion of the deployment wire extending distally beyond the pusher, wherein the at least one friction bump is inside of the flow diverter and engaged with a portion of the flow diverter; and
a tip coil extending distally from the at least one friction bump.

15. The system of claim 1, wherein the flow diverter comprises a self-expanding member having a proximal end and a distal end.

16. The system of claim 1, wherein the housing comprises a packaging tray.

17. A method for customizing a flow diverter for delivery into a neurovascular blood vessel to treat an aneurysm, the method comprising:
providing a flow diverter delivery system comprising:
an elongate tubular member having a proximal end and a distal end, the elongate tubular member comprising an interior wall defining a lumen;
a flow diverter comprising a proximal end and a distal end, wherein the flow diverter is partially contained within the lumen of the elongate tubular member in a constrained configuration, wherein the flow diverter extends a first length beyond the distal end of the elongate tubular member;
a deployment wire extending within the lumen of the elongate tubular member, the deployment wire having a proximal end, a distal end, and a distal portion having a taper, the deployment wire comprising at least one deployment feature coupled to the flow diverter;
a housing coupled to the elongate tubular member and defining a template; and
a tubing extending along and around a distal portion of the elongate tubular member, wherein the tubing extends a second length beyond the distal end of the elongate tubular member, wherein the distal end of the flow diverter is within the tubing;
determining a desired length of the flow diverter using the template;
advancing or retracting the tubing relative to the housing to align the flow diverter to the template;
cutting the tubing and the flow diverter such that the flow diverter is cut to the desired length; and
retracting the flow diverter into the elongate tubular member or advancing the elongate tubular member over the flow diverter.

18. The method of claim 17, further comprising separating the tubing from the distal portion of the elongate tubular member after retracting the flow diverter into the elongate tubular member or advancing the elongate tubular member over the flow diverter.

19. The method of claim 18, wherein separating the tubing from the distal portion of the elongate tubular member comprises peeling the tubing away from the distal portion of the elongate tubular member.

20. The method of claim 19, wherein the deployment wire terminates in a proximal portion of the tubing and within the constrained flow diverter.

21. The method of claim 17, further comprising moving the deployment wire relative to the elongate tubular member such that the flow diverter moves relative to the elongate tubular member.

22. The method of claim 17, wherein advancing or retracting the tubing relative to the template includes positioning the flow diverter relative to graduation markings equally spaced along the template, wherein the graduation markings are configured to aid in cutting the flow diverter to the desired length.

23. The method of claim 22, wherein advancing or retracting the tubing relative to the template includes positioning the tubing within an alignment member disposed below the graduation markings for guiding the flow diverter relative to the graduation markings and holding the flow diverter stationary during cutting.

24. The method of claim 22, wherein advancing or retracting the tubing includes adjusting the tubing relative to the graduation markings via an opening extending through the housing and disposed proximally of the graduation markings.

25. The method of claim 22, wherein cutting the tubing and flow diverter comprises using a cutting tool to cut the flow diverter at a desired location or a desired angle via a cutting aperture, slit, or notch extending through the housing.

26. The method of claim 25, wherein the cutting aperture, slit, or notch is positioned between the opening and the graduation markings and constrains the cutting tool during the cutting.

27. The method of claim 22, wherein the template correlates the graduation markings to a deployed length of the flow diverter.

28. The method of claim 22, wherein retracting the flow diverter into the elongate tubular member comprises distally retracting the deployment wire.

29. The method of claim 22, wherein advancing the elongate tubular member over the flow diverter comprises holding the deployment wire stationary while advancing the elongate tubular member.

30. The method of claim 17, wherein the housing comprises a packaging tray.

\* \* \* \* \*